US010226521B2

(12) United States Patent
Curtiss et al.

(10) Patent No.: US 10,226,521 B2
(45) Date of Patent: Mar. 12, 2019

(54) **GENETICALLY MODIFIED *YERSINIA* AS VACCINES AGAINST *YERSINIA* SPECIES**

(71) Applicant: Arizona Board of Regents on behalf of Arizona State University, Scottsdale, AZ (US)

(72) Inventors: Roy Curtiss, Gainesville, FL (US); Wei Sun, Gainesville, FL (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/850,811

(22) Filed: Sep. 10, 2015

(65) Prior Publication Data

US 2016/0089427 A1    Mar. 31, 2016

Related U.S. Application Data

(60) Provisional application No. 62/048,485, filed on Sep. 10, 2014.

(51) Int. Cl.
*A61K 39/00* (2006.01)
*A61K 39/02* (2006.01)
(52) U.S. Cl.
CPC .... *A61K 39/0291* (2013.01); *A61K 2039/522* (2013.01); *A61K 2039/523* (2013.01); *A61K 2039/542* (2013.01); *A61K 2039/572* (2013.01); *A61K 2039/58* (2013.01)
(58) Field of Classification Search
None
See application file for complete search history.

(56) References Cited

U.S. PATENT DOCUMENTS 9,062,297 B2    6/2015  Curtiss et al.
9,492,524 B2 *  11/2016 Carniel .................... C12N 1/36

OTHER PUBLICATIONS

Taylor et al (Microbiology, 151:1919-1926, 2005).*
Blisnick et al (Infection and Immunity, 76(8):3808-3816, 2008).*
Janssen et al. (1969) Plague bacillus: survival within host phagocytes. Science 163: 950-952.
Kaden et al. (2005) Oral immunisation of wild boar against classical swine fever in Baden-Wurttemberg: development of the seroprevalences based on the hunting bag. Eur J Wildlife Res 51: 101-107.
Kang et al.(2002) Immune responses to recombinant pneumococcal PspA antigen delivered by live attenuated *Salmonella enterica* serovar typhimurium vaccine. Infect Immun 70: 1739-1749.
Karbe et al. (1984) Ovine abortion and stillbirth due to purulent placentitis caused by Yersinia pseudotuberculosis. Vet Pathol 21: 601-606.
Karlyshev et al. (1992) Cafl R gene and its role in the regulation of capsule formation of Y pestis. FEBS Lett 305: 37-40.
Karlyshev et al. (1992) A new gene of the fl operon of Y pestis involved in the capsule biogenesis. FEBS Lett 297: 77-80.
Kim et al. (2007) Direct transcriptional control of the plasminogen activator gene of Yersinia pestis by the cyclic AMP receptor protein. J Eacteriol 189: 8890-8900.
Kong et al. (2011) *Salmonella* synthesizing 1-dephosphorylated lipopolysaccharide exhibits low endotoxic activity while retaining its immunogenicity. Journal of immunology 187: 412-423.
Leary et al. (1995) Active immunization with recombinant V antigen from Yersinia pestis protects mice against plague. Infect Immun 63: 2854-2858.
Li et al. (2012) Humoral and cellular immune responses to Yersinia pestis infection in long-term recovered plague patients. Clinical and vaccine immunology : 19: 228-234.
Lin et al. (2011) IL-17 contributes to cell- mediated defense against pulmonary Yersinia pestis infection. Journal of Immunology 186: 1675-1684.
Longenberger et al. (2014) Yersinia enterocolitica infections associated with improperly pasteurized milk products: southwest Pennsylvania, Mar.-Aug. 2011. Epidemiology and Infection 142:1640-1650.
Lotter et al. (2004) Oral vaccination with recombinant Yersinia enterocolitica expressing hybrid type III proteins protects Gerbils from Amebic liver abscess. Infect Immun 72: 7318-7321.
Lukaszewski et al. (2005) Pathogenesis of Yersinia pestis infection in BALB/c mice: effects on host macrophages and neutrophils. Infect Immun 73: 7142-7150.
Meirelles et al. (2011) Reservoir targeted vaccine for lyme borreliosis induces a yearlong, neutralizing antibody response to OspA in white-footed mice. Clinical and vaccine immunology 18: 1809-1816.
Mencher et al. (2004) Protection of black-tailed prairie dogs (*Cynomys ludovicianus*) against plague after voluntary consumption of baits containing recombinant raccoon poxvirus vaccine. Infect Immun 72: 5502-5505.
Meyer et al. (1974) Plague immunization. VI. Vaccination with the fraction I antigen of Yersinia pestis. The Journal of infectious diseases 129: Suppl:S41-45.
Monack et al. (1998) Yersinia-induced apoptosis in vivo aids in the establishment of a systemic infection of mice. The Journal of experimental medicine 188: 2127-2137.
Montminy et al. (2006) Virulence factors of Yersinia pestis are overcome by a strong lipopolysaccharide response. Nat Immunol 7: 1066-1073.
Morelli et al. (2010) Yersinia pestis genome sequencing identifies patterns of global phylogenetic diversity. Nat Genet 42: 1140-1143.

(Continued)

*Primary Examiner* — Patricia Duffy
(74) *Attorney, Agent, or Firm* — McCarter & English, LLP; Marcie B. Clarke

(57) ABSTRACT

Recombinant attenuated *Y. pseudotuberculosis* mutants have been created that show efficacy as oral vaccines against plague caused by *Y. pestis* and Yersinosis caused by both *Y. enterocolitica* and *Y. pseudotuberculosis*. Thus, live attenuated *Y. pseudotuberculosis*-based vaccines can be used to prevent Yersinosis in farm animals such as swine, cattle and sheep. The palatable baits containing live attenuated *Y. pseudotuberculosis*-based vaccines may be acceptable methods to control plague epidemics in wild animals. The methods disclosed can also be used to generate recombinant attenuated *Y. entercolitica* and *Y. pestis* vaccine strains.

5 Claims, 46 Drawing Sheets

Specification includes a Sequence Listing.

(56) References Cited

OTHER PUBLICATIONS

Motin et al. (1994) Passive immunity to yersiniae mediated by anti-recombinant V antigen and protein A-V antigen fusion peptide. Infection and immunity 62: 4192-4201.
Murphy et al. (2007) Yersinia pestis YadC: a novel vaccine candidate against plague. Adv Exp Med Biol 603: 400-414.
Nakayama et al. (1988) Construction of an Asd+ expression vector: stable maintenance and high expression of cloned genes in a *Salmonella* vaccine strain. Bio/Technology 6: 693-697.
Nilles et al. (1998) The V antigen of Yersinia pestis regulates Yop vectorial targeting as well as Yop secretion through effects on YopB and LcrG. J Bacteriol 180: 3410-3420.
Nol et al. (2009) Humoral immune responses of white-tailed deer (*Odocoileus virginianus*) to *Mycobacterium bovis* BCG vaccination and experimental challenge with *M bovis*. Clinical and vaccine immunology : CVI 16: 323-329.
Nol et al. (2008) Efficacy of oral and parenteral routes of *Mycobacterium bovis* bacille Calmette-Guerin vaccination against experimental bovine tuberculosis in white-tailed deer (*Odocoileus virginianus*): a feasibility study. J Wildlife Dis 44: 247-259.
Ogra et al. (2001) Vaccination strategies for mucosal immune responses. Clinical microbiology reviews 14: 430-445.
Okan et al. (2010) The smpB-ssrA mutant of Yersinia pestis functions as a live attenuated vaccine to protect mice against pulmonary plague infection. Infect Immun 78: 1284-1293.
Orloski et al. (1995) Yersinia pestis infection in three dogs. J Am Vet Med Assoc 207: 316-318.
Orth, K. (2002) Function of the Yersinia effector YopJ. Current opinion in microbiology 5: 38-43.
Orth et al. (2000) Disruption of signaling by Yersinia effector YopJ, a ubiquitin-like protein protease. Science 290: 1594-1597.
Paquette et al. (2012) Serine/threonine acetylation of TGFbeta-activated kinase (TAKI ) by Yersinia pestis YopJ inhibits innate immune signaling. P Natl Acad Sci USA 109: 12710-12715.
Parent et al. (2005) Cell-mediated protection against pulmonary Yersinia pestis infection. Infect Immun 73: 7304-7310.
Parent et al. (2006) Gamma interferon, tumor necrosis factor alpha, and nitric oxide synthase 2, key elements of cellular immunity, perform critical protective functions during humoral defense against lethal pulmonary Yersinia pestis infection. Infect Immun 74: 3381-3386.
Parkhill et al. (2001) Genome sequence of Yersinia pestis, the causative agent of plague. Nature 413: 523-527.
Pashine et al. (1999) Thl dominance in the immune response to live *Salmonella typhimurium* requires bacterial invasiveness but not persistence. International Immunology 11: 481-489.
Perez-Gutierrez et al. (2010) Role of lipid A acylation in Yersinia enterocolitica virulence. Infect Immun 78: 2768-2781.
Perry et al. (1997) Yersinia pestis—etiologic agent of plague. Clin Microbiol Rev 10: 35-66.
Pettersson et al. (1999) The V-antigen of Yersinia is surface exposed before target cell contact and involved in virulence protein translocation. Molecular Microbiology 32: 961-976.
Philipovskiy et al. (2007) Vaccination with live Yersinia pestis primes CD4 and CD8 T cells that synergistically protect against lethal pulmonary Y pestis infection. Infect Immun 75: 878-885.
Piesman, J. (2006) Strategies for reducing the risk of Lyme borreliosis in North America. International journal of medical microbiology 296 Suppl 40:17-22.
Pujol et al. (2005) Replication of Yersinia pestis in interferon gamma-activated macrophages requires ripA, a gene encoded in the pigmentation locus. Proc Natl Acad Sci U S A 102: 12909-12914.
Qi et al. (2010) Comparison of mouse, guinea pig and rabbit models for evaluation of plague subunit vaccine FI +rV270. Vaccine 28: 1655-1660.
Qiu et al. (2010) Comparison of immunological responses of plague vaccines FI+rV270 and EV76 in Chinese-origin rhesus macaque, Macaca mulatta. Scandinavian journal of immunology 72: 425-433.
Quenee et al. (2011) Prevention of pneumonic plague in mice, rats, guinea pigs and non-human primates with clinical grade rV IO, rV I0-2 or FI-V vaccines. Vaccine 29: 6572-6583.
Quenee et al. (2008) Yersinia pestis cafl variants and the limits of plague vaccine protection. Infect Immun 76: 2025-2036.
Rayor, L S. (1985) Dynamics of a plague outbreak in Gunnison's prairie dog. Journal of Mammalogy 66(1): 194-196.
Rebeil et al. (2004) Variation in lipid a structure in the pathogenic yersiniae. Mol Microbiol 52: 1363-1373.
Rocke et al. (2008) Immunization of black-tailed prairie dog against plague through consumption of vaccine-laden baits. J Wild Dis 44: 930-937.
Rodrigues et al. (1992) Antigen FI from Yersinia pestis forms aqueous channels in lipid bilayer membranes. Braz J Med Biol Res 25: 75-79.
Zhang et al. (2010) YopJ-promoted cytotoxicity and systemic colonization are associated with high levels of murine interleukin-I 8, gamma interferon, and neutrophils in a live vaccine model of Yersinia pseudotuberculosis infection. Infect Immun 78: 2329-2341.
Zhang et al. (2005) Role of macrophage apoptosis in the pathogenesis of Yersinia. Curr Top Microbiol Immunol 289: 151-173.
Zhou et al. (2009) Molecular Darwinian evolution of virulence in Yersinia pestis. Infect Immun 77: 2242-2250.
Zhou et al. (2005) Yersinia virulence factor YopJ acts as a deubiquitinase to inhibit NF-kappa B activation. Journal of Experimental Medicine 202: 1327-1332.
The European Union Summary Report on Trends and Sources of Zoonoses, Zoonotic Agents and Food-borne Outbreaks in 2011. EFSA Journal 2013;11(4):3129.
NC1202: Enteric Diseases of Food Animals: Enhanced Prevention, Control and Food Safety. Website: http://www.nimss.org/projects/view/mrp/outline/14217. Mar. 23, 2016.
Achtman et al. (2004) Microevolution and history of the plague bacillus, Yersinia pestis. Proc Natl Acad Sci U S A 101: 17837-17842.
Achtman et al. (1999) Yersinia pestis, the cause of plague, is a recently emerged clone of Yersinia pseudotuberculosis. Proc Natl Acad Sci U S A 96: 14043-14048.
Aepfelbacher, M. (2004) Modulation of Rho GTPases by type III secretion system translocated effectors of Yersinia. Rev Physiol Biochem Pharmacol 152: 65-77.
Aldwell, et al. (2003) Oral vaccination with *Mycobacterium bovis* BCG in a lipid formulation induces resistance to pulmonary tuberculosis in brushtail possums. Vaccine 22: 70-76.
Anderson et al. (1998) Short- and long-term efficacy of single-dose subunit vaccines against Yersinia pestis in mice. Am J Trop Med Hyg 58: 793-799.
Anderson et al. (1996) Recombinant V antigen protects mice against pneumonic and bubonic plague caused by FI-capsule-positive and -negative strains of Yersinia pestis. Infect Immun 64:4580-4585.
Andrews et al. (1996) Fraction 1 capsular antigen (FI) purification from Yersinia pestis C092 and from an *Escherichia coli* recombinant strain and efficacy against lethal plague challenge. Infect Immun 64:2180-2187.
Anisimov et al. (2010) Amino acid and structural variability of Yersinia pestis LcrV protein. Infection Genetics and Evolution 10: 137-145.
Ballesteros et al. (2009) First data on Eurasian wild boar response to oral immunization with BCG and challenge with a *Mycobacterium bovis* field strain. Vaccine 27: 6662-6668.
Ballesteros et al. (2011) Acceptance and palatability for domestic and wildlife hosts of baits designed to deliver a tuberculosis vaccine to wild boar piglets. Preventive veterinary medicine 98: 198-203.
Bernardino-Varn et al. (2013) Prevalence of Yersinia enterocolitica in Raw Cow's Milk Collected from Stables of Mexico City. J Food Protect 76: 694-698.
Bertani, G. (1951) Studies on lysogenesis. I. The mode of phage liberation by lysogenic *Escherichia coli*. J Bacteriol 62:293-300.
Bhattacharya et al. (2011) Development of a baited oral vaccine for use in reservoir-targeted strategies against Lyme disease. Vaccine 29: 7818-7825.

(56) References Cited

OTHER PUBLICATIONS

Bliska, J. B. (2006) Yersinia inhibits host signaling by acetylating MAPK kinases. ACS chemical biology 1: 349-351.
Bottone, E. J. (1997) Yersinia enterocolitica: the charisma continues. Clinical microbiology reviews 10: 257-276.
Braciale et al. (2008) Correlates of Immunity Elicited by Live Yersinia pestis Vaccine. Infectious Diseases 23: 473-480.
Branger et al. (2007) Oral vaccination with different antigens from Yersinia pestis KIM delivered by live attenuated *Salmonella typhimurium* elicits a protective immune response against plague. Adv Exp Med Biol 603: 387-399.
Branger et al. (2010) Evaluation of Psn, HmuR and a modified LcrV protein delivered to mice by live attenuated *Salmonella* as a vaccine against bubonic and pneumonic Yersinia pestis challenge. Vaccine 29: 274-282.
Brodsky et al. (2010) A Yersinia effector protein promotes virulence by preventing inflammasome recognition of the type III secretion system. Cell Host Microbe 7: 376-387.
Brozek et al. (1990) Biosynthesis of lipid A in *Escherichia coli*. Acyl carrier protein-dependent incorporation of laurate and myristate. J Biol Chem 265: 15410-15417.
Brubaker, R. R. (1991) Factors promoting acute and chronic diseases caused by yersiniae. Clin Microbiol Rev 4: 309-324.
Bucher et al. (2008) Epidemiological data on pathogenic Yersinia enterocolitica in Southern Germany during 2000-2006. Foodborne Pathogens and Disease 5: 273-280.
Buchrieser et al. (1999) The 102-kilobase pgm locus of Yersinia pestis: sequence analysis and comparison of selected regions among different Yersinia pestis and Yersinia pseudo tuberculosis strains. Infect Immun 67: 4851-4861.
Chain et al. (2004) Insights into the evolution of Yersinia pestis through whole-genome comparison with Yersinia pseudotuberculosis. Proc Natl Acad Sci U S A 101: 13826-13831.
Chomel et al. (1994) Serological surveillance of plague in dogs and cats, California, 1979-1991. Comp Immunol Microbiol Infect Dis 17: 111-121.
Collazo et al. (1997) The invasion-associated type III system of *Salmonella typhimurium* directs the translocation of Sip proteins into the host cell. Molecular microbiology 24: 747-756.
Corbel et al. (1992) Experimental Yersinia enterocolitica placentitis in Sheep. Brit Vet J 148: 339-349.
Cross et al. (2007) The potential of oral vaccines for disease control in wildlife species. Veterinaryjournal 174: 472-480.
Dewoody et al. (2011) YopK regulates the Yersinia pestis type III secretion system from within host cells. Molecular Microbiology 79: 1445-1461.
Doll et al. (1994) Cat-transmitted fatal pneumonic plague in a person who traveled from Colorado to Arizona. Am J Trop Med Hyg 51: 109-114.
Elvin et al. (2004) Stat 4 but not Stat 6 mediated immune mechanisms are essential in protection against plague. Microb Pathog 37: 177-184.
Erfurth et al. (2004) Yersinia enterocolitica induces apoptosis and inhibits surface molecule expression and cytokine production in murine dendritic cells. Infection and immunity 72: 7045-7054.
Feldman et al. (2002) SycE allows secretion of YopE-DHFR hybrids by the Yersinia enterocolitica type III Ysc system. Molecular microbiology 46: 1183-1197.
Fields et al. (1999) Virulence role of V antigen of Yersinia pestis at the bacterial surface. Infect Immun 67: 5395-5408.
Finnegan et al. (2002) Rabies in North America and Europe. J R Soc Med 95: 9-13.
Fondrevez et al. (2014) Prevalence of pathogenic Yersinia enterocolitica in slaughter-aged pigs during a one-year survey, 2010-2011, France. International Journal of Food Microbiology 174: 56-62.
Forman et al. (2008) yadEC of Yersinia pestis, a new virulence determinant for bubonic plague. Infect Immun 76: 578-587.
Gabastou et al. (2000) An outbreak of plague including cases with probable pneumonic infection, Ecuador, 1998. Trans R Soc Trop Med Hyg 94: 387-391.
Galindo et al.(2011) Pathogenesis of Y enterocolitica and Y pseudotuberculosis in Human Yersiniosis. J Pathog 2011: 182051.
Galyov et al. (1991) Expression of the envelope antigen Fl of Yersinia pestis is mediated by the product of cafIM gene having homology with the chaperone protein PapD of *Escherichia coli*. FEBS Lett 286: 79-82.
Galyov et al. (1990) Nucleotide sequence of the Yersinia pestis gene encoding FI antigen and the primary structure of the protein. Putative T and B cell epitopes. FEBS Lett 277: 230-232.
Giambartolomei et al. (1999) Induction of pro- and anti-inflammatory cytokines by Borrelia burgdorferi lipoproteins in monocytes is mediated by CD14. Infection and immunity 67: 140-147.
Giannitti et al. (2014) Yersinia pseudotuberculosis infections in goats and other animals diagnosed at the California Animal Health and Food Safety Laboratory System: 1990-2012. Journal of Veterinary Diagnostic Investigation 26: 88-95.
Gong et al. (2001) Characterization of the Yersinia pestis Yfu ABC inorganic iron transport system. Infect Immun 69: 2829-2837.
Gormley et al. (2009) Control of TB in wildlife by oral BCG vaccination. Expert review of vaccines 8: 1339-1342.
Gould et al. (2008) Dog-associated risk factors for human plague. Zoonoses Public Health 55: 448-454.
Harvey et al. (1976) Recovery of Yersinia enterocolitica from streams and lakes of California. Appl Environ Microb 32: 352-354.
Heath et al. (1998) Protection against experimental bubonic and pneumonic plague by a recombinant capsular FI-V antigen fusion protein vaccine. Vaccine 16: 1131-1137.
Holmstrom et al. (1997) YopK of Yersinia pseudotuberculosis controls translocation of Yop effectors across the eukaryotic cell membrane. Mol Microbiol 24: 73-91.
Hubbert, W. T. (1972) Yersiniosis in mammals and birds in the United States: case reports and review. The American journal of tropical medicine and hygiene 21: 458-463.
Ruckdeschel, K. (2002) Immunomodulation of macrophages by pathogenic *Yersinia* species. Archivum immunologiae et therapiae experimentalis 50: 131-137.
Rundell, et al. (2014) A multiplex PCR/LDR assay for simultaneous detection and identification of the NIAID category B bacterial food and water-borne pathogens. Diagn Microbiol Dis. pp. 135-140.
Rupprecht et al. (2004) Oral vaccination of wildlife against rabies: opportunities and challenges in prevention and control. Dev Biol (Basel) 119: 173-184.
Russmann et al. (2003) Attenuated Yersinia pseudotuberculosis carrier vaccine for simultaneous antigen-specific CD4 and CD8 T-cell induction. Infect Immun 71: 3463-3472.
Russmann et al. (2001) Protection against murine listeriosis by oral vaccination with recombinant *Salmonella* expressing hybrid Yersinia type III proteins. J Immunol 167: 357-365.
Russmann et al. (2000) Yersinia enterocolitica-mediated translocation of defined fusion proteins to the cytosol of mammalian cells results in peptide-specific MHC class I-restricted antigen presentation. Eur J Immunol 30: 1375-1384.
Sarker et al. (1998) The Yersinia Yop virulon: LcrV is required for extrusion of the translocators YopB and YopD. J Bacteriol 180: 1207-1214.
Schleifer et al. (1972) Peptidoglycan Types of Bacterial Cell-Walls and Their Taxonomic Implications. Bacteriol Rev 36: 407-477.
Scott et al. (2000) Economic cost to New Zealand of foodborne infectious disease. New Zeal Med J 113: 281-284.
Shreewastav et al. (2012) Cell-mediated immune response to epitopic MAP (multiple antigen peptide) construct of LcrV antigen of Yersinia pestis in murine model. Cellular immunology 278: 55-62.
Simpson et al. (1990) Recombinant capsular antigen (fraction 1) from Yersinia pestis induces a protective antibody response in BALB/c mice. The American journal of tropical medicine and hygiene 43: 389-396.
Skurnik et al. (2000) Characterization of the O-antigen gene clusters of Yersinia pseudotuberculosis and the cryptic O-antigen gene cluster of Yersinia pestis shows that the plague bacillus is most closely related to and has evolved from Y pseudotuberculosis serotype O: Ib. Molecular microbiology 37: 316-330.

(56) References Cited

OTHER PUBLICATIONS

Slee et al. (1990) Enteritis in Sheep, Goats and Pigs due to Yersinia pseudotuberculosis infection. Aust Vet J 67: 320-322.
Smego et al. (1999) Yersiniosis I: microbiological and clinicoepidemiological aspects of plague and non-plague Yersinia infections. Eur J Clin Microbial Infect Dis 18: 1-15.
Smiley, S. T. (2008) Current challenges in the development of vaccines for pneumonic plague. Expert review of vaccines 7: 209-221.
Smiley, S. T. (2008) Immune defense against pneumonic plague. Immunol Rev 225: 256-271.
Straley et al. (1986) Virulence genes regulated at the transcriptional level by Ca2+ in Yersinia pestis include structural genes for outer membrane proteins. Infect Immun 51: 445-454.
Sun et al. (2012) Amino acid substitutions in LcrV at putative sites of interaction with toll-like receptor 2 do Oral challenge with $1.7 \times 10^9$ CFU of *Y. pseudotuberculosis* PB1+

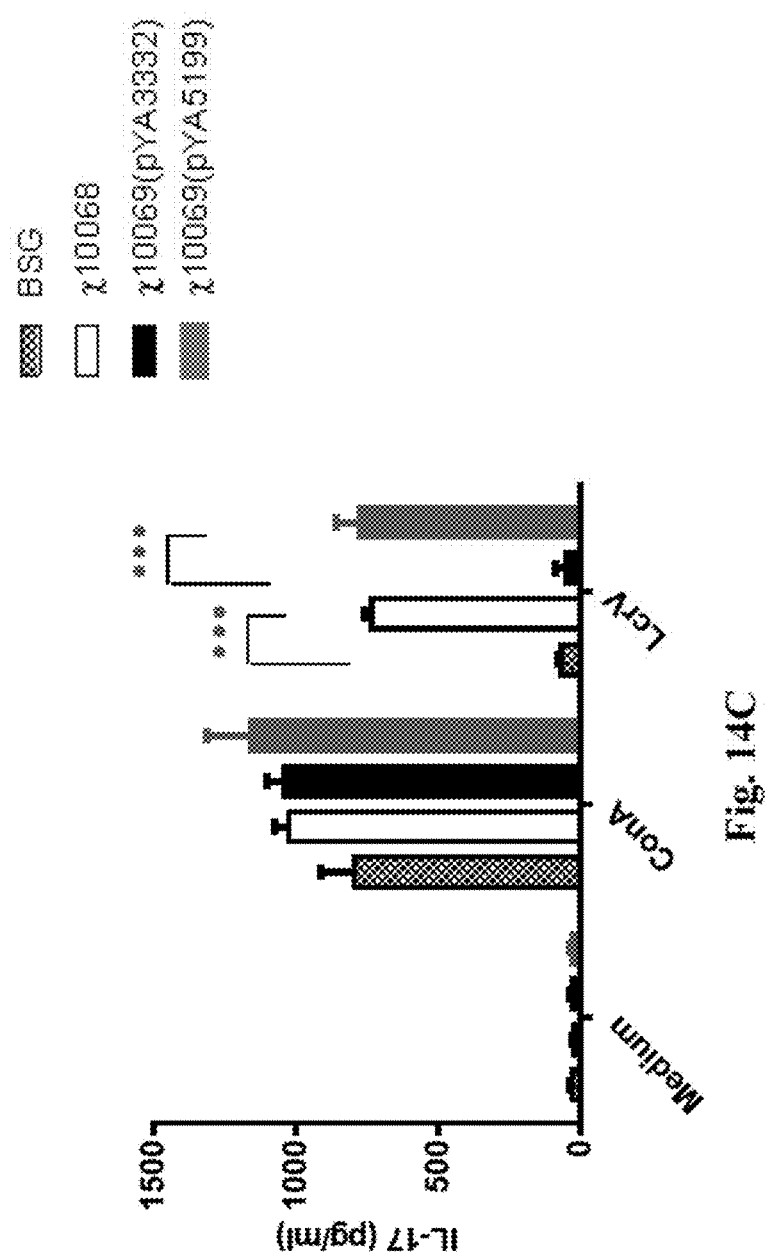

SEQUENCE LISTING

<160> NUMBER OF SEQ ID NOS: 33

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
cggtccggag acattactaa gtgagcgttg ta            32

<210> SEQ ID NO 2
<211> LENGTH: 51
<212> TYPE: DNA
<213> ORGANISM: Artificial Sequence
<220> FEATURE:
<223> OTHER INFORMATION: primer

<400> SEQUENCE: 2
gttttgttcg taggctctaa tcatcgtagc gaactgatca tgatttttct g        51

<210> SEQ ID NO 3
<211> LENGTH: 52
<212> TYPE: DNA
<213> ORGANISM: Artificial Sequence
<220> FEATURE:
<223> OTHER INFORMATION: primer

<400> SEQUENCE: 3
gaaaaatcat gatcagttcg ctacgatgat tagagcctac gaacaaaacc ca       52

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
cggaagcttt catttaccag acgtgtcatc ta                             32

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5
cggggtaccc gtattgcgcc gcataaagg                                 29

<210> SEQ ID NO 6
<211> LENGTH: 47
<212> TYPE: DNA
<213> ORGANISM: Artificial Sequence
<220> FEATURE:
<223> OTHER INFORMATION: primer

<400> SEQUENCE: 6
ctgagctcgg cagcctgcag agccatctac gatgggctga cagactg             47

<210> SEQ ID NO 7
<211> LENGTH: 46
<212> TYPE: DNA
<213> ORGANISM: Artificial Sequence
<220> FEATURE:
<223> OTHER INFORMATION: primer

<400> SEQUENCE: 7
ctctgcaggc tgccgagctc agacgccgta atacatcca tgtagg               46

<210> SEQ ID NO 8
<211> LENGTH: 29
<212> TYPE: DNA
<213> ORGANISM: Artificial Sequence
<220> FEATURE:
<223> OTHER INFORMATION: primer

```
<400> SEQUENCE: 8
cggggtacct gcggcaaacc acctcaaag                                    29

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
cgggagctct tgaacttatc atcaggcgaa ggcct                             35

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
cggctgcagg ctttccggta ataccggac                                    29

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
cggcccgggc tgatagatca actgcgcgct cca                               33

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
cggggtaccc ttaacgggtg ccgtaaacga cga                               33

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
cggggtaccc ttaacgggtg ccgtaaacga cga                               33

<210> SEQ ID NO 14
<211> LENGTH: 48
<212> TYPE: DNA
<213> ORGANISM: Artificial Sequence
<220> FEATURE:
<223> OTHER INFORMATION: primer

<400> SEQUENCE: 14
acgctatgcg ccgctaaaaa atagtgttta ctgccctgcc ttggaagg               48
```

<210> SEQ ID NO 15
<211> LENGTH: 48
<212> TYPE: DNA
<213> ORGANISM: Artificial Sequence
<220> FEATURE:
<223> OTHER INFORMATION: primer

<400> SEQUENCE: 15
cagggcagta aacactattt tttagcggcg catagcgtgt catatcgt                48

<210> SEQ ID NO 16
<211> LENGTH: 36
<212> TYPE: DNA
<213> ORGANISM: Artificial Sequence
<220> FEATURE:
<223> OTHER INFORMATION: primer

<400> SEQUENCE: 16
cggcccgggc tatagtatgc ccgtccggtt tcatcc                            36

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
cggggtacca cggacccttta gcaccgttct cgatagaga                        39

<210> SEQ ID NO 18
<211> LENGTH: 48
<212> TYPE: DNA
<213> ORGANISM: Artificial Sequence
<220> FEATURE:
<223> OTHER INFORMATION: primer

<400> SEQUENCE: 18
cgagctcggc agcctgcagg ccaaaaaccg cagggcgcac tacgaaga               48

<210> SEQ ID NO 19
<211> LENGTH: 47
<212> TYPE: DNA
<213> ORGANISM: Artificial Sequence
<220> FEATURE:
<223> OTHER INFORMATION: primer

<400> SEQUENCE: 19
cctgcaggct gccgagctcg gcatcggtgg gggggcagag gcaagga                47

<210> SEQ ID NO 20
<211> LENGTH: 37
<212> TYPE: DNA
<213> ORGANISM: Artificial Sequence
<220> FEATURE:
<223> OTHER INFORMATION: primer

<400> SEQUENCE: 20
cggcccgggc ggcaacttct aatccgggaa tatctga                           37

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
gccaaaggcc aattagattg cagtta                                          26

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
cgcgtgacat ccgcggcaat ggcga                                           25

<210> SEQ ID NO 23
<211> LENGTH: 43
<212> TYPE: DNA
<213> ORGANISM: Artificial Sequence
<220> FEATURE:
<223> OTHER INFORMATION: primer

<400> SEQUENCE: 23
cggctgcagg cctattatat tgcttcgcgc tctctattct tag                       43

<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24
cgggagctcc ttttaatcat acaggtgatt cca                                  33

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
cggcccgggg atagagccta caataaatta taaccaatag                           40

<210> SEQ ID NO 26
<211> LENGTH: 48
<212> TYPE: DNA
<213> ORGANISM: Artificial Sequence
<220> FEATURE:
<223> OTHER INFORMATION: primer

<400> SEQUENCE: 26
ctccaactca gatttcatag ttactactcc caaatttact ttataaac                  48

<210> SEQ ID NO 27
<211> LENGTH: 48
<212> TYPE: DNA
<213> ORGANISM: Artificial Sequence
<220> FEATURE:
<223> OTHER INFORMATION: primer

<400> SEQUENCE: 27
gtaaatttgg gagtagtaac tatgaaatct gagttggagg aattgagt                  48

```
<210> SEQ ID NO 28
<211> LENGTH: 31
<212> TYPE: DNA
<213> ORGANISM: Artificial Sequence
<220> FEATURE:
<223> OTHER INFORMATION: primer

<400> SEQUENCE: 28
gttccggtac cgccagcggt gatgggttac a                               31

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
gacacccacc gctcagtgca ttgtgca                                    27

<210> SEQ ID NO 30
<211> LENGTH: 37
<212> TYPE: DNA
<213> ORGANISM: Artificial Sequence
<220> FEATURE:
<223> OTHER INFORMATION: primer

<400> SEQUENCE: 30
cggggtacca gccttgagtt gatatatccg agaatag                         37

<210> SEQ ID NO 31
<211> LENGTH: 39
<212> TYPE: DNA
<213> ORGANISM: Artificial Sequence
<220> FEATURE:
<223> OTHER INFORMATION: primer

<400> SEQUENCE: 31
tacattatac atccgatata tcagtttcca actgtgtta                       39

<210> SEQ ID NO 32
<211> LENGTH: 41
<212> TYPE: DNA
<213> ORGANISM: Artificial Sequence
<220> FEATURE:
<223> OTHER INFORMATION: primer

<400> SEQUENCE: 32
gatatatcgg atgtataatg tattttggaa atcttgctcc a                    41

<210> SEQ ID NO 33
<211> LENGTH: 37
<212> TYPE: DNA
<213> ORGANISM: Artificial Sequence
<220> FEATURE:
<223> OTHER INFORMATION: primer

<400> SEQUENCE: 33
cggcccgggg atattcagcg attgatcaga tcgctta                         37
```

GENETICALLY MODIFIED *YERSINIA* AS VACCINES AGAINST *YERSINIA* SPECIES

CROSS-REFERENCE TO RELATED APPLICATIONS

This application claims priority to U.S. Provisional Patent Application No. 62/048,485, filed Sep. 10, 2014, the entire contents of which are incorporated herein in their entirety by reference.

GOVERNMENTAL RIGHTS

This invention was made with government support under R21 AI095872 awarded by the National Institutes of Health. The government has certain rights in the invention.

FIELD OF THE INVENTION

This disclosure relates to genetically engineered bacteria and more particularly to genetically engineered *Yersinia pseudotuberculosis* strains.

BACKGROUND

The genus *Yersinia* includes three pathogenic species: *Yersinia pestis, Yersinia enterocolitica* and *Yersinia pseudotuberculosis*, which are implicated in sub-lethal and lethal infections in animals and humans (Brubaker, 1991).

*Y. pestis*, the etiologic agent causing plague in humans, has been responsible for high mortality in several epidemics throughout human history and remains a current threat as a potential biological warfare agent. Currently, about 2000 global cases of plague are reported to the World Health Organization each year. Most of these cases are the bubonic form, usually a consequence of the transmission of bacteria to humans via bites from fleas that have previously fed on infected rodents, and cross-infection occurring from domestic and wild animal contacts, including guinea pigs (Gabastou et al., 2000), prairie dogs (CLARK, 1977, Rayor, 1985), squirrels and other small rodents (Smego et al., 1999) or larger mammals, such as cats (Doll et al., 1994), dogs (Gould et al., 2008, Orloski & Eidson, 1995, Chomel et al., 1994, Pashine et al., 1999, Giambartolomei et al., 1999, Wang et al., 2011a), coyotes (Smego et al., 1999) and lions (Wong et al., 2009). The trends in plague epidemiology are the increased transmission of plague from wild rodents to domestic animals (cats or dogs) as residential areas encroach on enzootic plague foci and from domestic animals to their owners and veterinarians (Rollins et al., 2003, Perry & Fetherston, 1997). Large reservoirs of *Y. pestis* still exist on all major inhabited continents, except Australia (Perry & Fetherston, 1997). The reservoir for *Y. pestis* includes a variety of small, warm-blooded mammals including mice, rats, squirrels, chipmunks, rabbits, voles and prairie dogs (Cynomys spp.) (Perry & Fetherston, 1997).

Recently, the main focus of plague vaccine research has been to develop subunit vaccines, in particular targeting LcrV and F1 antigens, which were found to efficiently protect rodent and cynomolgus macaque against bubonic and pneumonic plague and are well tolerated in humans (Anderson et al., 1998, Andrews et al., 1996, Heath et al., 1998, Leary et al., 1995, Simpson et al., 1990, Une & Brubaker, 1984, Williamson et al., 1995b, Williamson et al., 2005, Quenee et al., 2011). However, the subunit vaccine had insufficient and highly variable protection against plague in African Green monkeys (Quenee et al., 2011, Smiley, 2008a). Additionally, the usefulness of F1 as a protective antigen is not clear, since strains can cause plague (Winter et al., 1960). Therefore, vaccines composed of a limited number of antigens (F1 and/or LcrV) may not be able to protect against F1-negative strains (Winter et al., 1960) or strains harboring LcrV variants (Anisimov et al., 2010).

Yersiniosis, a diarrheal illness, is typically a self-limiting disease in humans, mainly caused by *Y. enterocolitica* and *Y. pseudotuberculosis* which are transmitted via fecal-oral route from soil, water and a variety of animal food sources (Brubaker, 1991, Bottone, 1997, Galindo et al., 2011). In the Netherlands in the 1990s, *Y. enterocolitica* was the third most common bacterial cause of diarrhea, after *Campylobacter* and *Salmonella*. In 2011, yersiniosis was the fourth most frequently reported zoonosis in the EU with an overall notification rate of 1.63 cases per 100,000 population. The case fatality rate of human yersiniosis was 0.02% in 2011. *Y. enterocolitica* was the most common species reported in human cases and was isolated from 98.4% of the confirmed cases. Yersiniosis is one of the three leading foodborne zoonoses in Lithuania, and the incidence of 12.86 per 100,000 population in Lithuania was the highest among European Union (EU) member states in 2010 (Team, 2013, Bucher et al., 2008). Additionally, high rates of infection have been described in New Zealand. The incidence was reported to be 87/100,000, making it more common than *Salmonellosis*. The majority of isolates were *Y. enterocolitica* serotype O:3. The estimates of the cost of output loss due to Yersiniosis in 2009 was 1.06 million dollars in New Zealand (Scott et al., 2000).

Several studies have linked outbreaks of human yersiniosis to the consumption of contaminated foods, including pork meat and vegetables, as well as water. Pigs are of particular importance in *Yersinia* spp. epidemiology, as they are the main carriers and source of human enteropathogenic *Y. enterocolitica*, especially bioserotype 4/O:3, and *Y. pseudotuberculosis* bioserotype 2/O:3. *Y. pseudotuberculosis* and *Y. enterocolitica* (O serotype) have been isolated from ovine abortion cases. Infection of ewes with *Y. pseudotuberculosis* can lead to abortion, stillbirth or birth of weak or healthy lambs. Infection with *Y. enterocolitica* resulted in placentitis and abortion, with subsequent normal pregnancies (Galindo et al., 2011). In 2000, USDA ERS (USDA Economic Research Service) estimated $6.9 billion/year for medical costs, productivity losses, and costs of premature deaths for diseases caused by common foodborne pathogens including *enterica* pathogenic *Yersinia* species (Hubbert, 1972). Besides human health risks, animal diarrheal disease due to food-safety related pathogens and other animal-specific pathogens remain an economically important cause of production loss to livestock producers (Vanantwerpen et al., 2014, Fondrevez et al., 2014, Giannitti et al., 2014, Longenberger et al., 2014, Bernardino-Varo et al., 2013, Karbe & Erickson, 1984, Corbel et al., 1992, Slee & Button, 1990).

Currently, there are no effective vaccines to control zoonotic *Y. pestis* transmission in wild rodents and prevent enteric Yersiniosis in swine and cattle. Here, several *Y. pseudotuberculosis* rationally designed attenuated constructions will provide the advantage of simultaneously priming humoral and cellular immune responses against many *Yersinia* antigens, thereby greatly enhancing the likelihood of broad-based protection against plague and Yersiniosis.

SUMMARY OF THE INVENTION

The embodiments disclosed herein relate to live attenuated *Y. pseudotuberculosis* constructions. These constructions are highly attenuated. Oral immunization with these constructions affords great protection against three pathogenic Yersinia species, *Y. enterocolitica*, *Y. pseudotuberculosis* and *Y. pestis* in mice. Thus, orally administered live attenuated *Y. pseudotuberculosis* bacteria as bait vaccines may offer a very promising prospect to control plague transmission in wild-life reservoirs and protect farm animals (swine, cattle) and humans from Yersiniosis caused by *Y. enterocolitica* and *Y. pseudotuberculosis.*

Some embodiments include: the regulatory protein is a cAMP receptor protein (Crp), which is encoded by the crp gene. The bacterium can be attenuated by replacing the crp promoter with a regulatable promoter while still maintaining its immunogenicity. The live attenuated *Y. pseudotuberculosis* strains used as vectors to inject the LcrV antigen from *Y. pestis* via T3SS elicits both antibody responses and specific T-cell responses to LcrV of *Y. pestis*, resulting in enhanced protective immunity against plague. Another embodiment is a live attenuated *Y. pseudotuberculosis* strain with the caf operon inserted into its chromosome to synthesize F1 in a temperature-dependent manner, can enhance its immunogenicity.

BRIEF DESCRIPTION OF THE FIGURES

FIG. 1A depicts growth curves of mutant and parent strains. The growth curves of *Y. pseudotuberculosis* Y. pt PB1+, χ10052, χ10053 and χ10055 in LB medium supplemented with different amounts (0%, 0.05%, and 0.1%) of arabinose at 26° C. is shown.

FIG. 1B depicts LPS pheotypes. LPS was visualized by the use of silver-staining polyacrylamide gel electrophoresis (PAGE) gels. The strains (from left to right) are as follows: χ3761 (*Salmonella Typhimurium* UK-1), χ10013 (ΔlpxP *Y. pestis* KIM6+), wild-type *Y. pseudotuberculosis* PB1+ (Y. pt PB1+), χ10052 (ΔmsbB), χ10053 (ΔmsbB:: $P_{msbB}$ $msbB_{(EC)}$) and χ10055 (ΔmsbB::$P_{msbB}$ $msbB_{(EC)}$ $\Delta P_{crp}$::TT araC $P_{BAD}$ crp). All strains were cultured at 26° C. and 37° C.

FIG. 1C is a schematic diagram depicting the chromosomal structure of the wild-type parent PB1+ (top) and χ10057 (Δasd ΔmsbB::$P_{msbB}$ $msbB_{(EC)}$ $\Delta P_{crp}$::TT araC $P_{BAD}$ crp) (bottom). “L” means 26° C.; “H” means 37° C.

FIG. 2A depicts a physical map of pYA5199.

FIG. 2B The synthesis and secretion of $YopE_{Nt138}$-LcrV were determined in χ10057 (pYA5199) by western blotting. *Y. pestis* KIM6+ (no pCD1 plasmid) as negative control and χ10057 (pYA3332) as vector control;

FIG. 2C Translocation of $YopE_{Nt138}$-LcrV into cytosol of HeLa cells infected by χ10057 (pYA5199) was detected by enhanced chemiluminescent detection system. χ10006 (pYA5199) (Δasd *Y. pestis* KIM6+) was used as negative control and χ10057 (pYA3332) as vector control; Translocation of YopE and YopH as interior controls.

FIG. 3A depicts kinetics of bacterial burden in mice infected orally with *Y. pseudotuberculosis* PB1+ (●), χ10057 (pYA3332) (▼) or χ10057 (pYA5199) (□). Groups of mice were inoculated orally with 0.7×10$^9$ CFU of wild-type *Y. pseudotuberculosis* PB1+, 1.5×10$^9$ CFU of χ10057 (pYA3332) or 1.3×10$^9$ CFU of χ10057 (pYA5199). CFU per organ in Peyer’s patches from 3 mice per group were determined at various times (3, 6 and 9 days). Error bars represent standard deviations. *: P<0.05, : P<0.01, *: P<0.001, ns: not significant. The experiment was performed twice with similar results and the results were pooled for presentation.

FIG. 3B depicts kinetics of bacterial burden in mice infected orally with *Y. pseudotuberculosis* PB1+ (●), χ10057 (pYA3332) (▼) or χ10057 (pYA5199) (□). Groups of mice were inoculated orally with 0.7×10$^9$ CFU of wild-type *Y. pseudotuberculosis* PB1+, 1.5×10$^9$ CFU of χ10057 (pYA3332) or 1.3×10$^9$ CFU of χ10057 (pYA5199). CFU per organ in spleens from 3 mice per group were determined at various times (3, 6 and 9 days). Error bars represent standard deviations. *: P<0.05, : P<0.01, *: P<0.001, ns: not significant. The experiment was performed twice with similar results and the results were pooled for presentation.

FIG. 3C depicts kinetics of bacterial burden in mice infected orally with *Y. pseudotuberculosis* PB1+ (●), χ10057 (pYA3332) (▼) or χ10057 (pYA5199) (□). Groups of mice were inoculated orally with 0.7×10$^9$ CFU of wild-type *Y. pseudotuberculosis* PB1+, 1.5×10$^9$ CFU of χ10057 (pYA3332) or 1.3×10$^9$ CFU of χ10057 (pYA5199). CFU per organ in livers from 3 mice per group were determined at various times (3, 6 and 9 days). Error bars represent standard deviations. *: P<0.05, : P<0.01, *: P<0.001, ns: not significant. The experiment was performed twice with similar results and the results were pooled for presentation.

FIG. 4A depicts mouse survival after *Y. pestis* KIM6+ (pCD1Ap) challenge. Swiss Webster mice orally vaccinated with a dose of 2.0×10$^9$ CFU of χ10056 (pYA3332), 2.5×10$^9$ CFU of χ10056 (pYA5199) as plasmid control, 2.6×10$^9$ CFU of χ10057 (pYA3332), 2.2×10$^9$ CFU of χ10057 (pYA5199), with BSG as negative control or Swiss Webster mice subcutaneously immunized with 2.5×10$^7$ CFU of *Y. pestis* KIM6(pCD1Ap) (Pgm$^-$) as a standard attenuated *Y. pestis* vaccine. At days 35 after initial immunization, mice were challenged with 2.4×10$^4$ CFU of *Y. pestis* KIM6+ (pCD1Ap) via the i.n. route. Survival of immunized mice was significantly greater than PBS controls in all experiments (**, P<0.0001). Survival of mice immunized with χ10057 (pYA5199) was significantly greater than mice immunized with strain χ10056 (pYA3332), χ10056 (pYA5199), χ10057 (pYA3332) (*, P<0.001) and *Y. pestis* KIM5 (**, P<0.01).

FIG. 4B At days 35 after initial immunization, mice were challenged with 1.1×10$^5$ CFU of *Y. pestis* KIM6+ (pCD1Ap) via the s.c. route. Survival of mice immunized with χ10057 (pYA5199) was significantly greater than mice immunized with strain χ10057 (pYA3332) (**, P<0.01). In each experiment there were 10 mice in the vaccinated group and 5 mice in the control group. All experiments were performed twice with similar outcomes and the results were pooled for presentation.

FIG. 5A depicts antibody responses in sera and vaginal washes of mice immunized with BSG, χ10057 (pYA3332) or χ10057 (pYA5199). Total IgG response to *Y. pestis* KIM5+ whole cell lysate (YpL) is shown.

FIG. 5B depicts antibody responses in sera and vaginal washes of mice immunized with BSG, χ10057 (pYA3332) or χ10057 (pYA5199). Total IgG response to recombinant LcrV is shown.

FIG. 5C depicts antibody responses in sera and vaginal washes of mice immunized with BSG, χ10057 (pYA3332) or χ10057 (pYA5199). The secretory IgA in vaginal washes response to LcrV. The sera and vaginal washes from 12 mice were individually analyzed and the experiments were performed twice with consistent results. *, P<0.05; : P<0.01, *: P<0.001.

FIG. 6A depicts serum IgG1 and IgG2a responses to YpL and recombinant LcrV. IgG1 and IgG2a antibody levels to YpL in sera of mice orally immunized with χ10057

(pYA3332). The sera from 12 mice were individually analyzed and the experiments were performed twice with consistent results. *, P<0.05.

Figure 7A:
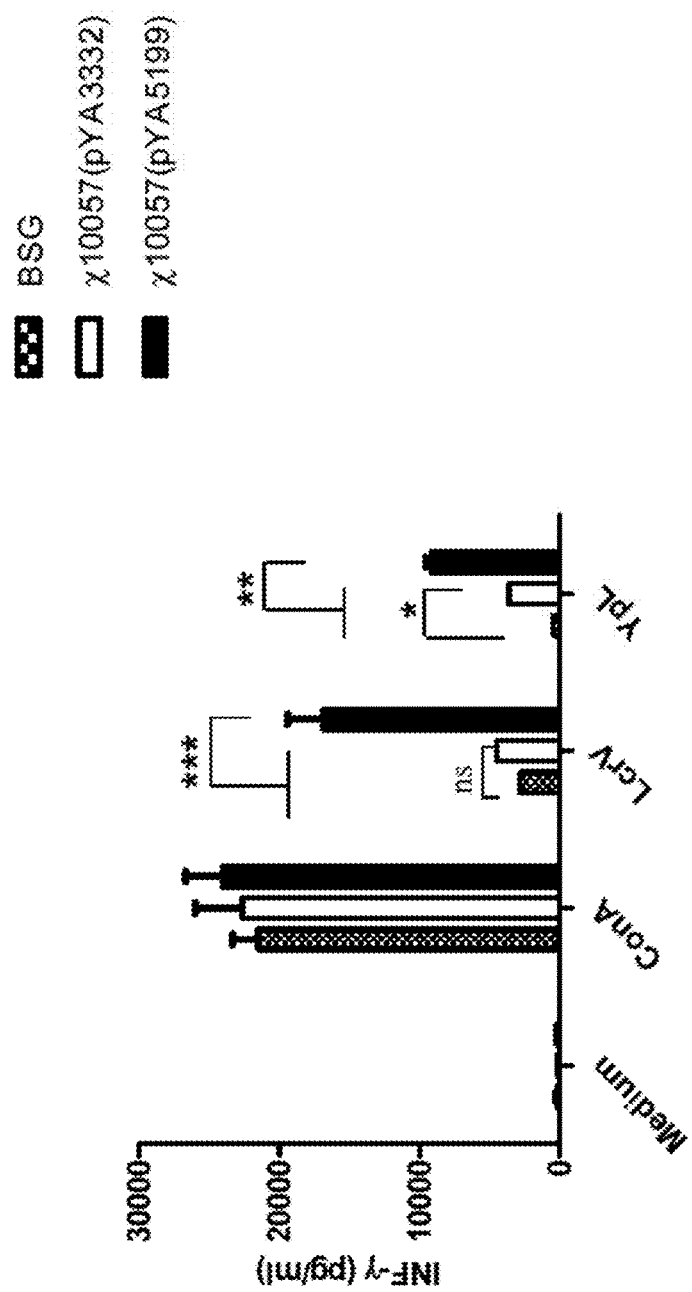

FIG. 7A depicts production of IFN-γ in mice immunized with a live attenuated *Y. pseudotuberculosis* strain. Splenocytes isolated from Swiss Webster mice vaccinated orally with strains χ10057 (pYA3332, vector control), χ10057 (pYA5199, yopE$_{Nt138}$-lcrV) or BSG at 21 days after initial immunization were stimulated in vitro with 4 μg/ml of either a purified LcrV or YpL. The mitogen Concanavalin A (ConA: 1 μg/ml) served as positive controls and RPMI 1640 media used as negative controls. Antigen-specific IFN-γ, cytokines in the culture supernatants produced from splenic cells after 3 days stimulation were measured by Bioplex assays. The mean±SE was composed of 8 mice for each experiment (two experiments were pooled together). *: P<0.05, : P<0.01, *: P<0.001, ns: not significant.

Figure 7B:
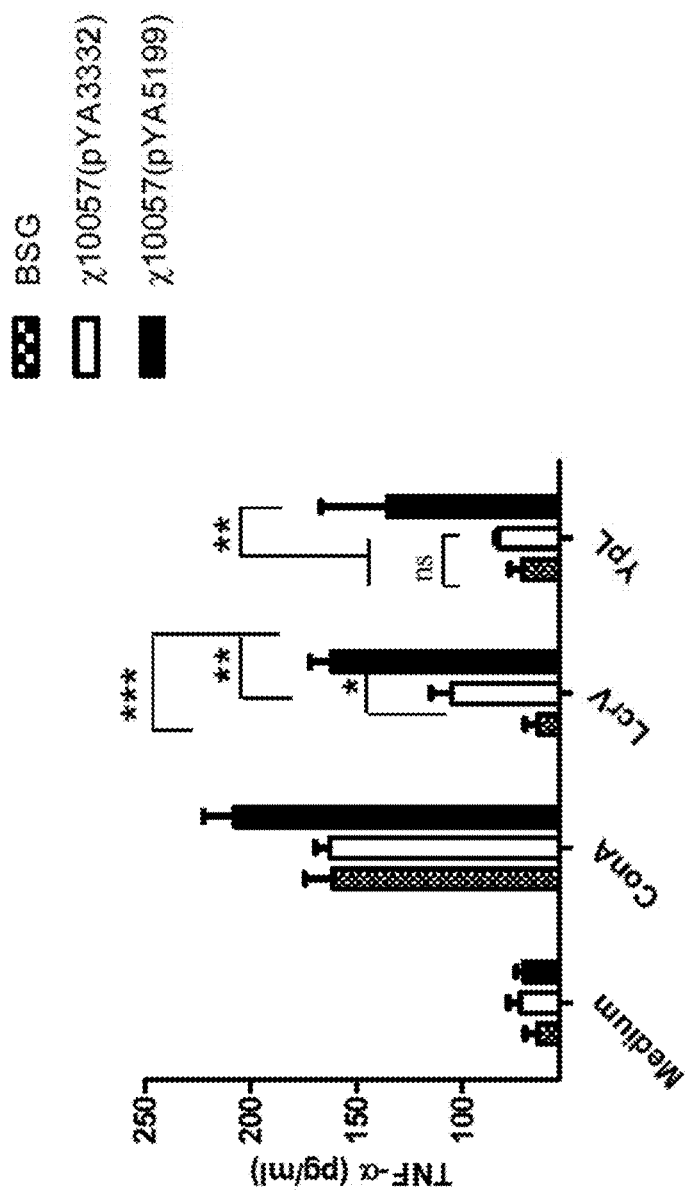

FIG. 7B depicts production of TNF-α in mice immunized with a live attenuated *Y. pseudotuberculosis* strain. Splenocytes isolated from Swiss Webster mice vaccinated orally with strains χ10057 (pYA3332, vector control), χ10057 (pYA5199, yopE$_{Nt138}$-lcrV) or BSG at 21 days after initial immunization were stimulated in vitro with 4 μg/ml of either a purified LcrV or YpL. The mitogen Concanavalin A (ConA: 1 μg/ml) served as positive controls and RPMI 1640 media used as negative controls. Antigen-specific TNF-α cytokines in the culture supernatants produced from splenic cells after 3 days stimulation were measured by Bioplex assays The mean±SE was composed of 8 mice for each experiment (two experiments were pooled together). *: P<0.05, : P<0.01, *: P<0.001, ns: not significant.

Figure 7C:
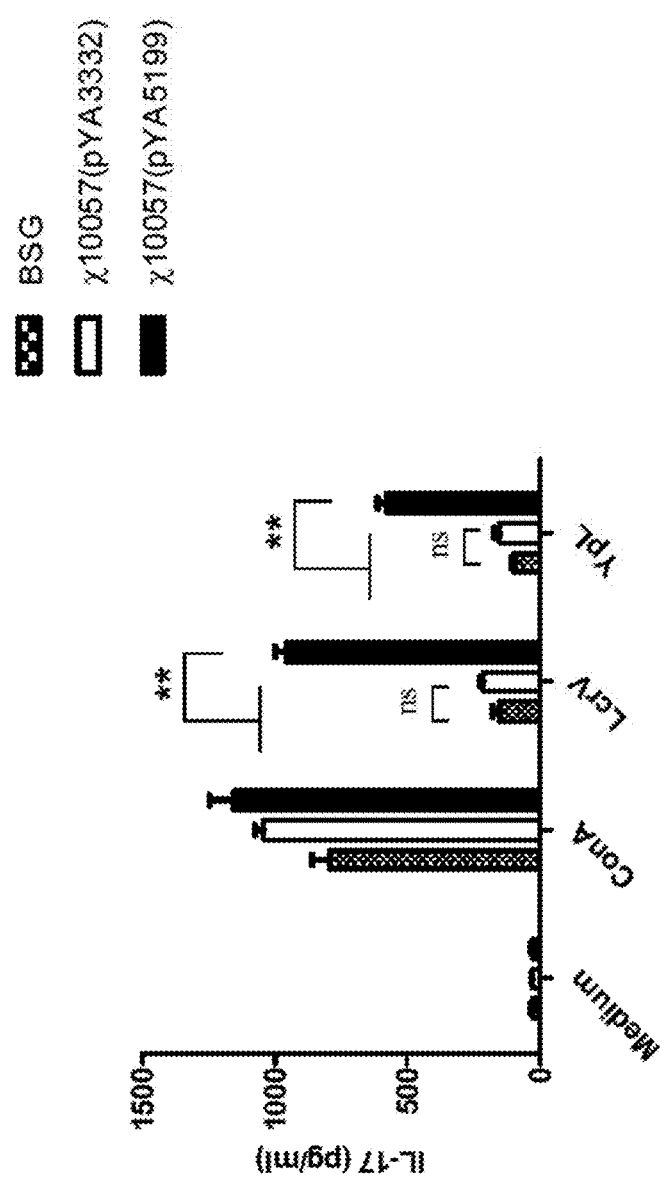

FIG. 7C depicts production of IL-17 in mice immunized with a live attenuated *Y. pseudotuberculosis* strain. Splenocytes isolated from Swiss Webster mice vaccinated orally with strains χ10057 (pYA3332, vector control), χ10057 (pYA5199, yopE$_{Nt138}$-lcrV) or BSG at 21 days after initial immunization were stimulated in vitro with 4 μg/ml of either a purified LcrV or YpL. The mitogen Concanavalin A (ConA: 1 μg/ml) served as positive controls and RPMI 1640 media used as negative controls. Antigen-specific IL-17 cytokines in the culture supernatants produced from splenic cells after 3 days stimulation were measured by Bioplex assays The mean±SE was composed of 8 mice for each experiment (two experiments were pooled together). *: P<0.05, : P<0.01, *: P<0.001, ns: not significant.

Figure 8:
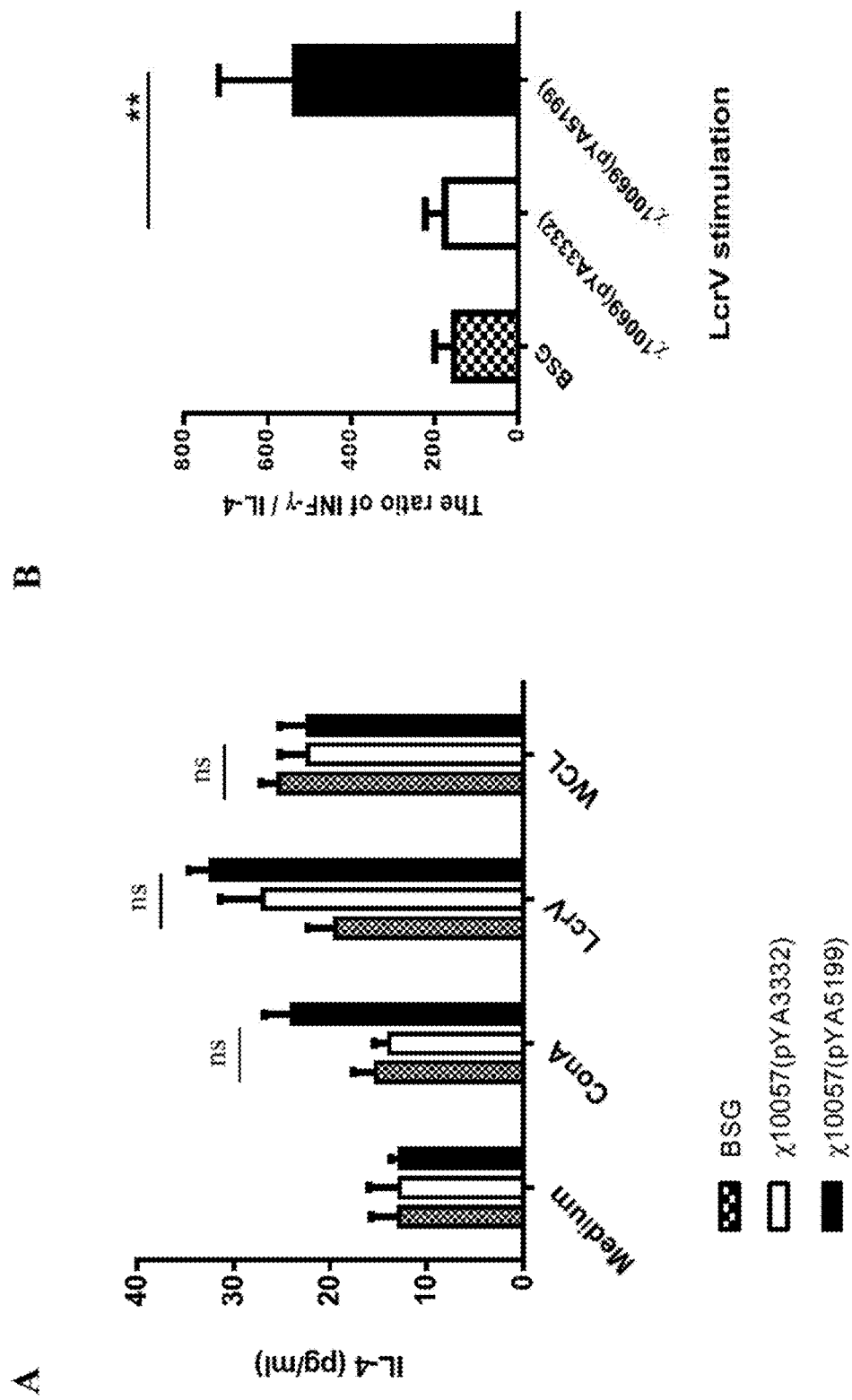

FIG. 8 depicts antigen-specific IL-4 cytokine in the culture supernatants produced from splenic cells and the ratio of INF-γ with IL-4. Splenocytes isolated from Swiss Webster mice vaccinated orally with strains χ10057 (pYA3332, vector control), χ10057 (pYA5199, yopE$_{Nt138}$-lcrV) or BSG at 21 days after initial immunization were stimulated in vitro with 4 μg/ml of either a purified LcrV or YpL. The mitogen Concanavalin A (ConA: 1 μg/ml) served as positive controls and RPMI 1640 media used as negative controls. (A) Antigen-specific IL-4 cytokine in the culture supernatants produced from splenic cells after 3 days stimulation was measured by Bioplex assays. (B) The ratio of INF-γ with IL-4. The mean±SE was composed of 8 mice for each experiment (two experiments were pooled together). **: P<0.001, ns: not significant.

Figure 9:
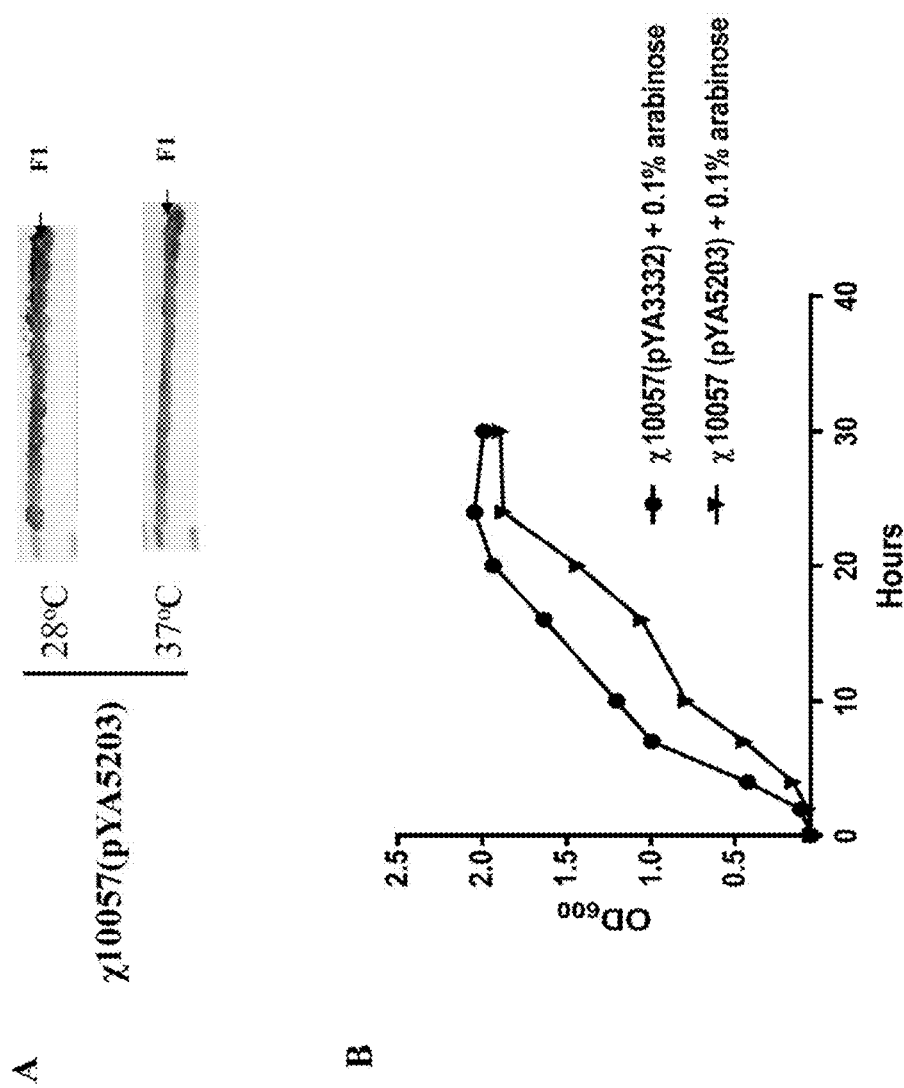

FIG. 9 depicts F1 synthesis of χ10057 (pYA5203) at 28° C. and 37° C. and growth of χ10057 (pYA3332) and χ10057 (pYA5203). (A) χ10057 (pYA5203) cultured in LB medium supplemented with 0.1% of arabinose synthesized high-level F1 at 28° C. and 37° C.; (B) The growth of χ10057 (pYA5203) was compared with that of χ10057 (pYA3332) at 28° C. in LB medium supplemented with 0.1% of arabinose.

Figure 10A:
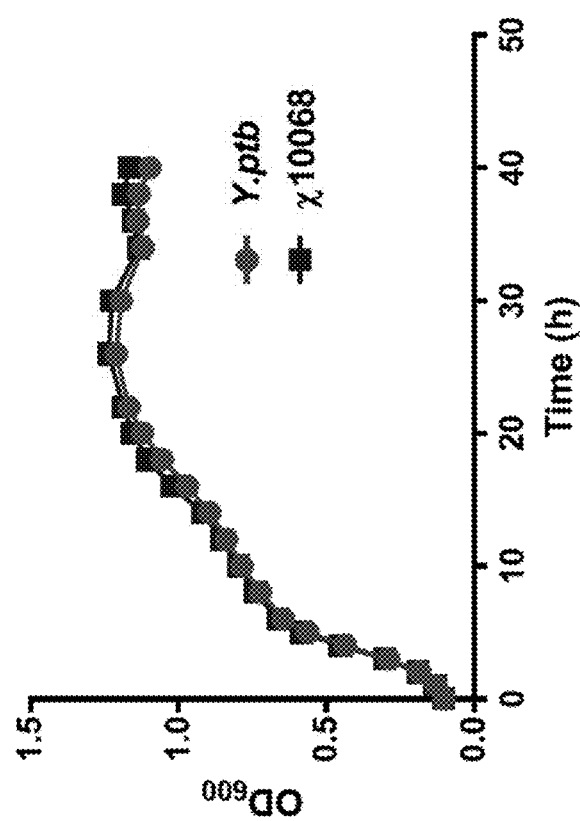

FIG. 10A depicts optimal growth conditions for mutant strain χ10068 to maximize F1 synthesis. The growth rate of attenuated χ10068 was the same as wild-type Yptb when grown at 28° C. in HIB.

Figure 10B:
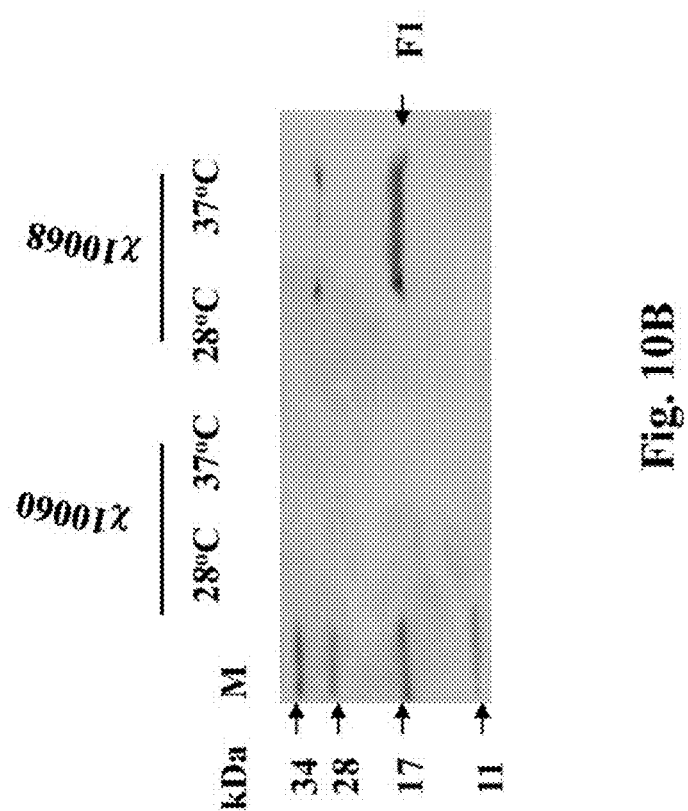

FIG. 10B depicts optimal growth conditions for mutant strain χ10068 to maximize F1 synthesis. F1 was synthesized in χ10068 cultured at 28° C. and 37° C., but not in χ10060.

Figure 10C:
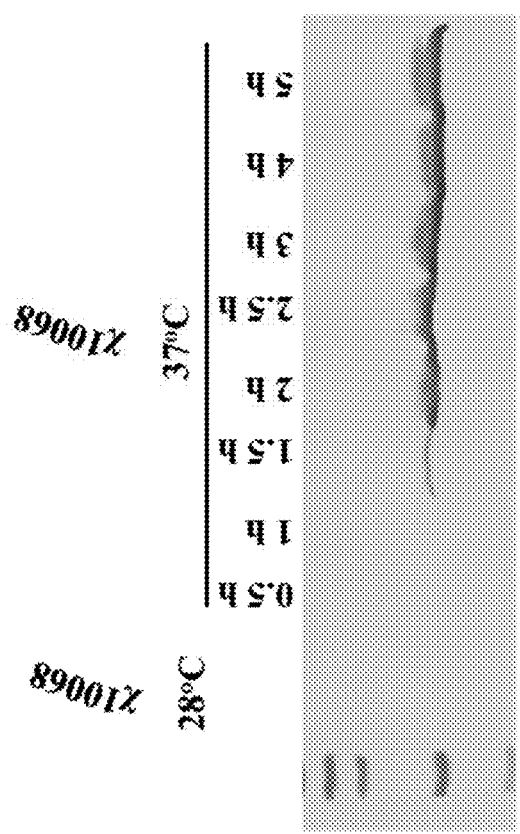

FIG. 10C depicts optimal growth conditions for mutant strain χ10068 to maximize F1 synthesis. F1 synthesis in χ10068 at 28° C. and switched to 37° C. at different times.

Figure 11A:
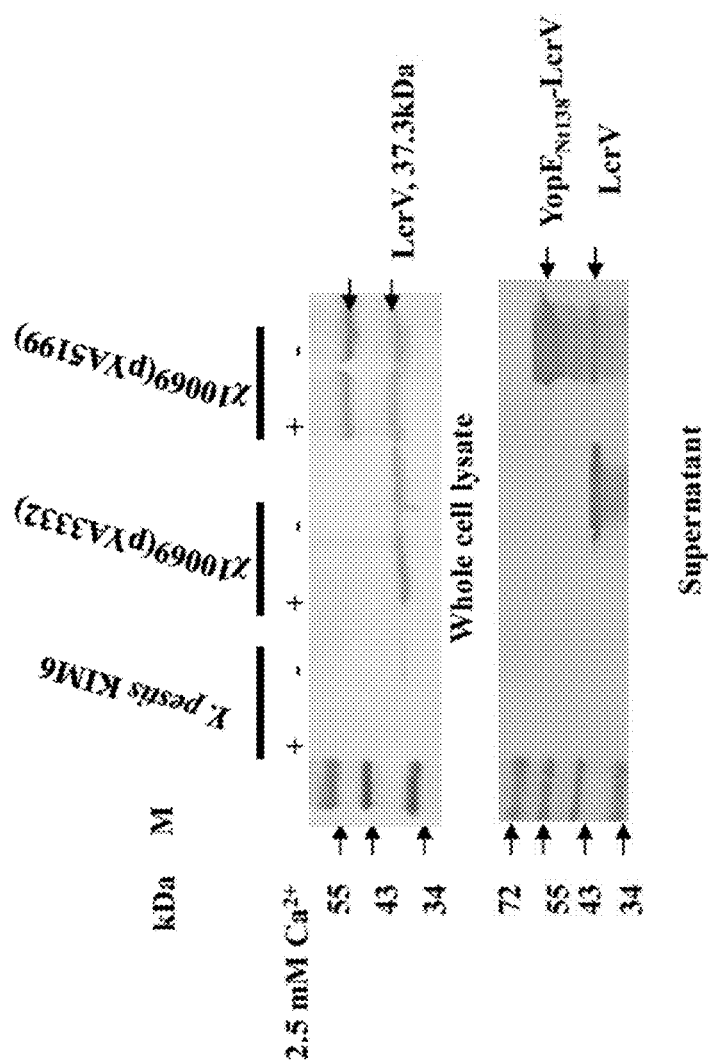

FIG. 11A depicts secretion and translocation of YopE$_{Nt138}$-LcrV by χ10069 (pYA5199) and growth of bacteria. The synthesis and secretion into the supernatant fluid of YopE$_{Nt138}$-LcrV were determined in χ10069 (pYA5199) by western blotting.

Figure 11B:
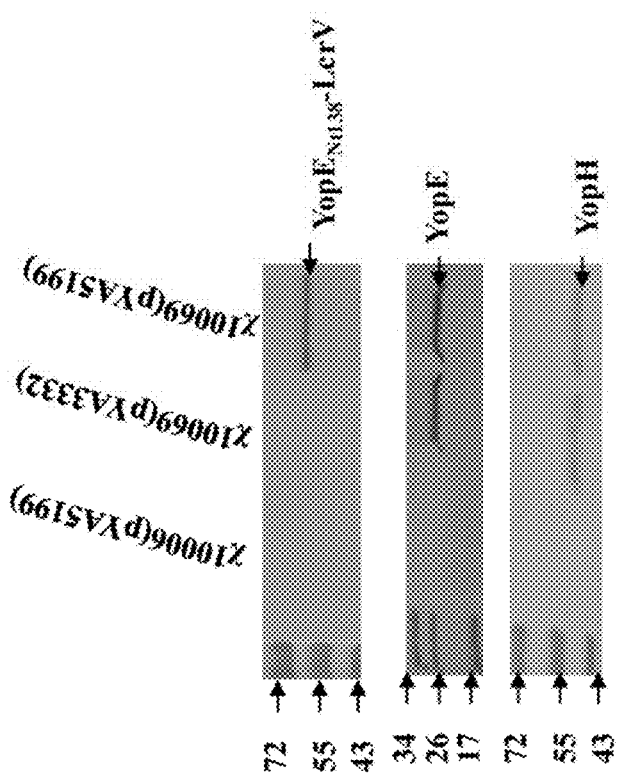

FIG. 11B depicts secretion and translocation of YopE$_{Nt138}$-LcrV by χ10069 (pYA5199) and growth of bacteria. The YopE$_{Nt138}$-LcrV translocation into cytosol of HeLa cells infected by χ10069 (pYA5199) was also detected by western blotting.

Figure 11C:
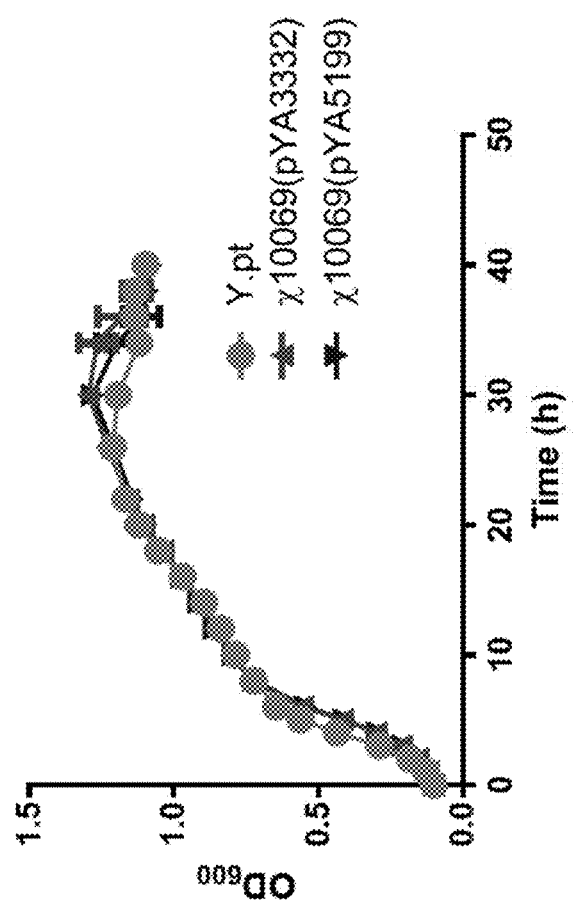

FIG. 11C depicts secretion and translocation of YopE$_{Nt138}$-LcrV by χ10069 (pYA5199) and growth of bacteria. The growth rates of attenuated χ10069 (pYA3332) and χ10069 (pYA5199) were the same as wild-type Yptb when grown at 28° C. in HIB.

Figure 12A:
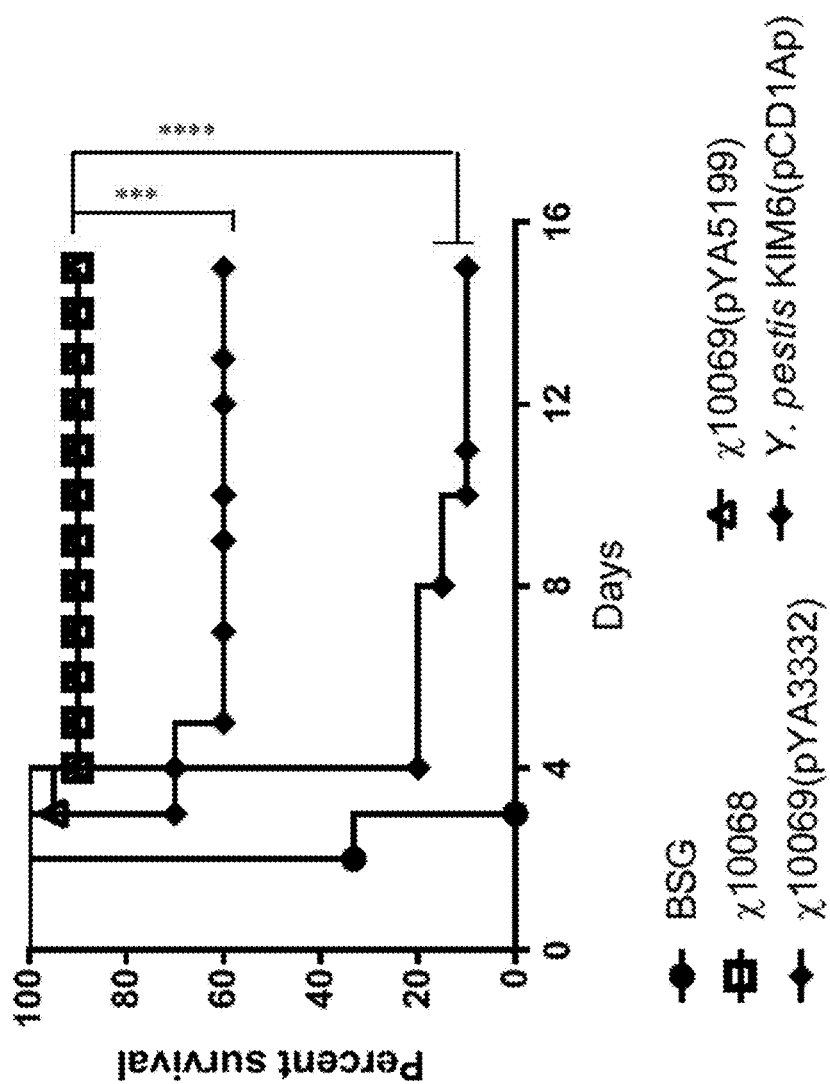

FIG. 12A depicts mouse survival after *Y. pestis* KIM6+ (pCD1Ap) challenge. Swiss Webster mice orally vaccinated with a dose of $1.6 \times 10^9$ CFU of χ10068, $2.0 \times 10^9$ CFU of χ10069 (pYA3332) as plasmid control, $3.0 \times 10^9$ CFU of χ10069 (pYA5199) or BSG as negative control. Swiss Webster mice subcutaneously immunized with $2.0 \times 10^7$ CFU of *Y. pestis* KIM6(pCD1Ap) (Pgm$^-$) as a standard attenuated *Y. pestis* vaccine. At days 35 after initial immunization, mice were challenged with $5.0 \times 10^4$ CFU of *Y. pestis* KIM6+ (pCD1Ap) via the i.n. route. Survival of mice immunized with χ10068 or χ10069 (pYA5199) was significantly greater than mice immunized with *Y. pestis* KIM6(pCD1Ap) (Pgm$^-$) (*, P<0.001), strain χ10069 (pYA3332) or BSG (**, P<0.0001). In each experiment there were 10 mice in the vaccinated group and 5 mice in BSG control group. All experiments were performed twice with similar outcomes and the results were pooled for presentation.

Figure 12B:
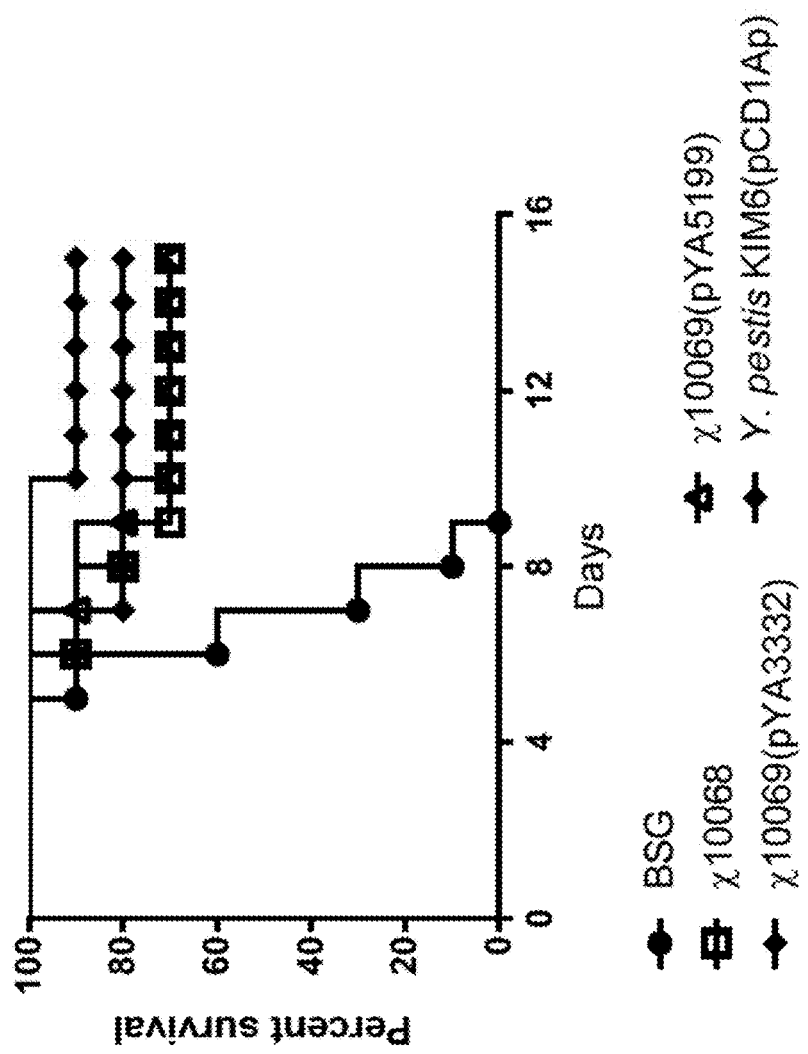

FIG. 12B depicts mouse survival after *Y. pestis* KIM6+ (pCD1Ap) challenge. Swiss Webster mice orally vaccinated with a dose of $1.6 \times 10^9$ CFU of χ10068, $2.0 \times 10^9$ CFU of χ10069 (pYA3332) as plasmid control, $3.0 \times 10^9$ CFU of χ10069 (pYA5199) or BSG as negative control. Swiss Webster mice subcutaneously immunized with $2.0 \times 10^7$ CFU of *Y. pestis* KIM6(pCD1Ap) (Pgm$^-$) as a standard attenuated *Y. pestis* vaccine. At days 35 after initial immunization, mice were challenged with $2.3 \times 10^6$ CFU of *Y. pestis* KIM6+ (pCD1Ap) via the s.c. route. No significant difference among χ10068, χ10069 (pYA3332), or χ10069 (pYA5199). In each experiment there were 10 mice in the vaccinated group and 5 mice in BSG control group. All experiments were performed twice with similar outcomes and the results were pooled for presentation.

Figure 13A:
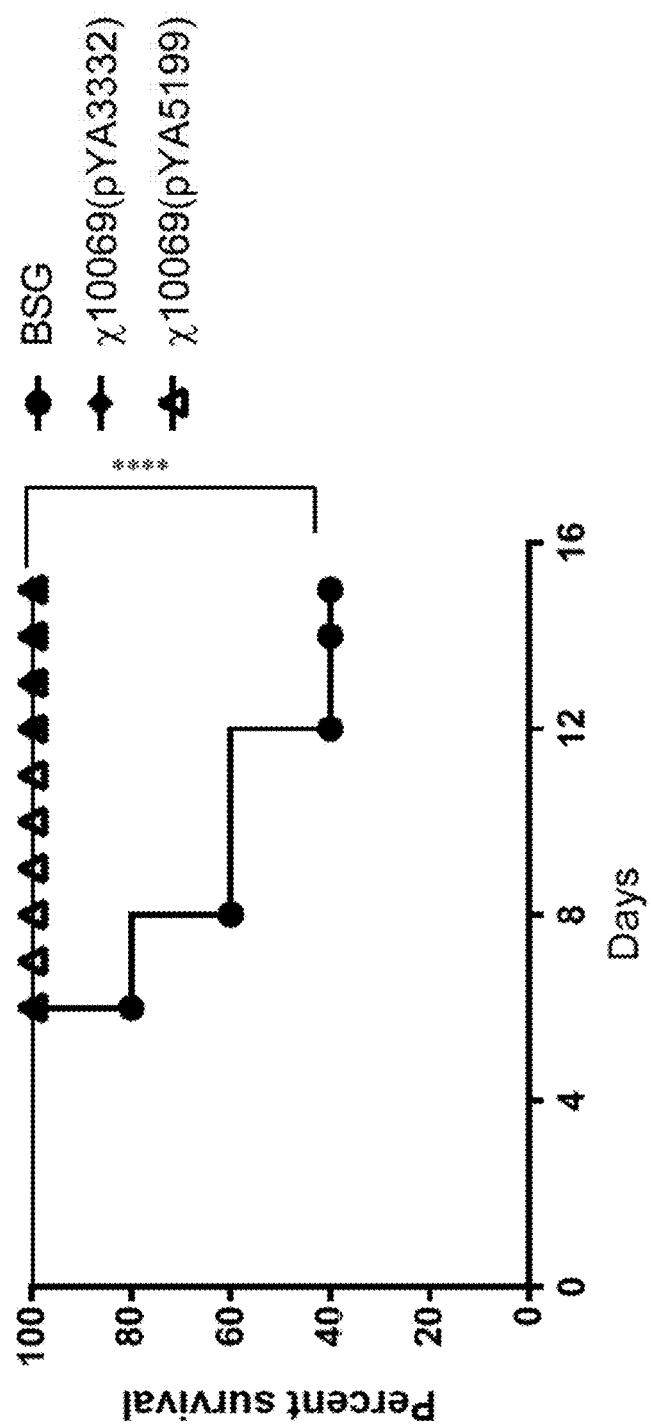

FIG. 13A depicts mouse survival after *Y. enterocolitic* WA and *Y. pseudotuberculosis* PB1+ challenge. Swiss Webster mice orally vaccinated with a dose of $1.53\times10^9$ CFU of χ10069 (pYA3332) as plasmid control, $1.45\times10^9$ CFU of χ10069 (pYA5199) or BSG as negative control. At 35 days after initial vaccination, mice were orally challenged with $2.4\times10^9$ CFU of *Y. enterocolitic* WA. Survival of mice immunized with χ10069 (pYA3332) χ10069 (pYA5199) was no difference but significantly greater than mice immunized with strain or BSG (****, P<0.0001). In each experiment there were 10 mice in the vaccinated group and 5 mice in BSG control group.

FIG. 13B depicts mouse survival after *Y. enterocolitic* WA and *Y. pseudotuberculosis* PB1+ challenge. Swiss Webster mice orally vaccinated with a dose of $1.53\times10^9$ CFU of χ10069 (pYA3332) as plasmid control, $1.45\times10^9$ CFU of χ10069 (pYA5199) or BSG as negative control. (B) At 35 days after initial vaccination, mice were orally challenged with CFU of *Y. pseudotuberculosis* PB1+. Survival of mice immunized with χ10069 (pYA5199) was significantly greater than mice immunized with strain χ10069 (pYA3332) or BSG (****, P<0.0001). In each experiment there were 10 mice in the vaccinated group and 5 mice in BSG control group.

FIG. 14A depicts humoral and cellular immune responses to LcrV in mice immunized with χ10068, χ10069 (pYA3332, vector control), χ10069 (pYA5199, $yopE_{Nt138}$-lcrV), or BSG. Antigen-specific IFN-γ and IL-17 in the culture supernatants produced from spleen cells after 3 days stimulation by LcrV were measured by ELISA. The mean was generated from 8 mice (two experiments were pooled together). *: P<0.05, ***: P<0.001, ns: not significant.

FIG. 14B depicts humoral and cellular immune responses to LcrV in mice immunized with χ10068, χ10069 (pYA3332, vector control), χ10069 (pYA5199, $yopE_{Nt138}$-lcrV), or BSG. Antigen-specific IFN-γ and IL-17 in the culture supernatants produced from spleen cells after 3 days stimulation by LcrV were measured by ELISA. The mean was generated from 8 mice (two experiments were pooled together). *: P<0.05, ***: P<0.001, ns: not significant.

FIG. 14C depicts humoral and cellular immune responses to LcrV in mice immunized with χ10068, χ10069 (pYA3332, vector control), χ10069 (pYA5199, $yopE_{Nt138}$-lcrV), or BSG. Antigen-specific IFN-γ and IL-17 in the culture supernatants produced from spleen cells after 3 days stimulation by LcrV were measured by ELISA. The mean was generated from 8 mice (two experiments were pooled together). *: P<0.05, ***: P<0.001, ns: not significant.

FIG. 15A depicts humoral and cellular immune responses to F1 in mice immunized with χ10068 or BSG. Antigen-specific IFN-γ and IL-17 in the culture supernatants produced from spleen cells after 3 days stimulation by F1 were measured by ELISA. The mean was generated from 8 mice (two experiments were pooled together). *: P<0.05, ***: P<0.001, ns: not significant.

FIG. 15B depicts humoral and cellular immune responses to F1 in mice immunized with χ10068 or BSG. Antigen-specific IFN-γ and IL-17 in the culture supernatants produced from spleen cells after 3 days stimulation by F1 were measured by ELISA. The mean was generated from 8 mice (two experiments were pooled together). *: P<0.05, ***: P<0.001, ns: not significant.

FIG. 15C depicts humoral and cellular immune responses to F1 in mice immunized with χ10068 or BSG. Antigen-specific IFN-γ and IL-17 in the culture supernatants produced from spleen cells after 3 days stimulation by F1 were measured by ELISA. The mean was generated from 8 mice (two experiments were pooled together). *: P<0.05, ***: P<0.001, ns: not significant.

FIG. 16A. Kinetics of bacterial burden in mice infected orally with *Y. pseudotuberculosis* PB1+ (●), χ10068 (▼). Groups of mice were inoculated orally with $1.2\times10^9$ CFU of wild-type *Y. pseudotuberculosis* PB1+, $1.3\times10^9$ CFU of χ10068. CFU per organ in Peyer's patches from 3 mice per group were determined at various times (3, 6 and 9 days). Error bars represent standard deviations. *: P<0.05, : P<0.01, *: P<0.001. The experiment was performed twice and data was combined together.

FIG. 16B. Kinetics of bacterial burden in mice infected orally with *Y. pseudotuberculosis* PB1+ (●), χ10068 (▼). Groups of mice were inoculated orally with $1.2\times10^9$ CFU of wild-type *Y. pseudotuberculosis* PB1+, $1.3\times10^9$ CFU of χ10068. CFU per organ in spleens from 3 mice per group were determined at various times (3, 6 and 9 days). Error bars represent standard deviations. *: P<0.05, : P<0.01, *: P<0.001. The experiment was performed twice and data was combined together.

FIG. 16C. Kinetics of bacterial burden in mice infected orally with *Y. pseudotuberculosis* PB1+ (●), χ10068 (▼). Groups of mice were inoculated orally with $1.2\times10^9$ CFU of wild-type *Y. pseudotuberculosis* PB1+, $1.3\times10^9$ CFU of χ10068. CFU per organ in livers from 3 mice per group were determined at various times (3, 6 and 9 days). Error bars represent standard deviations. *: P<0.05, : P<0.01, *: P<0.001. The experiment was performed twice and data was combined together.

FIG. 17A. Frequency of antigen specific T cells in vitro. Percentage of T cells positive for CD4+ IFN-γ+ and CD8+ IFN-γ+ out of all T-lymphocytes was determined by FACS analysis. Splenocytes isolated from Swiss Webster mice vaccinated orally with strains χ10068 or BSG at 28 days after initial immunization were restimulated in vitro with 4 mg/ml of either a purified F1 or YpL. The PMA (20 ng/ml) plus ionomycin (1 μg/ml) served as positive controls and RPMI 1640 media used as negative controls. The cells stained with CD4− phycoerythrin (PE) (clone RM4-5), CD8-allophycocyanin (APC) (clone 53-6.7) and then intracelullarly stained with IFN-γ− fluorescein isothiocyanate (FITC) (clone XMG1.2) will be analyzed by Flow cytometry. Portion of CD4+IFN-γ+ T cells is shown is this FIG. 17A. The mean±SD was composed of 4 mice for each experiment (two experiments were pooled together). *: P<0.05, **: P<0.01, ns: not significant.

FIG. 17B. Frequency of antigen specific T cells in vitro. Percentage of T cells positive for CD4+IFN-γ+ and CD8+ IFN-γ+ out of all T-lymphocytes was determined by FACS analysis. Splenocytes isolated from Swiss Webster mice vaccinated orally with strains χ10068 or BSG at 28 days after initial immunization were restimulated in vitro with 4 mg/ml of either a purified F1 or YpL. The PMA (20 ng/ml) plus ionomycin (1 μg/ml) served as positive controls and RPMI 1640 media used as negative controls. The cells stained with CD4− phycoerythrin (PE) (clone RM4-5), CD8-allophycocyanin (APC) (clone 53-6.7) and then intracelullarly stained with IFN-γ− fluorescein isothiocyanate (FITC) (clone XMG1.2) will be analyzed by Flow cytometry. Portion of CD8+IFN-γ+ T cells is shown is this FIG. 17B. The mean±SD was composed of 4 mice for each experiment (two experiments were pooled together). *: P<0.05, **: P<0.01, ns: not significant.

Figure 17A:
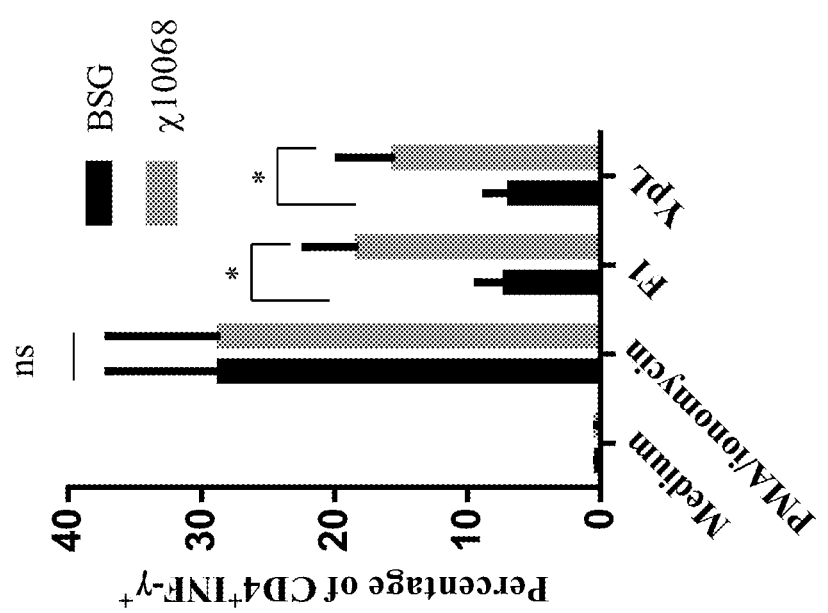
Figure 17B:
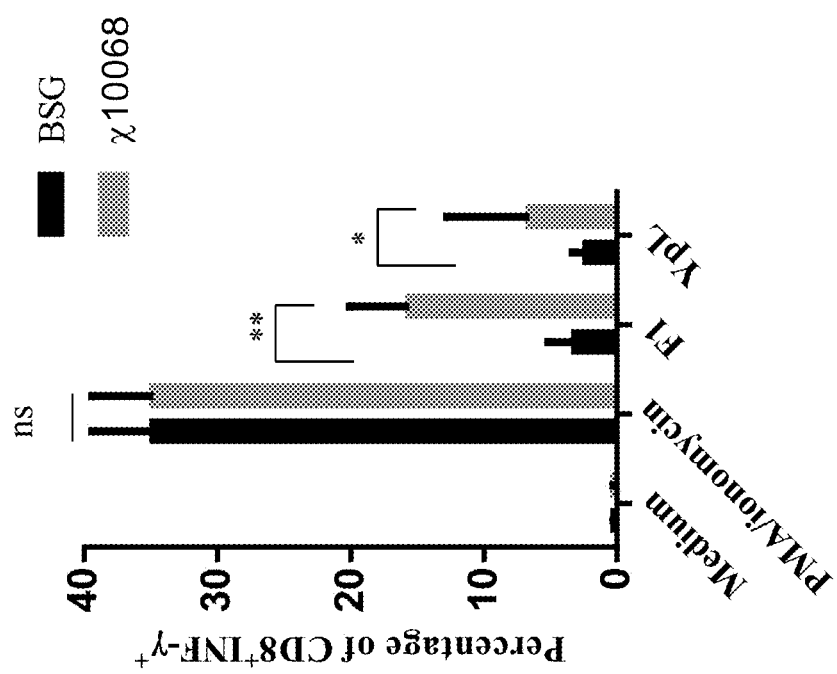
Figure 17C:
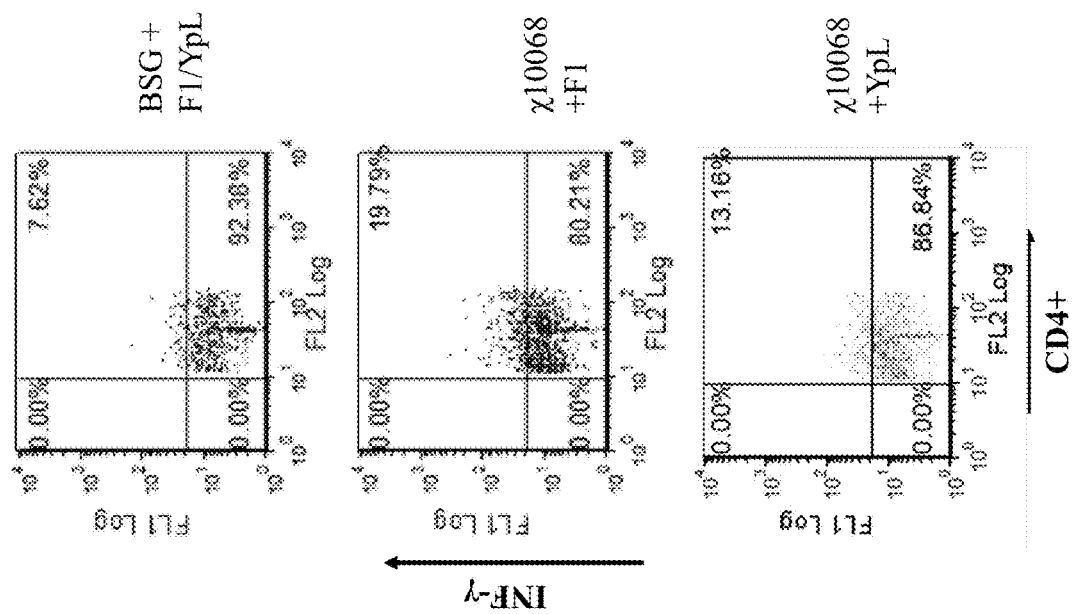

FIG. 17C. Frequency of antigen specific T cells in vitro. Percentage of T cells positive for CD4+ IFN-γ+ and CD8+ IFN-γ+ out of all T-lymphocytes was determined by FACS analysis. Splenocytes isolated from Swiss Webster mice vaccinated orally with strains χ10068 or BSG at 28 days after initial immunization were restimulated in vitro with 4 mg/ml of either a purified F1 or YpL. The PMA (20 ng/ml) plus ionomycin (1 μg/ml) served as positive controls and RPMI 1640 media used as negative controls. The cells stained with CD4− phycoerythrin (PE) (clone RM4-5), CD8-allophycocyanin (APC) (clone 53-6.7) and then intracelullarly stained with IFN-γ− fluorescein isothiocyanate (FITC) (clone XMG1.2) will be analyzed by Flow cytometry. Representative flow cytometry analysis for double staining with CD4+ and IFN-γ+ is shown is this FIG. 17C. The mean±SD was composed of 4 mice for each experiment (two experiments were pooled together). *: P<0.05, **: P<0.01, ns: not significant.

Figure 17D:
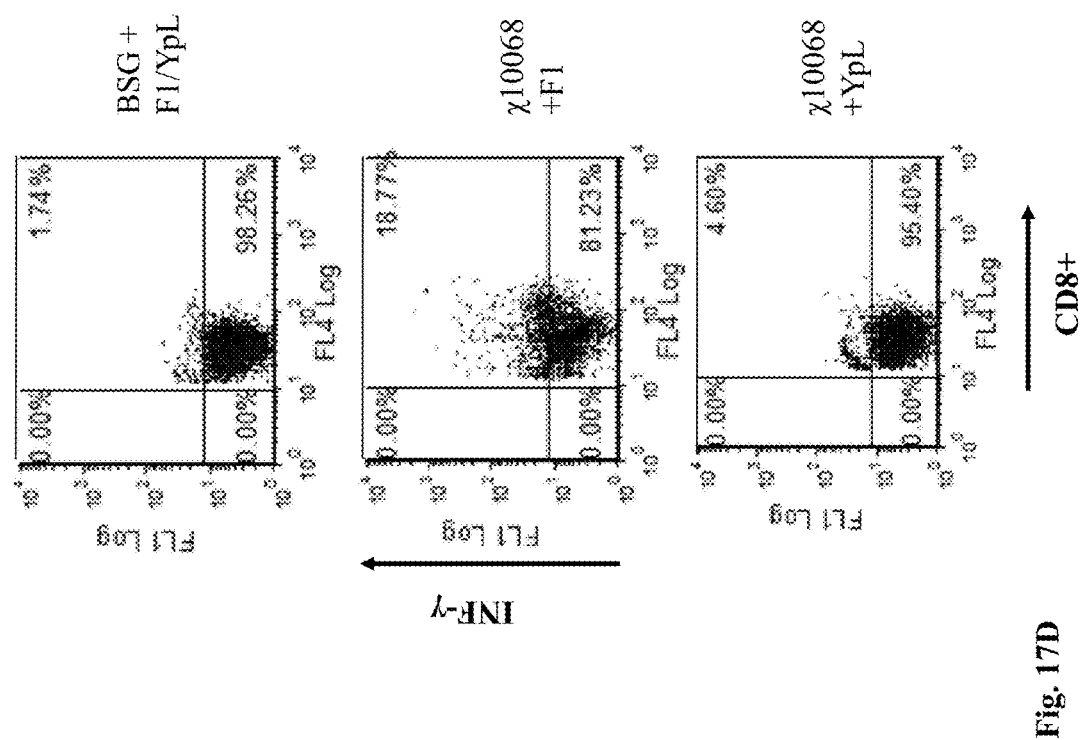

FIG. 17D. Frequency of antigen specific T cells in vitro. Percentage of T cells positive for CD4+IFN-γ+ and CD8+ IFN-γ+ out of all T-lymphocytes was determined by FACS analysis. Splenocytes isolated from Swiss Webster mice vaccinated orally with strains χ10068 or BSG at 28 days after initial immunization were restimulated in vitro with 4 mg/ml of either a purified F1 or YpL. The PMA (20 ng/ml) plus ionomycin (1 μg/ml) served as positive controls and RPMI 1640 media used as negative controls. The cells stained with CD4− phycoerythrin (PE) (clone RM4-5), CD8-allophycocyanin (APC) (clone 53-6.7) and then intracelullarly stained with IFN-γ− fluorescein isothiocyanate (FITC) (clone XMG1.2) will be analyzed by Flow cytometry. Representative flow cytometry analysis for double staining with CD8+ and IFN-γ+ is shown is this FIG. 17D. The mean±SD was composed of 4 mice for each experiment (two experiments were pooled together). *: P<0.05, **: P<0.01, ns: not significant.

DETAILED DESCRIPTION

The present disclosure provides a recombinant *Y. pseudotuberculosis* bacterium. The bacterium may be used to induce a protective immune response in mice. In particular, the bacterium may be used to induce an immune response to more than one pathogen. For instance, the bacterium may be used to induce an immune response to one or more of the pathogens *Y. pestis, Y. enterocolitica*, and *Y. pseudotuberculosis*. Advantageously, the bacterium may be used as a bait vaccine to control plague transmission in wildlife and prevent Yersiniosis in farm animals and humans.

Live *Yersinia* vaccines offer several advantages over recombinant vaccines. Their high antigenic complexity guarantees a response against a broad range of antigenic targets.

Additionally, they are often less expensive to manufacture than subunit vaccines (Sun et al., 2011). Thus, plague vaccines based on live attenuated *Yersinia* spp. provide the theoretical advantage of simultaneously priming immunity against many antigens, thereby reducing the likelihood of antigen circumvention by clever terrorists (Smiley, 2008b).

*Y. pseudotuberculosis*, sometimes abbreviated as Yptb, is thought to be the direct evolutionary ancestor of *Y. pestis* (Wren, 2003, Skurnik et al., 2000, Achtman et al., 1999). The two species diverged from one another 2,600-28,000 years ago (Morelli et al., Achtman et al., 1999, Achtman et al., 2004). But *Y. pseudotuberculosis* is much less virulent and typically causes an enteric disease in humans and animals. Its infections are self-limiting with a low case-fatality rate and its lifestyle as an enteric pathogen will facilitate its use as an oral vaccine. With the exception of two additional plasmids carried by *Y. pestis* (pPCP1 and pMT1), the two species share >95% genetic identity and a common virulence plasmid with a conserved colinear backbone (Chain et al., 2004). Blast analysis of several major *Y. pestis* antigens shows that LcrV shares 96% amino acid identity between the two species, Psn and YadC, two additional antigens shown to be protective against *Y. pestis* challenge (Branger et al., 2007, Murphy et al., 2007, Sun et al., 2014) share 100% (Buchrieser et al., 1999) and >97% (Forman et al., 2008), respectively, homology. Furthermore, *Y. pseudotuberculosis* has a much lower number of insertion sequence (IS) copies compared with *Y. pestis* and so is genetically much more stable than the later (Chain et al., 2004).

Previous studies suggest that *Y. pseudotuberculosis* is a promising candidate as an oral live carrier vaccine, capable of stimulating antigen specific CD8+ T cell responses (Russmann et al., 2003, Wiedig et al., 2005). Additionally, delivery of heterologous antigens by the T3 SS in *Y. pseudotuberculosis* and *Salmonella* stimulated antigen-specific cytotoxic T-cell responses, antigen-specific CD8$^+$ memory T cells, and protection against challenge with different pathogens (Lotter, 2004, Russmann et al., 2001, Russmann et al., 2003). Studies have indicated that both humoral and cellular immunity contribute to vaccine efficacy against plague (Williamson, 2009, Smiley, 2008b, Parent et al., 2005, Parent et al., 2006, Philipovskiy & Smiley, 2007, Smiley, 2008a). CD8+ T-cell immune responses primed to LcrV appear to confer protection against *Y. pestis* in mice (Wang et al., 2011b, Shreewastav et al., 2012).

Studies demonstrated that Chinese-origin rhesus macaques immunized with EV76 or mice immunized with the *Y. pestis* AsmpB-ssrA mutant primed a higher anti-F1 IgG titer but an almost undetectable titer to LcrV antigen (Qiu et al., 2010, Okan et al., 2010), which are consistent with other studies of animals immunized with the EV76 or KWC vaccine (Williamson et al., 1995c, Qi et al., 2010, Williamson et al., 2000, Williamson et al., 1997, Williamson et al., 1999, Quenee et al., 2008, Braciale et al., 2008). Mice vaccinated with *Y. pestis* KIM5 (pgm−) generated the CD4 and CD8 T cells that synergistically conferred protection against plague, but T cells from those vaccinated mice could not recognize LcrV (Philipovskiy & Smiley, 2007). Plague recovered patients also barely produced memory T cell responses to LcrV antigens (Li et al., 2012). Pettersson et al. analyzed the localization of LcrV during infection of HeLa cells and were unable to detect any LcrV in the cytosol of the cells (Pettersson et al., 1999). Nilles et al. suggested that this translocation appears to not be injection by T3SS, although small amounts of LcrV were detected in HeLa cells (Nilles et al., 1998). So based on these findings, we hypothesize that a live attenuated *Y. pseudotuberculosis* used as a vector to inject the LcrV antigen from *Y. pestis* via T3SS might prime both antibody responses and specific T-cell responses to LcrV, resulting in enhanced protective immunity against plague.

In this disclosure, we have constructed recombinant *Y. pseudotuberculosis* strains. Typically, the bacterium is derived from a *Y. pseudotuberculosis* strain, χ10051. Alternatively, a bacterium of the invention may be a strain listed in Table 1.

Several *Yersinia* species are suitable for use in the compositions and methods described herein. In one embodiment, a recombinant *Yersinia* bacterium of the invention may be a Y. pseudotuberculosis bacterium. In another embodiment, a recombinant Yersinia bacterium of the invention may be a Y. enterocolitica bacterium. The Δasd, ΔP$_{crp}$::TT araC P$_{BAD}$ crp, ΔlacZ::caf1R-caf1M-caf1A-caf1 ΔyopJ and ΔyopK may be introduced into Y. enterocolitica to achieve attenuation and induce protective immune response against pathogens. In yet another embodiment, a recombinant Yersinia bacterium may be a Y. pestis bacterium, such as χ10015 (pCD1Ap), χ10030 (pCD1Ap), or χ10048 (pCD1Ap) listed in Table 1. In addition, the ΔyopJ and ΔyopK may be introduced into Y. pestis to achieve attenuation and enhance protective immune response against pathogens.

The present disclosure encompasses a recombinant Yersinia bacterium capable of regulated attenuation. "Attenuation," as used herein, refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the host and induce immune responses is, preferably, not substantially compromised. "Regulated attenuation," as used herein, refers to controlling when and/or where the bacterium is attenuated in a host. Typically, a bacterium initially colonizes the host in a non-attenuated manner, and is attenuated after several replication cycles.

A bacterium capable of regulated attenuation typically comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation. In one embodiment, the regulatory protein is a cAMP receptor protein (Crp), which is encoded by the crp gene. The bacterium can be attenuated by replacing the crp promoter with a regulatable promoter while still maintaining its immunogenicity (see Examples 4, 5, 6, and 7). In a preferred embodiment, such regulated expression can be achieved by replacing the promoter for the crp gene with a metabolically controlled promoter such as that of the arabinose operon, the araC P$_{BAD}$ activator-repressor-promoter system. In other embodiments, the regulatory promoter is linked to a spoT, rpoS, rovA, fur, ompR, phoPQ or cya gene to control gene expression.

As used herein, "antigen" refers to a biomolecule capable of eliciting an immune response in a host. In some embodiments, an antigen may be a protein, or fragment of a protein, or a nucleic acid. In an exemplary embodiment, the antigen elicits a protective immune response. As used herein, "protective" means that the immune response contributes to the lessening of any symptoms associated with infection of a host with the pathogen the antigen was derived from or designed to elicit a response against. For example, a protective antigen from a pathogen, such as Mycobacterium, may induce an immune response that helps to ameliorate symptoms associated with Mycobacterium infection or reduce the morbidity and mortality associated with infection with the pathogen. The use of the term "protective" in this invention does not necessarily require that the host is completely protected from the effects of the pathogen.

Some examples of microorganisms useful as a source for antigen are listed below. These may include microorganisms for the control of plague caused by Yersinia pestis and other Yersinia species such as Y. pseudotuberculosis and Y. enterocolitica, for the control of gonorrhea caused by Neisseria gonorrhoea, for the control of syphilis caused by Treponema pallidum, and for the control of venereal diseases as well as eye infections caused by Chlamydia trachomatis. Species of Streptococcus from both group A and group B, such as those species that cause sore throat or heart diseases, Erysipelothrix rhusiopathiae, Neisseria meningitidis, Mycoplasma pneumoniae and other Mycoplasma-species, Hemophilus influenza, Bordetella pertussis, Mycobacterium tuberculosis, Mycobacterium leprae, other Bordetella species, Escherichia coli, Streptococcus equi, Streptococcus pneumoniae, Brucella abortus, Pasteurella hemolytica and P. multocida, Vibrio cholera, Shigella. or RNA viruses, for example from the classes Papovavirus, Adenovirus, Herpesvirus, Poxvirus, Parvovirus, Reovirus, Picornavirus, Myxovirus, Paramyxovirus, Flavivirus or Retrovirus. Antigens may also be derived from pathogenic fungi, protozoa and parasites.

A suitable antigen derived from Yersinia, and designed to induce an immune response against Yersinia may include LcrV, F1 and Psn. LcrV of Yersinia is a 37-kDa multifunctional protein that has been shown to act at the level of secretion control by binding the Ysc inner-gate protein LcrG and to modulate the host immune response by altering cytokine production. LcrV also is essential for the unidirectional targeting of Yops to the cytosol of infected eukaryotic cells (Fields et al., 1999, Pettersson et al., 1999, Sarker et al., 1998). A promising subunit vaccine is based on LcrV antigen (Anderson et al., 1996, Leary et al., 1995, Williamson et al., 1995a). Active immunization with purified V antigen or passive immunization with antiserum against V antigen provides protection against plague in mice (Anderson et al., 1996, Leary et al., 1995, Williamson et al., 1995a, Motin et al., 1994). CD8+ T-cell immune responses primed to LcrV appear to confer protection against Y. pestis in mice (Wang et al., 2011b, Shreewastav et al., 2012). In one embodiment, a live attenuated Y. pseudotuberculosis used as a vector to inject the LcrV antigen from Y. pestis via T3SS elicits both antibody responses and specific T-cell responses to LcrV of Y. pestis, resulting in enhanced protective immunity against plague (See Examples 5, 6, and 7).

In another embodiment, Yersinia pestis uses its F1 capsule to enhance survival and cause virulence to mammalian hosts. Y. pestis expresses the caf operon (encoding the F1 capsule) in a temperature-dependent manner. Since F1 is produced in large quantities and secreted into the host tissues, it also serves as a major immune target. Immunity to infection has been correlated with the presence of antibody to the capsular F1 antigen (Williams et al., 1986), and immunization with the F1 antigen induces protection against the disease in animal models (Williamson et al., 1995a, Simpson et al., 1990, Meyer et al., 1974). A live attenuated Y. pseudotuberculosis strain with the caf operon inserted into its chromosome to synthesize F1 in a temperature-dependent manner, can enhance its immunogenicity (See Example 8).

In an exemplary embodiment, a bacterium may comprise one or more mutations selected from the group comprising Δasd, ΔmsbB:: P$_{msbB}$ msbB (EC), ΔP$_{crp}$::TT araC P$_{BAD}$ crp, ΔlacZ::caf1R-caf1M-caf1A-caf1 pYV-ω2 (ΔyopJ ΔyopK), and Δasd pYV-ω2 (ΔyopJ ΔyopK).

A recombinant bacterium may be administered to a host as a vaccine composition. As used herein, a vaccine composition may be a composition designed to elicit an immune response against Yersinia. Additionally, a vaccine composition may be a composition designed to elicit an immune response against Yersinia and against one or more additional pathogens, such as, Brucella, Francisella, Burkholderia or Borrelia. In an exemplary embodiment, the immune response is protective, as described above. In one exemplary embodiment, the immune response is protective against both pneumonic and bubonic plague. Immune responses to antigens are well studied and widely reported. A survey of immunology is given by Paul, W E, Stites D et. al. and Ogra P L. et. al. Mucosal immunity is also described by Ogra P L et. al.

Vaccine compositions of the present invention may be administered to any host capable of mounting an immune response. Such hosts may include all vertebrates, for example, mammals, including domestic animals, agricultural animals, laboratory animals, humans, and rarely in cold-blood animals. *Yersinia enterocolitica* has been found in water on cold blooded animals such as frogs and fish (Harvey et al., 1976, Zamora & Enriquez, 1987) and could be potentially transmissible to humans. However, the serotypes involved are not usually found in humans. Preferably, the host is a warm-blooded animal. The vaccine can be administered as a prophylactic, for treatment purposes, or for possible elimination of *Y. pestis* persistence in wild-animals.

In exemplary embodiments, the recombinant bacterium is alive when administered to a host in a vaccine composition of the invention. Suitable vaccine composition formulations and methods of administration are detailed below.

A vaccine composition comprising a recombinant bacterium may optionally comprise one or more possible additives, such as carriers, preservatives, stabilizers, adjuvants, and other sub stances.

Care should be taken when using additives so that the live recombinant bacterium is not killed, or have its ability to effectively colonize the host compromised by the use of additives. Stabilizers, such as sucrose, maltose, trehalose, lactose, inositol or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1\times10^7$ to $1\times10^{10}$ CFU depending upon the age of the host to be immunized. Administering multiple dosages may also be used as needed to provide the desired level of protective immunity.

A vaccine of the invention may be administered via any suitable route, such as by oral administration or gastric intubation. Additionally, other methods of administering the recombinant bacterium, such as intravenous, intramuscular, subcutaneous injection, intranasal administration or other parenteral routes, are possible.

In some embodiments, these compositions are formulated for oral administration. Accordingly, these compositions are preferably combined with pharmaceutically acceptable vehicles such as saline, Ringer's solution, dextrose solution, and the like. The concept of immunizing wildlife with oral bait vaccines was first proposed by the CDC and tested with captive red foxes for rabies control in the early 1960's (Rupprecht et al., 2004, Finnegan et al., 2002). The recent success of wide-scale oral rabies vaccination programs for mesocarnivores in North America and Northern Europe has greatly contributed to controlling the disease in wildlife (Rupprecht et al., 2004, Cross et al., 2007). Disease management through vaccination of wildlife reservoirs has advantages over other approaches such as culling and may be more acceptable to the public (Cross et al., 2007, Kaden et al., 2005). However, capturing and handling wild animals to vaccinate them individually is an expensive, time consuming and difficult process. Hence, the most practical approach is the use of oral baits for delivering vaccines to wildlife species. The success of the oral rabies vaccine has encouraged research into vaccination as a practical control means for other diseases such as Lyme disease caused by *B. burgdorferi* (Piesman, 2006, Bhattacharya et al., 2011, Meirelles Richer et al., 2011), tuberculosis caused by *M. bovis* (Aldwell et al., 2003, Ballesteros et al., 2009, Gormley & Corner, 2009, Nol et al., 2008, Nol et al., 2009, Tompkins et al., 2009, Ballesteros et al., 2011), and brucellosis caused by *B. abortus* (Cross et al., 2007). A recombinant raccoon poxvirus (RCN) has been developed to synthesize two *Y. pestis* antigens, F1 and LcrV. These recombinant proteins (designated RCN-F1 and RCN-V) have been developed into a baited subunit vaccine that protects black-tailed prairie dogs (*Cynomys ludovicianus*) against plague (Mencher et al., 2004, Rocke et al., 2008). However, preparations of RCN-vectored vaccines are time-consuming, expensive, and multiple immunizations are required to stimulate protective immune responses. Moreover, vaccines are far from full protection (Mencher et al., 2004, Rocke et al., 2008).

Embodiments also encompass kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

A further aspect encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). The monitoring of the response can be by quantitating the titers of antibodies or lymphocytes recognizing the selected antigens or by demonstrating and measuring the level of protective immunity.

In still another embodiment, a recombinant bacterium may be used in a method for eliciting an immune response against *Yersinia* and one or more additional pathogens in an individual in need thereof. The method comprises administrating to the host an effective amount of a composition comprising a recombinant bacterium as described herein.

In a further embodiment, a recombinant bacterium described herein may be used in a method for ameliorating one or more symptoms of bubonic plague, pneumonic plague, or yersiniosis in a host in need thereof. The method comprises administering an effective amount of a composition comprising a recombinant bacterium as described herein.

Various other purposes and advantages will become clear from its description in the specification that follows. Therefore, to the accomplishment of the objectives described above, the embodiments disclosed herein include the features hereinafter fully described in the detailed description of the preferred embodiments, and particularly pointed out in the claims. However, such description discloses only some of the various ways in which the invention may be practiced.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are

15 disclosed and still obtain a like or similar result without departing from the spirit and scope of the invention, therefore all matter set forth or shown in the accompanying drawings is to be interpreted as illustrative and not in a limiting sense.

Definitions

The term "yersiniosis" as used herein, refers to a bacterial disease that generally affects the intestinal tract. It is caused by a bacterium of the genus *Yersinia* (*Y. enterocolitica* and *Y. pseudotuberculosis*).

The term "protective immune responses", as used herein, refers to the protection against infectious disease conferred either by the immune response generated by immunization by a recombinant Yptb vaccine strain.

The term "altered," as used herein, refers to any change in the nucleic acid sequence that results in the nucleic acid sequence not being expressed. In an exemplary embodiment, the alteration results in the nucleic acid sequence not being expressed in a host. In one embodiment, the alteration is a deletion. In another embodiment, the alteration places an essential nucleic acid under the control of a regulatable promoter, such that the nucleic acid is not expressed in a host.

The term "balanced-lethal" or "balanced attenuated" host vector systems refers to a recombinant bacterium comprising at least one chromosomally encoded essential nucleic acid sequence, wherein the essential nucleic acid sequence is altered so that it is not expressed, and at least one extrachromosomal vector. An "essential nucleic acid" is a native nucleic acid whose expression is necessary for cell viability or a metabolic activity essential for virulence. Consequently, a bacterium is non-viable and/or avirulent if an essential nucleic acid sequence is not expressed. Therefore, the bacterium further comprises at least one extrachromosomal vector. The vector comprises a nucleic acid sequence, that when expressed, substantially functions as the essential nucleic acid. Hence, the bacterium is viable and/or virulent when the vector is expressed. This promotes stable maintenance of the vector.

The term "promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same.

The term "invasiveness," as used here, refers to the ability of the recombinant bacterium to infect a host and invade into internal effector lymphoid tissues.

The "Δ" as used herein, refers to gene deletion; The "::" as used herein, refers to gene insertion; The "asd" as used herein, refers to a gene encoding aspartate-semialdehyde dehydrogenase. The asd mutants of Gram-negative bacteria have an obligate requirement for diaminopimelic acid (DAP), which is an essential constituent of the peptidoglycan layer of the cell wall of these organisms (Schleife. Kh & Kandler, 1972). The "msbB" refers to a gene encoding a distinct, late-functioning acyltransferase of lipid A assembly (Brozek & Raetz, 1990); the "ΔmsbB::$P_{msbB}$ msbB (EC)" refers to a msbB gene of Yptb replaced by the msbB gene from *E. coli* K-12. The "crp" refers to a gene encoding cAMP receptor protein. The "$\Delta P_{crp}$::TT araC $P_{BAD}$ crp" refers to the promoter of crp gene replaced by arabinose regulated promoter (TT araC $P_{BAD}$) (Sun et al., 2010).

The "lacZ" refers to a gene encoding β-galactosidase, which does not function in Yptb. The "caf1R-caf1M-caf1A-caf1" refers to the *Y. pestis* capsule synthesis operon. The fraction 1 (F1) antigen is a major component of the surface of *Y. pestis* (Perry & Fetherston, 1997) and has been identified as a protective antigen (Andrews et al., 1996). Production of the 15.5-kDa F1 subunit is encoded by the caf1 gene (Galyov et al., 1990), and the caf1M (Galyov et al., 1991) and caf1A (Karlyshev et al., 1992b) genes that encode, respectively, a chaperone which allows export of the F1 antigen subunit to the surface and a protein which anchors the F1 antigen into the outer membrane. The production of F1 antigen is temperature regulated by the product of the caf1R gene (Karlyshev et al., 1992a), and the induction of expression at 37° C. is thought to be related to its role in protecting the bacterium from killing by host phagocytic cells (Williams et al., 1972), possibly by preventing complement-mediated opsonisation or by disrupting phagocytic cell membranes (Rodrigues et al., 1992). The "ΔlacZ::caf1R-caf1M-caf1A-caf1" refers to the caf1 operon inserted into the lacZ locus in the Yptb chromosome.

The "yopJ" refers to a gene encoding a cysteine protease, an enzyme with acetyltransferase and deubiquitinase activities that counteracts the proinflammatory response in host cells by inhibiting the mitogen-activated protein kinase and NF-κB signaling pathways (Bliska, 2006, Orth, 2002, Orth et al., 2000, Zhou et al., 2005). The "yopK" refers to a gene encoding YopK that has been shown to modulate the size of the translocation pore in red blood cells and epithelial cells, and control translocation of Yops effectors (Holmstrom et al., 1997, Dewoody et al., 2011).

The "lcrV" refers to a gene encoding V antigen that is a 37-kDa multifunctional protein of *Yersinia* species encoded on the 70-kb low calcium response plasmid. V antigen participates in the type III secretion system in *Y. pestis* regulating the production and facilitating the translocation of *Yersinia* outer proteins (Yops) with anti-host activity into the host cell (Pettersson et al., 1999, Sarker et al., 1998). Active immunization with purified V antigen or passive immunization with antiserum against V antigen provides protection against plague in mice (Leary et al., 1995, Motin et al., 1994).

EXAMPLES

Table 1 lists the bacterial strains and plasmids referred to throughout the Description and Examples.

TABLE 1

Strains and plasmids used in this study

| | Characteristics | Source/Reference/ Derivation |
|---|---|---|
| Strains *Escherichia coli* | | |
| χ6212 | F-Δ(argF-lacZYA)-U169 glnV44 1-deoR f80dlacZΔM15 gyrA96 recA1 relA1 endA1ΔasdA4 Δ(zhf-2::Tn10) thi-1 hsdR17 | (Kang et al., 2002) |
| χ7213 | thi-1 thr-1 leuB6 fhuA21 lacY1 glnV44 ΔasdA4 recA1 RP4 2-Tc::Mu [λpir]; $Km^r$ | (Kang et al., 2002) |

TABLE 1-continued Strains and plasmids used in this study

| | Characteristics | Source/Reference/Derivation |
|---|---|---|
| *Yersinia pestis* | | |
| *Y. pestis* KIM6(pCD1Ap) | Pgm⁻, pMT1, pPCP1, pCD1Ap | (Gong et al., 2001) |
| *Y. pestis* KIM6+(pCD1Ap) | Pgm⁺, pMT1, pPCP1, pCD1Ap | (Gong et al., 2001) |
| χ10015(pCD1Ap) | ΔlpxP::P$_{lpxL}$ lpxL | *Y. pestis* KIM6+(pCD1Ap) |
| χ10030(pCD1Ap) | ΔlpxP::P$_{lpxL}$ lpxL ΔP$_{crp}$::TT araC P$_{BAD}$ crp | χ10015(pCD1Ap) |
| χ10048(pCD1Ap) | Δasd ΔlpxP::P$_{lpxL}$ lpxL ΔP$_{crp}$::TT araC P$_{BAD}$ crp | χ10030(pCD1Ap) |
| *Y. enterocolitica* | | |
| *Y. enterocolitica* WA | biogroup 1B serotype O:8 | Received from R. Perry |
| *Y. pseudotuberculosis* | | |
| χ10051 | *Y. pseudotuberculosis* PB1+, serotype O:1B | Received from R. Perry |
| χ10052 | ΔmsbB (YPTS_2105) | χ10051 |
| χ10053 | ΔmsbB:: P$_{msbB}$ msbB (EC) | χ10052 |
| χ10054 | ΔP$_{crp}$::TT araC P$_{BAD}$ crp | χ10051 |
| χ10055 | ΔmsbB::P$_{msbB}$ msbB (EC) ΔP$_{crp}$::TT araC P$_{BAD}$ crp | χ10053 |
| χ10056 | Δasd ΔP$_{crp}$::TT araC P$_{BAD}$ crp | χ10054 |
| χ10057 | Δasd ΔmsbB::P$_{msbB}$ msbB (EC) ΔP$_{crp}$::TT araC P$_{BAD}$ crp | χ10055 |
| χ10058 | pYV-ω1 (ΔyopK) | χ10051 |
| χ10059 | Δasd pYV-ω1 (ΔyopK) | χ10058 |
| χ10060 | ΔlacZ | χ10051 |
| χ10061 | ΔlacZ::caf1R-caf1M-caf1A-caf1 | χ10060 |
| χ10062 | ΔlacZ::caf1R-caf1M-caf1A-caf1 pYV-ω1 (ΔyopK) | χ10061 |
| χ10063 | Δasd ΔlacZ::caf1R-caf1M-caf1A-caf1 pYV-ω1 (ΔyopK) | χ10062 |
| χ10066 | Δasd | χ10051 |
| χ10067 | pYV-ω2 (ΔyopJ ΔyopK) | χ10058 |
| χ10068 | ΔlacZ::caf1R-caf1M-caf1A-caf1 pYV-ω2 (ΔyopJ ΔyopK) | χ10063 |
| χ10069 | Δasd pYV-ω2, (ΔyopJ ΔyopK) | χ10067 |
| χ10070 | Δasd ΔlacZ::caf1R-caf1M-caf1A-caf1 pYV-ω2 (ΔyopJ ΔyopK) | χ10068 |
| Plasmids | | |
| pRE112 | Suicide vector, Cm$^r$, mob⁻ (RP4)R6K ori, sacB | Curtiss collection |
| pYA3332 | Asd⁺; p15A ori | Curtiss collection |
| pYA3337 | Asd⁺; pSC101 ori | Curtiss collection |
| pYA3342 | Asd⁺; pBR ori | Curtiss collection |
| pYA4454 | Amp$^r$, pSC101 ori | Curtiss collection |
| pYA4581 | ΔP$_{crp}$::TT araC P$_{BAD}$ crp, Amp$^r$, pYA3700 derivate | Curtiss collection |
| pYA5151 | ΔmsbB of *Y. pseudotuberculosis*, pRE112 derivate | Curtiss collection |
| pYA5152 | ΔmsbB::P$_{msbB}$ msbB (EC) of *Y. pseudotuberculosis*, pRE112 derivate | Curtiss collection |
| pYA5153 | ΔP$_{crp}$::TT araC P$_{BAD}$ crp of *Y. pseudotuberculosis*, pRE112 derivate | Curtiss collection |
| pYA5154 | Δasd of *Y. pseudotuberculosis*, pRE112 derivate | Curtiss collection |
| pYA5184 | ΔlacZ::caf1R-caf1M-caf1A-caf1 of *Y. pseudotuberculosis*, pRE112 derivate | Curtiss collection |
| pYA5199 | The sycE-yopE' (1-138aa)-lcrV fragment was cloned into pYA3332 | Curtiss collection |
| pYA5203 | The sycE-yopE' (1-138aa)-lcrV fragment and caf1 operon were cloned into pYA3332 | Curtiss collection |
| pYA5243 | ΔlacZ of *Y. pseudotuberculosis*, pRE112 derivate | Curtiss collection |
| pYA5323 | ΔyopK of *Y. pseudotuberculosis*, pRE112 derivate | Curtiss collection |
| pYA5324 | ΔyopJ of *Y. pseudotuberculosis*, pRE112 derivate | Curtiss collection |

Example 1

Construction of a Live Attenuated *Y. pseudotuberculosis* Strain as a Carrier for Delivering Antigen Research demonstrated that *Y. pseudotuberculosis* PB1 produces penta-acylated and C16:1-containing hexa-acylated lipid A species when grown at 21° C., while tetra-acylated lipid A and C16:0-containing penta-acylated are observed when bacteria are grown at 37° C. (Rebeil et al., 2004). The mechanism for the temperature-sensitive difference in lipid A acylation in *Y. pseudotuberculosis* has not yet been elucidated. *Y. pseudotuberculosis* contains a biochemically uncharacterized lpxL homolog that may be responsible for formation of penta-acylated lipid A at 21° C. and/or 37° C. Additionally, Perez-Gutierrez et al. (Perez-Gutierrez et al., 2010) have shown that the *Y. enterocolitica* MsbB acyltransferase, is temperature sensitive, and has a high degree of identity (94%) with MsbB (YPTS 2105) of *Y. pseudotuberculosis*. Therefore we infer that MsbB in *Y. pseudotuberculosis* is temperature-sensitive.

The major tetra-acylated lipid A at 37° C. (mammalian host temperature) formed in *Y. pestis* can suppress early immune responses (Montminy et al., 2006, Telepnev et al., 2009). In order to overcome the immunosuppression, *Y. pestis* was engineered to produce hexa-acylated lipid A by expressing *E. coli* LpxL (Montminy et al., 2006, Sun, 2011). This strain was attenuated and could induce potent protective immunity against plague (Montminy et al., 2006, Sun, 2011). Our studies showed that combining production of hexa-acylated lipid A and regulation of Crp synthesis under araC $P_{BAD}$ regulon made the *Y. pestis* mutant more attenuated than *Y. pestis* with hexa-acylated lipid A alone while retaining great immunogenicity (Sun, 2011). Here we would use a similar approach to achieve *Y. pseudotuberculosis* attenuation as described in our previous paper (Sun, 2011).

Figure 1A:
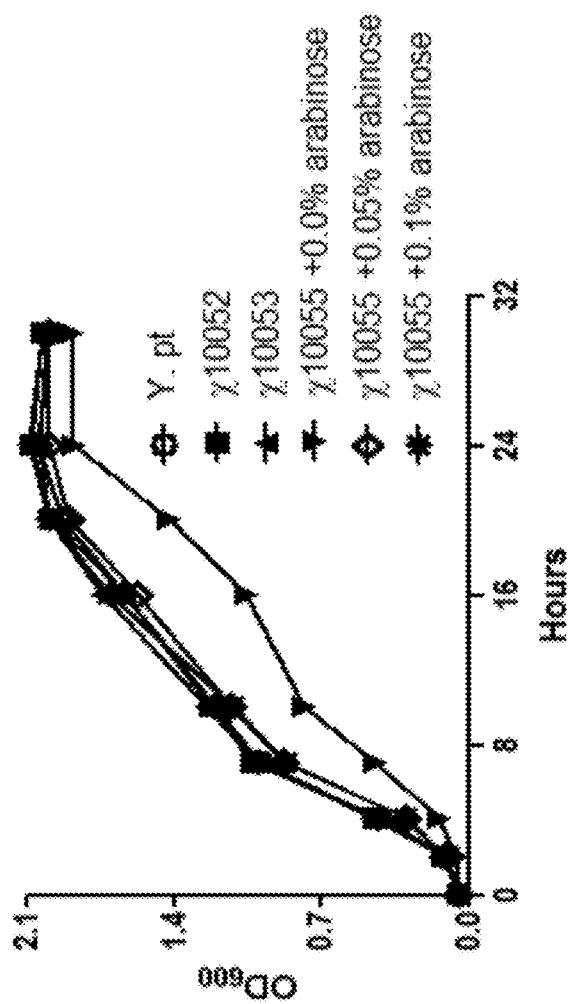

Unlike *Y. pestis*, *Y. pseudotuberculosis* encodes a functional lpxL homolog (Zhou & Yang, 2009). In addition, MsbB in *Y. pseudotuberculosis* may be temperature-sensitive which results in major tetra-acylated lipid A observed in *Y. pseudotuberculosis* grown at 37° C. and associated with immunosuppressive properties (Rebeil et al., 2004). Therefore we replaced only the msbB gene and its promoter in *Y. pseudotuberculosis* with the *E. coli* msbB gene and its native promoter (ΔmsbB:: $P_{msbB}$::msbB$_{(EC)}$) to drive the mutant strain to synthesize hexa-acylated lipid A at 37° C. which can be recognized by Toll like receptor 4 (TLR4) to enhance immunostimulatory properties. We thus constructed χ10053 (ΔmsbB::$P_{msbB}$ msbB$_{(EC)}$). Then, the ΔP$_{crp21}$::TT araC $P_{BAD}$ crp mutation was introduced into strain χ10053 to construct χ10055 (ΔmsbB868::$P_{msbB}$ msbB$_{(EC)}$ ΔP$_{crp21}$::TT araC $P_{BAD}$ crp) to obtain more attenuation. Measurement of bacterial growth indicated that the growth curve of the mutant strain with the ΔmsbB868 or ΔmsbB868::$P_{msbB}$ msbB$_{(EC)}$ mutation was the same as that of the wild-type strain, while mutant strain χ10055 also containing the ΔP$_{crp21}$::TT araC $P_{BAD}$ crp mutation required arabinose for optimal growth (FIG. 1A).

Figure 1B:
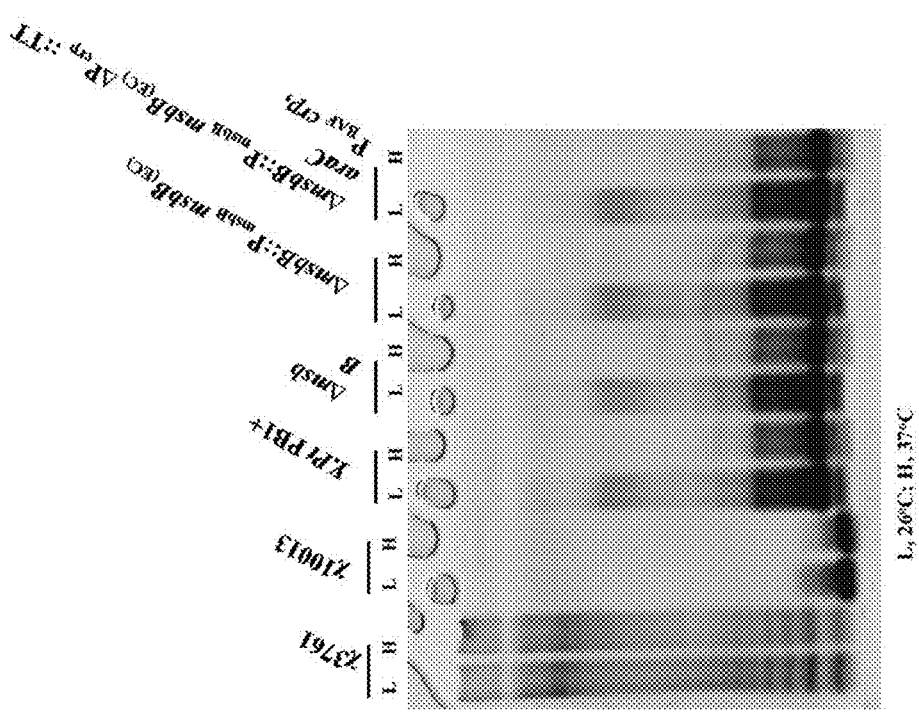

LPS synthesis of each mutant was analyzed by silver staining (FIG. 1B). The result demonstrated that there was no detectable alteration in the lipid A acylation pattern of wild-type *Y. pseudotuberculosis* PB1+ dependent on growth temperature. Surprisingly, the lipid A portion wasn't altered even in the msbB (YPTS 2105) mutant strain, χ10052 (Table 1). In addition, replacing the *Y. pseudotuberculosis* msbB gene and its promoter with the *E. coli* msbB gene and its native promoter (ΔmsbB:: $P_{msbB}$::msbB$_{(EC)}$) also did not cause any shifts in the migration of LPS analyzed by silver staining (FIG. 1B).

Figure 1C:
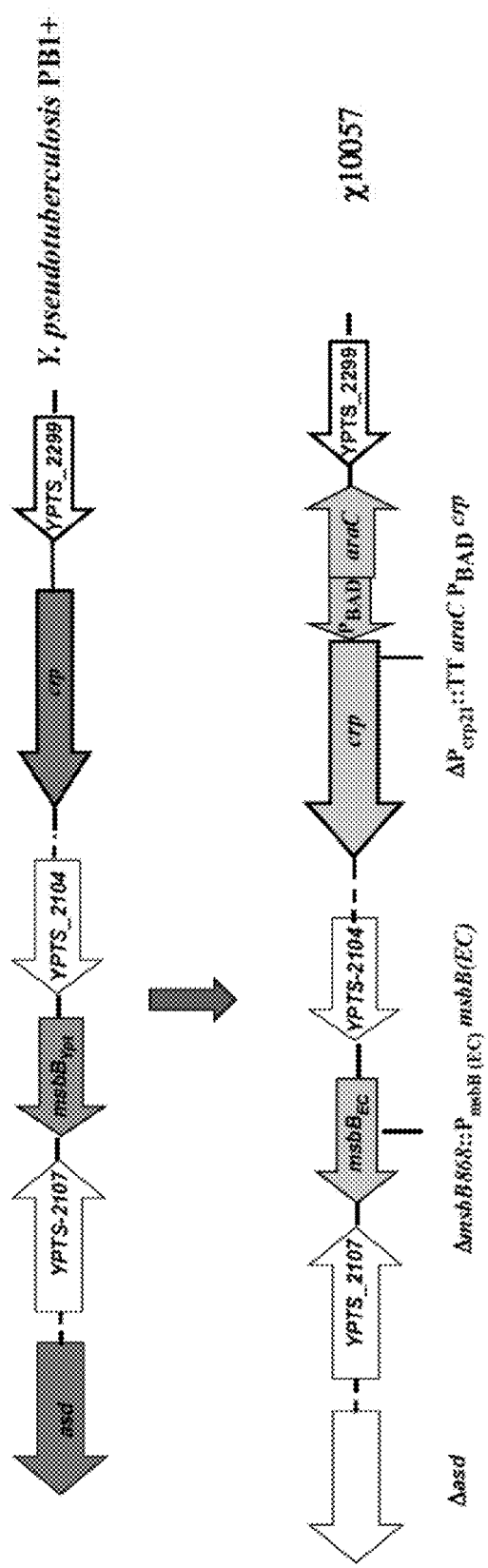

To facilitate antigen synthesis specified by plasmids in recombinant *Y. pseudotuberculosis* strains, we adapted the balanced-lethal Asd+ plasmid maintenance system developed for *Salmonella* (Nakayama et al., 1988) in *Y. pseudotuberculosis*. Based on the attenuated mutant χ10055, the Δasd mutation was introduced into χ10055 to construct χ10057 (Δasd-206 ΔmsbB868::$P_{msbB}$ msbB$_{(EC)}$ ΔP$_{crp21}$::TT araC $P_{BAD}$ crp) to enable use of a balanced-lethal Asd+ plasmid to facilitate stable antigen synthesis (FIG. 1C).

Example 2

Synthesis, Secretion and Translocation of Recombinant Chimeric Proteins YopE$_{Nt138}$-LcrV by Strain χ10057

Cellular immunity plays an important role in protection against pneumonic plague (Parent et al., 2005, Janssen & Surgalla, 1969, Pujol et al., 2005, Lukaszewski et al., 2005, Elvin & Williamson, 2004, Parent et al., 2006). To stimulate cellular immunity, heterologous antigens fused with YopE (1-138aa) allows the chimeric protein to be specifically transported via the T3SS of live attenuated *Y. pseudotuberculosis* strains to become accessible to the MEW class I-restricted antigen-processing pathways and stimulate an antigen-specific cellular immune response (Wiedig et al., 2005, Russmann et al., 2003).

Figure 2A:
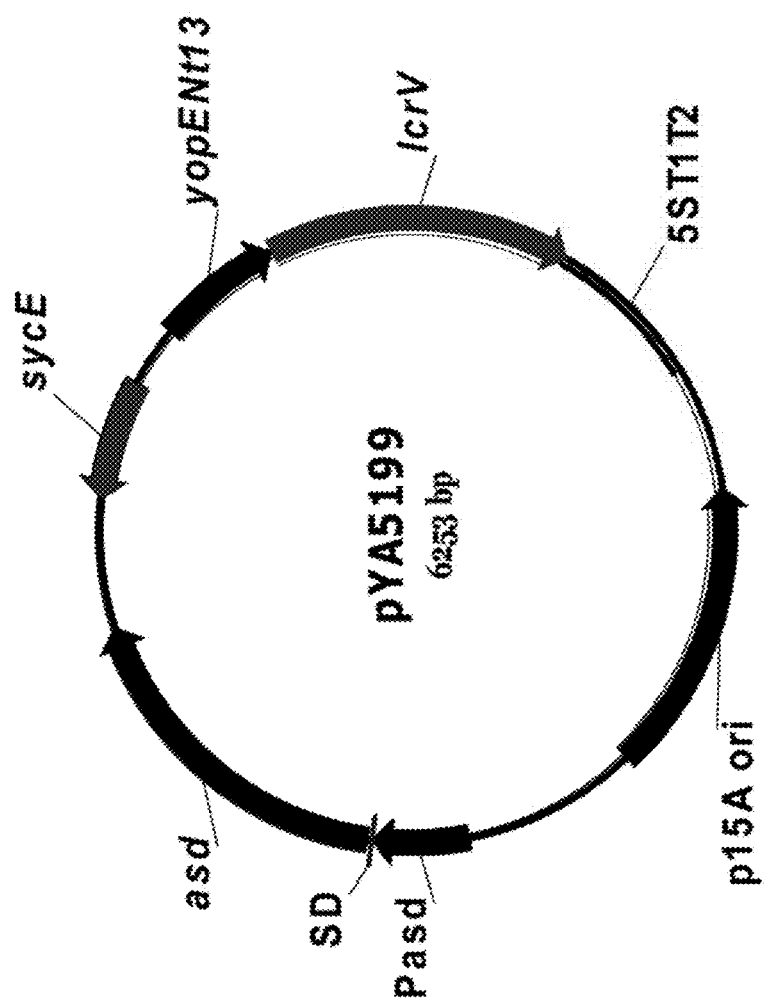

We constructed plasmid vectors containing the secretion and translocation signals of the *Yersinia* T3SS effector protein YopE, which are specified by the first 138 amino acids in the amino-terminal region of YopE (designated YopE$_{Nt138}$). SycE encoded by sycE is the chaperon protein for YopE and increases the translocation of YopE (Feldman et al., 2002) or YopE$_{Nt138}$ fusion protein (Russmann et al., 2000, Russmann et al., 2001). The lcrV of *Y. pestis* by in-frame fusion with sycE-yopE$_{Nt138}$ was cloned into pYA3332 to generate pYA5199 (FIG. 2A).

Figure 2B:
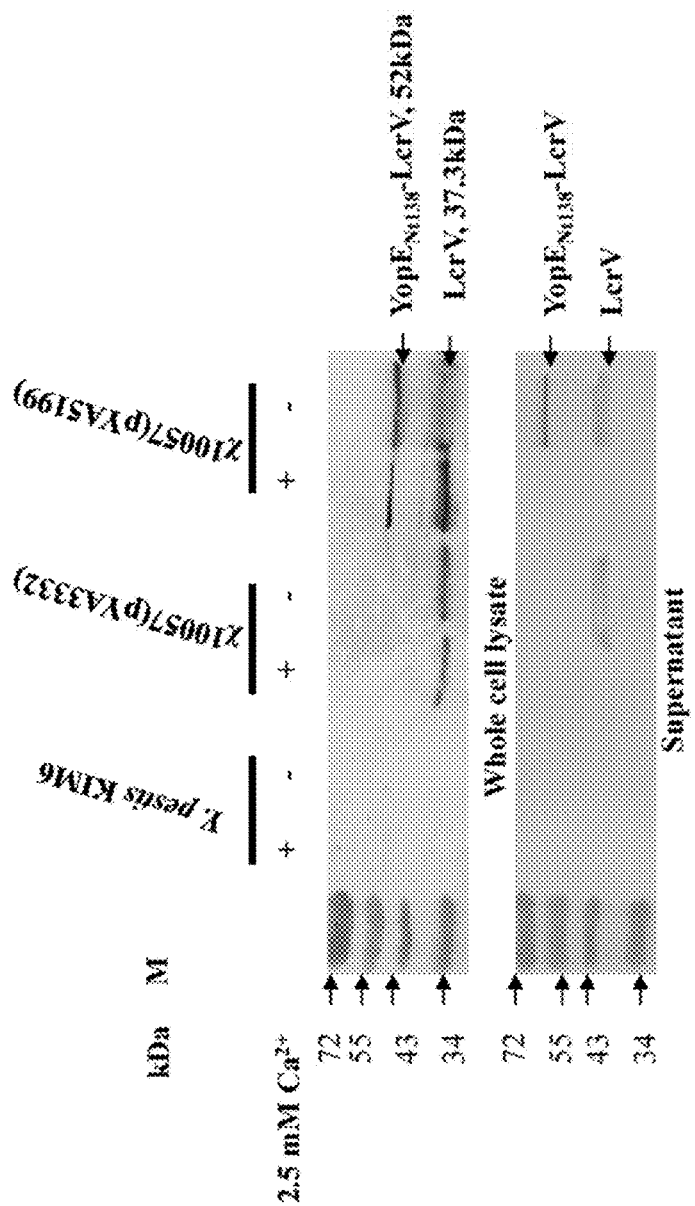

To test secretion of the chimeric protein YopE$_{Nt138}$-LcrV, cultures of χ10057 harboring either pYA3332 (plasmid control) or pYA5199 (yopE$_{Nt138}$-lcrV) were grown at 26° C. to an OD$_{600}$ of 0.8 in LB medium with 0.05% arabinose and then subcultured into calcium-chelated medium supplemented with 0.05% arabinose for 6 h at 37° C. as described in Materials and Methods. Immunoblotting was used to detect synthesis of YopE$_{Nt138}$-LcrV fusion protein. The molecular mass of YopE$_{Nt138}$-LcrV was 52 kDa as expected (FIG. 2B). These results demonstrated that the YopE$_{Nt138}$-LcrV hybrid proteins were synthesized and secreted in vitro.

Figure 2C:
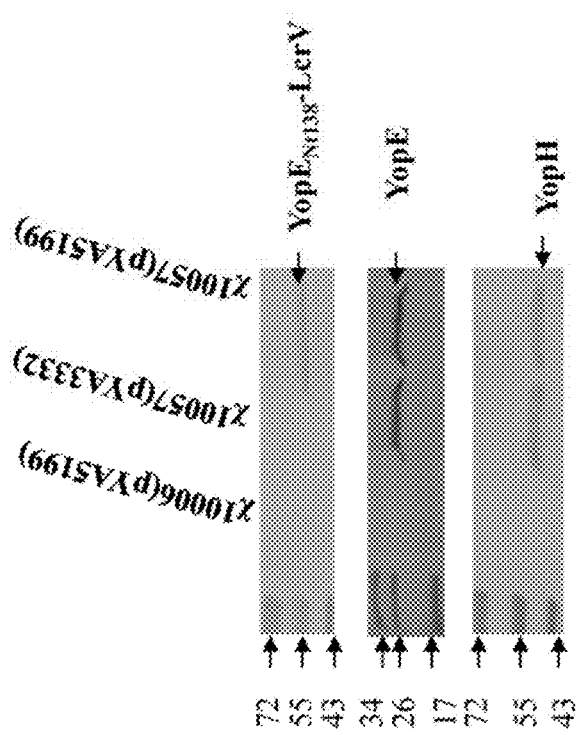

To analyze translocation of the hybrid proteins, HeLa cells were infected with χ10057 harboring either pYA3332 as a negative control or pYA5199 (yopE$_{Nt138}$-lcrV). Our results demonstrated that the YopE$_{Nt138}$-LcrV was translocated into the cytosol of host cells by the *Y. pseudotuberculosis* mutant strain (FIG. 2C).

Example 3

Virulence of Recombinant Strains in Mice

Our results demonstrated that the LD$_{50}$ of wild-type Yptb PB1+ was around 1.5×10$^8$ CFU. We also did not observe any changes in virulence of χ10052 (ΔmsbB868) and χ10053 (ΔmsbB868::$P_{msbB}$::msbB$_{(EC)}$). Virulence of χ10055 determined by oral administration in Swiss Webster mice demonstrated that the LD$_{50}$ of χ10055 increased at least by 10$^2$ fold (>4×10$^9$ CFU) compared to the wild-type strain (LD$_{50}$, 5×10$^7$ CFU). To investigate whether plasmids introduced into the χ10057 strain (Δasd-206 ΔmsbB868::$P_{msbB}$ msbB$_{(EC)}$ ΔP$_{crp21}$::TT araC $P_{BAD}$ crp) affects its virulence, we infected Swiss Webster mice orally with 4.5×10$^9$ CFU of χ10057 (pYA3332) (vector control) or 7.0×10$^9$ CFU of χ10057 (pYA5199) (yopE$_{Nt138}$-lcrV). All the mice infected with χ10057 harboring different plasmids did not show any sign of weight loss or any symptoms of disease. Thus, the LD$_{50s}$ of χ10057 (pYA3332) and χ10057 (pYA5199) were more than 4.5×10$^9$ CFU (Table 2)

TABLE 2

Virulence of different *Y. pseudotubculosis* constructions

| Strains | Dose (CFU) | Route | Survivors/death |
|---|---|---|---|
| Wild-type *Y. pseudotuberculosis* | 1.5 × 10$^7$ | Oral | 6/10 |
|  | 1.5 × 10$^8$ | Oral | 4/10 |
|  | 1.5 × 10$^9$ | Oral | 1/10 |

TABLE 2-continued

Virulence of different *Y. pseudotubculosis* constructions

| Strains | Dose (CFU) | Route | Survivors/death |
|---|---|---|---|
| χ10052 (ΔmsbB) | $1.2 \times 10^7$ | Oral | 6/10 |
|  | $1.2 \times 10^8$ | Oral | 5/10 |
|  | $1.2 \times 10^9$ | Oral | 2/10 |
| χ10053 (ΔmsbB::P$_{msbB}$::msbB$_{(EC)}$) | $1.8 \times 10^7$ | Oral | 7/10 |
|  | $1.8 \times 10^8$ | Oral | 5/10 |
|  | $1.8 \times 10^9$ | Oral | 1/10 |
| χ10055 (ΔmsbB::P$_{msbB}$ msbB (EC) ΔP$_{crp}$::TT araC P$_{BAD}$ crp) | $4 \times 10^9$ CFU | Oral | 10/10 |
| χ10057(pYA3332) (Δasd ΔmsbB::P$_{msbB}$ msbB (EC) ΔP$_{crp}$::TT araC P$_{BAD}$ crp) | $4.5 \times 10^9$ | Oral | 10/10 |
| χ10057(pYA5199) (Δasd ΔmsbB::P$_{msbB}$ msbB (EC) ΔP$_{crp}$::TT araC P$_{BAD}$ crp) | $7.0 \times 10^9$ | Oral | 10/10 |
| BSG | — | Oral | 5/5 |

Example 4

Evaluate Abilities of the RAYV Strains to Colonize Lymphoid Tissues in Mice

Based on these data, we evaluated the ability of χ10057 harboring different plasmids to disseminate into Peyer's patches, spleens and livers of mice. We orally infected groups of mice with $0.7 \times 10^9$ CFU of wild-type *Y. pseudotuberculosis* PB1+, $1.5 \times 10^9$ CFU of χ10057 (pYA3332) or $1.3 \times 10^9$ CFU of χ10057 (pYA5199).

Figure 3A:
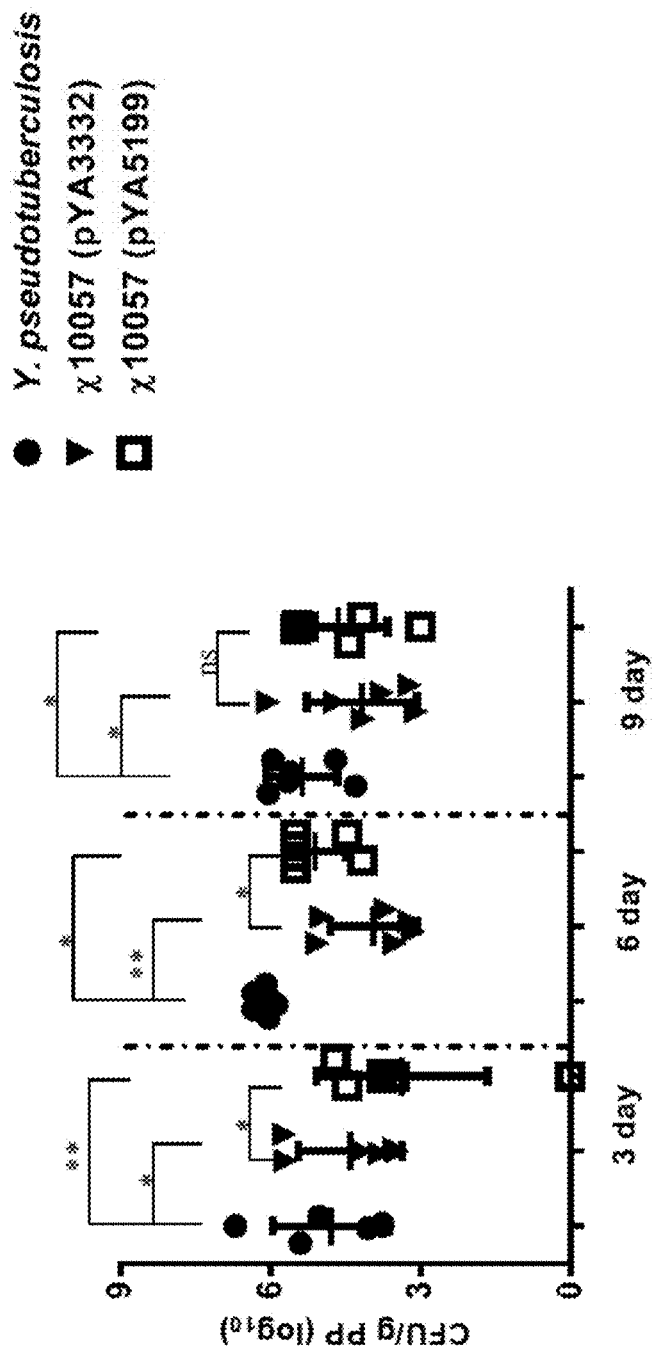

In Peyer's patches, the titers of wild-type Yptb PB1+ strain steadily increased at 3 and 6 days post-infection and slightly declined at 9 days post-infection. The titers of χ10057 (pYA3332) and χ10057 (pYA5199) strains were significantly lower than that of the wild-type PB1+ strain at different times post-infection (FIG. 3A). The bacterial titers of χ10057 (pYA5199) significantly increased, while the titers of χ10057 (pYA3332) decreased around one log at 6 days post-infection. At 9 days post-infection, the bacterial titers of both mutant strains reached similar levels (FIG. 3A).

Figure 3B:
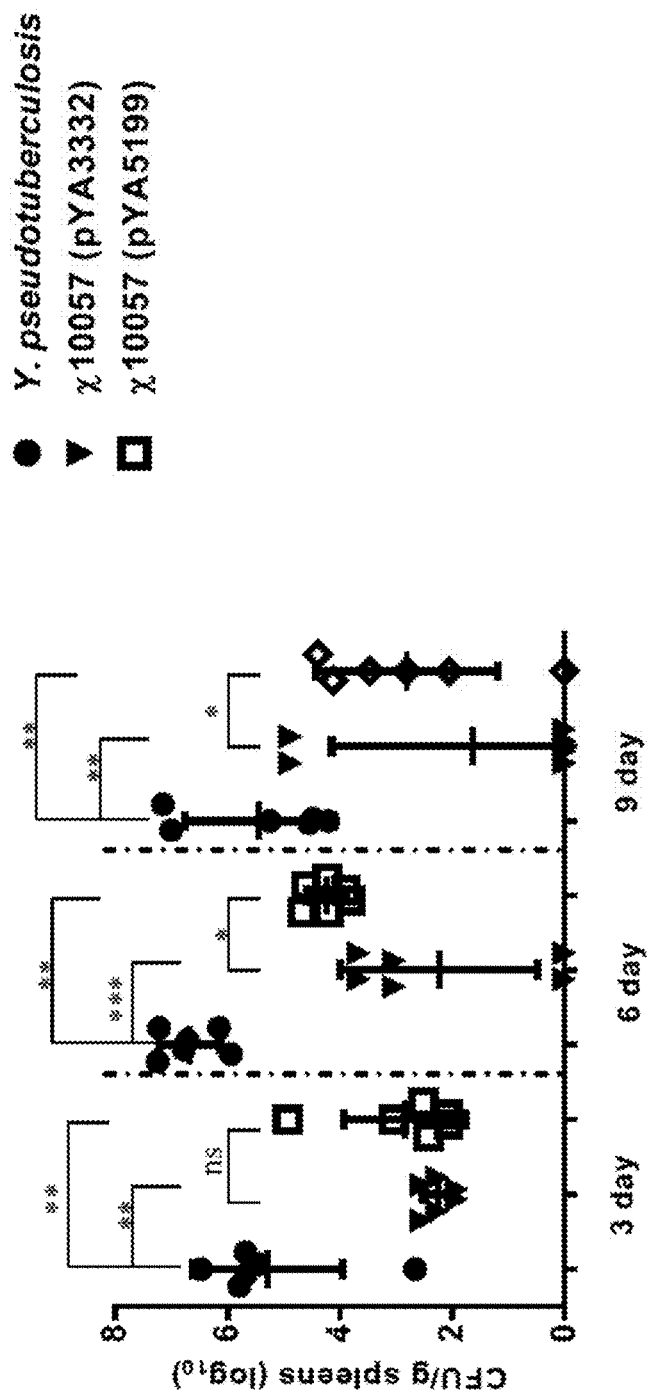
Figure 3C:
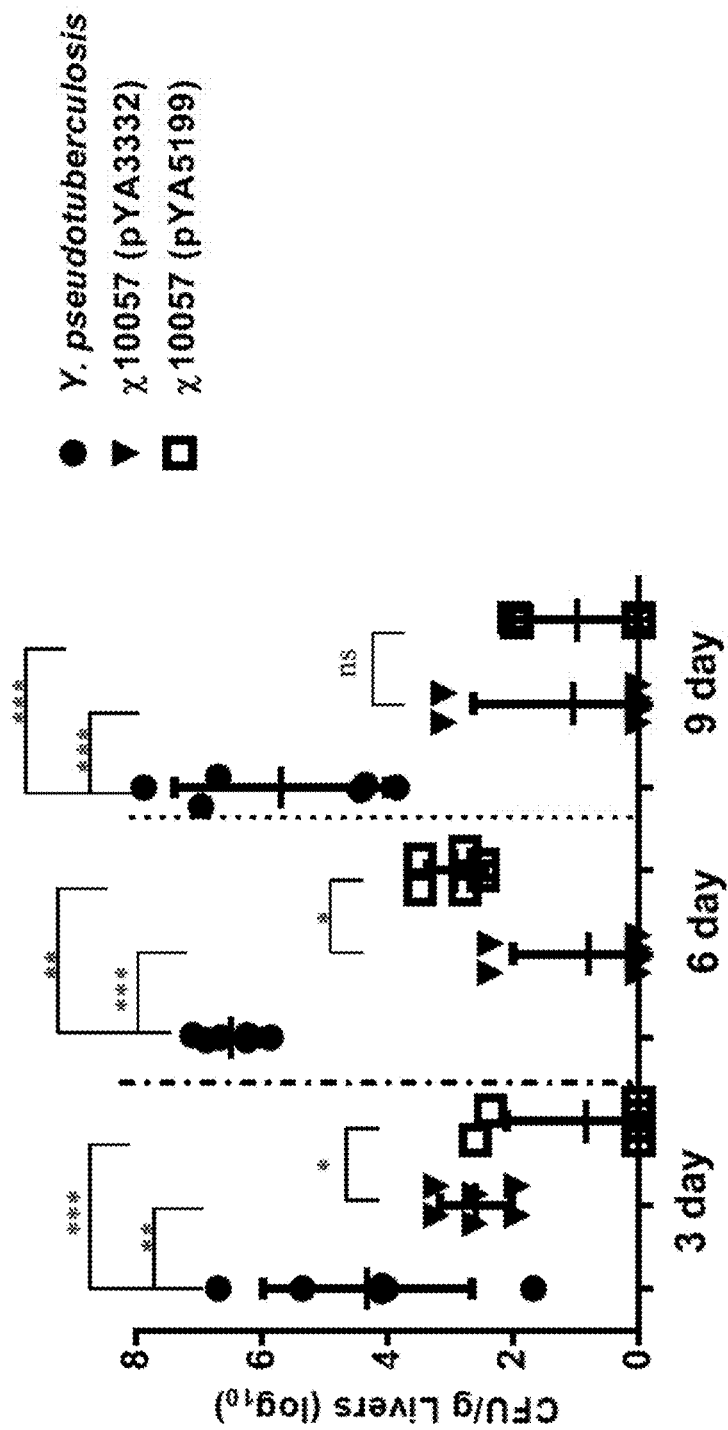

The wild-type strain can effectively colonize in spleen and liver and reach higher titers at 3, 6 and 9 days post-infection, but the mutant strain containing different plasmids can't effectively disseminate into spleen and liver at 3 days post-infection (FIGS. 3B and C). Although the titers of χ10057 (pYA5199) in spleens and livers were significantly lower than that of the wild-type strain, strain χ10057 (pYA5199) synthesizing YopE$_{Nt138}$-LcrV seemed to be more effective in colonizing spleen and liver than χ10057 (pYA3332) at 6 days post-infection (FIGS. 3B and C). At 9 d post-infection, the titers of χ10057 (pYA3332) and χ10057 (pYA5199) in the spleen and liver were very low (FIGS. 3B and C). At 15 days post-infection, no bacteria were detected in spleens and livers of mice infected with χ10057 (pYA3332) and χ10057 (pYA5199).

The results suggested that χ10057 (pYA5199) synthesizing YopE$_{Nt138}$-LcrV might increase its ability of invasion in spleen and liver at 6 days post-infection.

Example 5

Protective Efficacy Against Pneumonic Plague Challenge

Figure 4A:
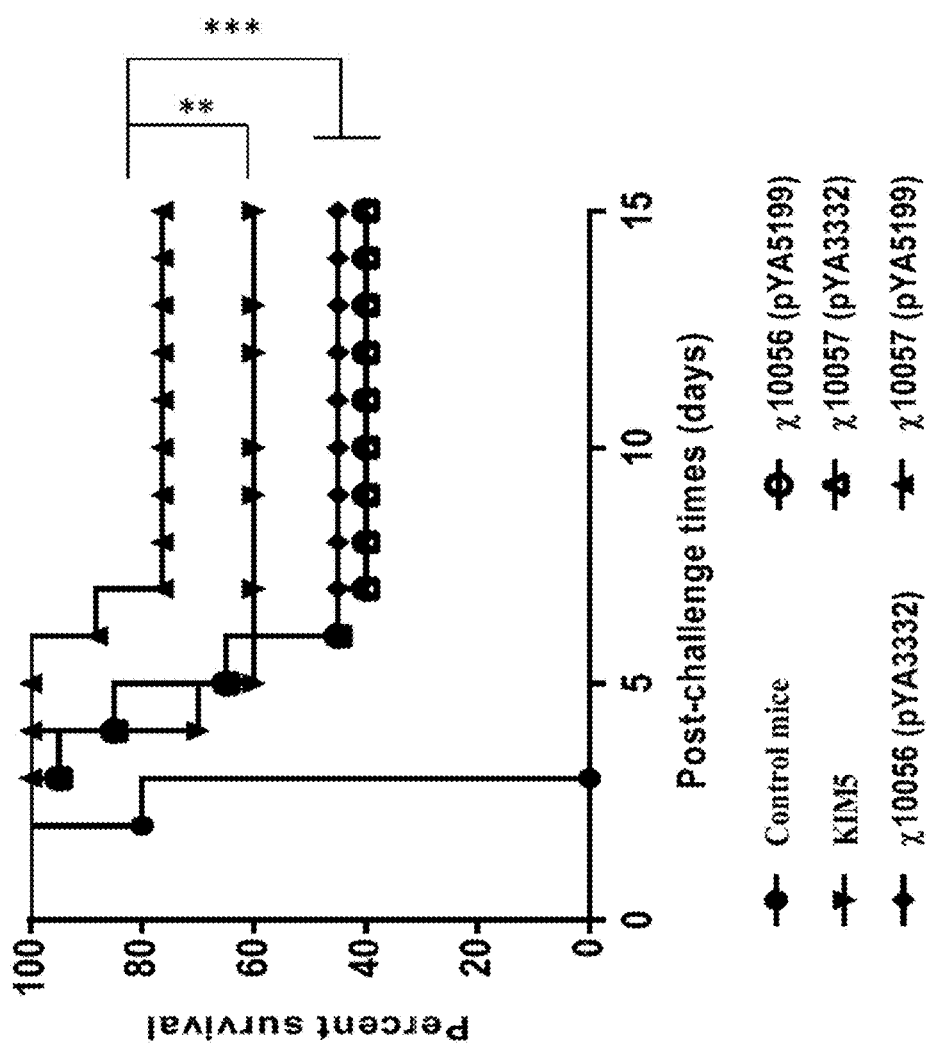

The LD$_{50}$ of *Y. pestis* KIM6+ (pCD1Ap) used as a challenge strain was 100 CFU for i.n. challenge (Sun, 2011). Groups of mice were orally immunized with a single dose ($10^9$ CFU) of χ10056 (pYA3332), χ10057 (pYA3332) (plasmid controls), χ10056 (pYA5199), and χ10057 (pYA5199) (yopE$_{Nt138}$-lcrV), with BSG as a negative control, or were subcutaneously immunized with $2.5 \times 10^7$ CFU of *Y. pestis* KIM5 (Pgm) as a standard attenuated *Y. pestis* vaccine and challenged intranasally with ~240 LD$_{50}$ ($2.4 \times 10^4$ CFU) of *Y. pestis* KIM6+(pCD1Ap) at 35 days after initial immunization. Results showed that a single oral dose of χ10057 (pYA5199) provided 80% protection against an i.n. challenge of KIM6+(pCD1Ap) (FIG. 4A). While the immunization of *Y. pestis* KIM5 (Pgm−), χ10056 (pYA3332), χ10056 (pYA5199) or χ10057 (pYA3332) provided partial protection with 60%, 42% or 40%, respectively. Their protective efficacy was significantly lower than that of χ10057 (pYA5199). None of the mice immunized with BSG were protected (FIG. 4A). The mice surviving wild-type *Y. pseudotuberculosis* PB1+ infection were also pooled together (10 mice) for intranasal challenge with ~130 LD$_{50}$ ($1.3 \times 10^4$ CFU) of *Y. pestis* KIM6+ (pCD1Ap). Only 3 mice could survive from pneumonic challenge during 15 days observation.

Figure 4B:
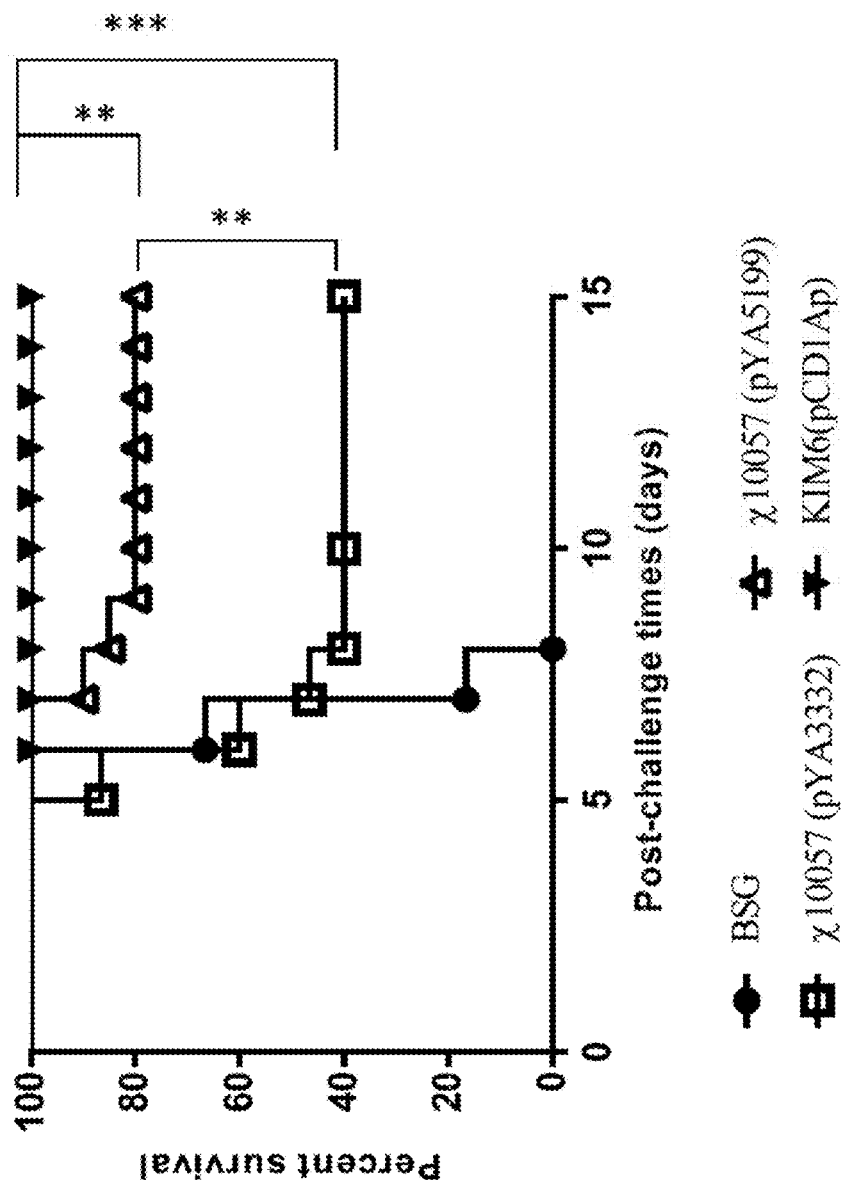

In addition, a single dose of χ10057 (pYA5199) administered orally provided 80% protection against an s.c. challenge of $1.1 \times 10^5$ CFU of KIM6+ (pCD1Ap). Immunization with χ10057 (pYA3332) provided partial protection with 40% survival for s.c. challenge, but its protective efficacy was significantly lower than that induced by χ10057 (pYA5199). Immunization with *Y. pestis* KIM5 (Pgm−) as a positive control provided complete protection against s.c. challenge of *Y. pestis*. None of the mice immunized with BSG were protected (FIG. 4B).

Example 6

Figure 5A:
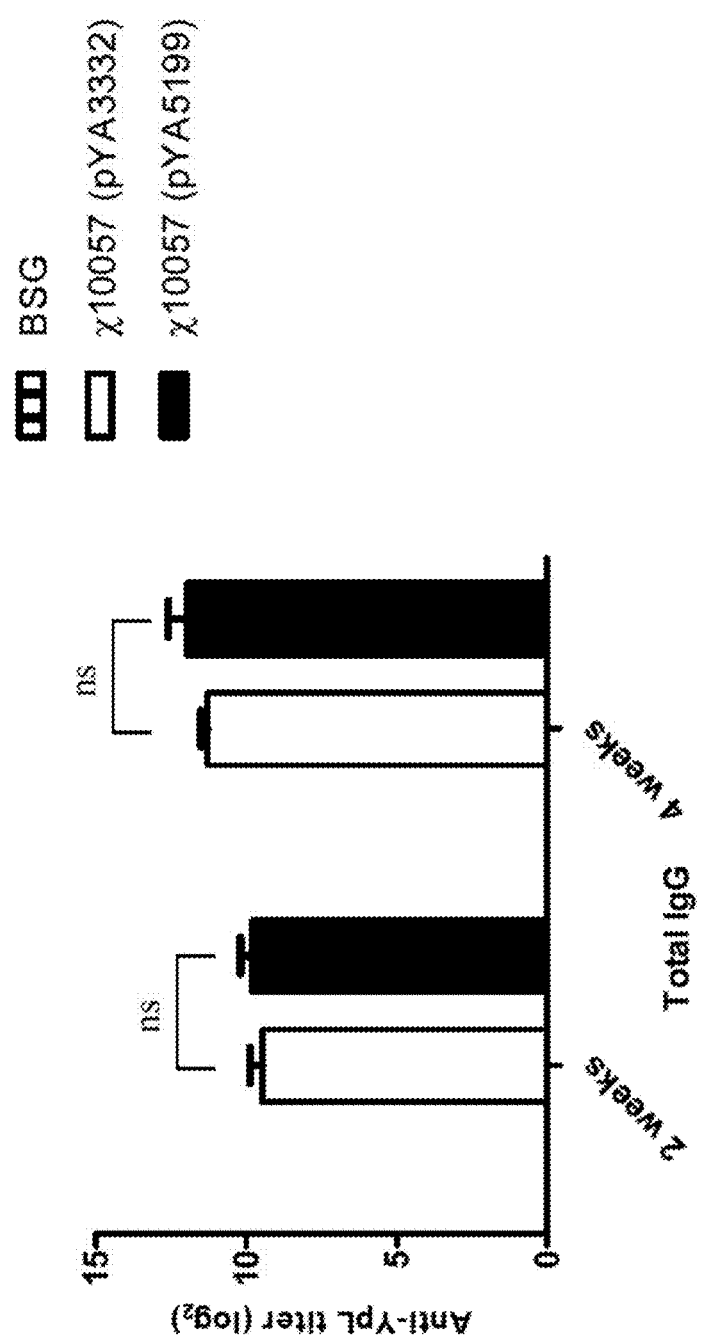
Figure 5B:
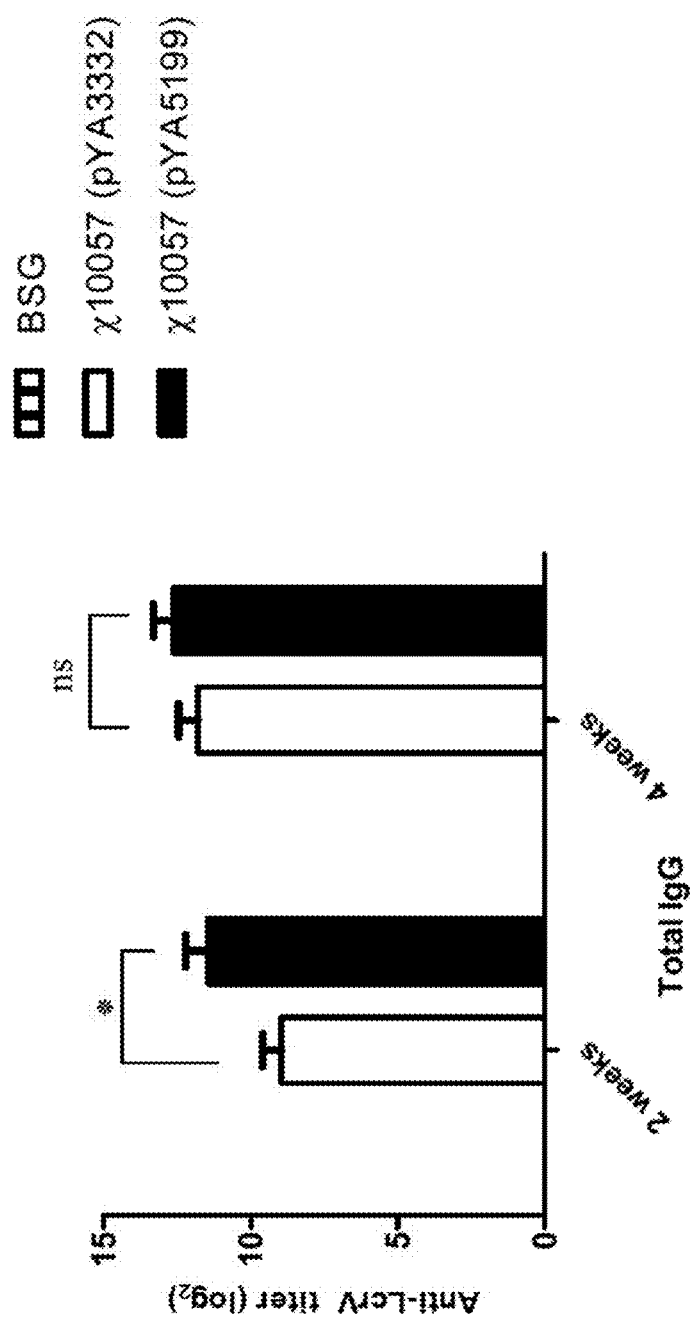
Figure 5C:
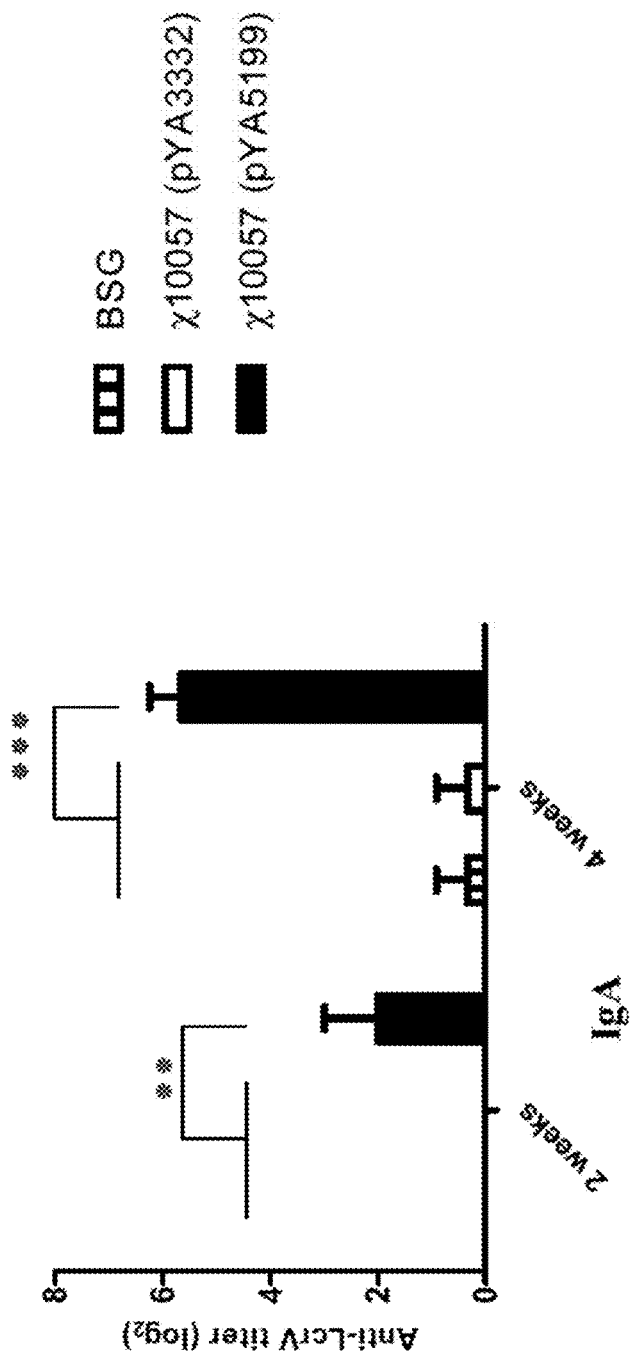

Antibody Responses in Mice Orally Immunized with the Recombinant *Y. pseudotuberculosis* Strains Measurement of total IgG responses to YpL indicated that the levels of anti-YpL titers were similar when induced by χ10057 (pYA3332) and χ10057 (pYA5199) by week 2 and were further elevated by week 4 to similar levels (FIG. 5A). The anti-YpL titers from both strains were significantly higher than in the BSG immunized group (p<0.001) (FIG. 5A). The IgG titers of anti-LcrV were slightly higher in mice immunized with χ10057 (pYA5199) than with χ10057 (pYA3332) by week 2 (FIG. 5 B). The anti-LcrV titers induced by χ10057 (pYA3332) and χ10057 (pYA5199) were elevated to similar levels in mice immunized with either strain by week 4.

Live attenuated vaccines administered by the oral route can generate mucosal immune responses, in addition to effective development of humoral immune responses (Ogra et al., 2001). Here, we looked at secretory IgA (sIgA) to LcrV in vaginal washes of mice orally immunized with χ10057 (pYA5199) and χ10057 (pYA3332). The measurement of sIgA indicated that only χ10057 (pYA5199)-immunized mice produced significant levels of anti-LcrV IgA at week 2 (p<0.01) and week 4 (p<0.001), while the χ10057 (pYA3332) or BSG-immunized mice did not produce any levels of anti-LcrV IgA (FIG. 5 C).

Figure 6A:
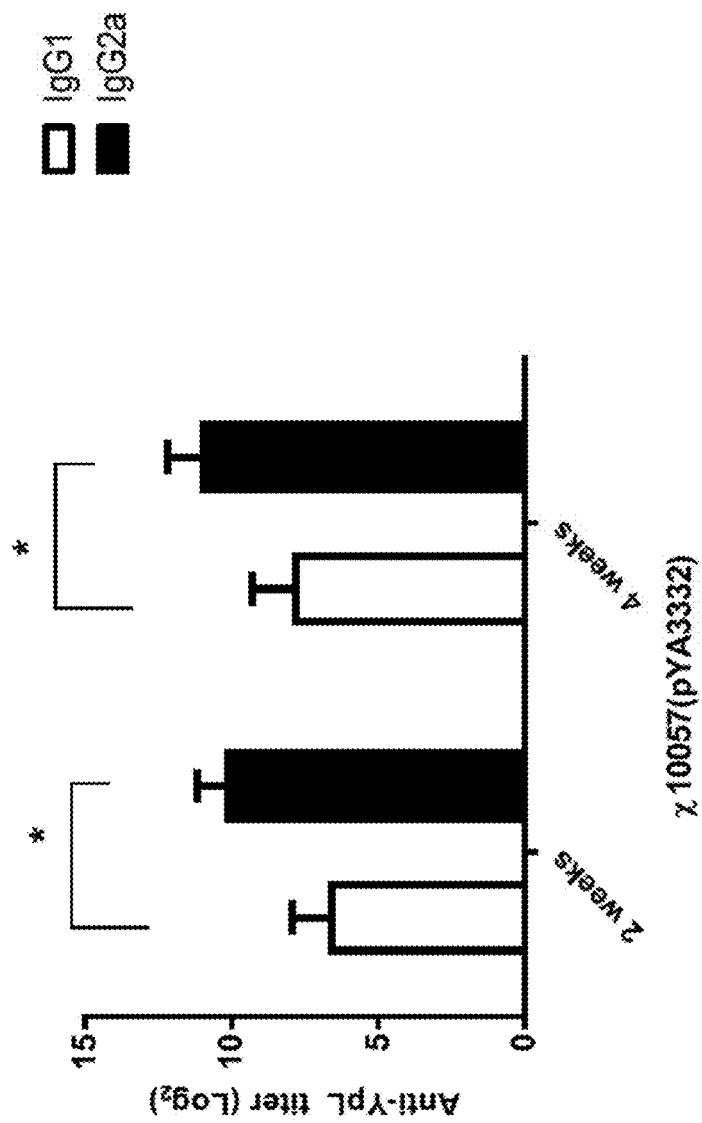
FIG. 6B depicts IgG1 and IgG2a antibody levels to YpL in sera of mice orally immunized with χ10057 (pYA5199). The sera from 12 mice were individually analyzed and the experiments were performed twice with consistent results. *, P<0.05.
FIG. 6C depicts IgG1 and IgG2a antibody levels to recombinant LcrV in sera of mice orally immunized with χ10057 (pYA3332). The sera from 12 mice were individually analyzed and the experiments were performed twice with consistent results. *, P<0.05.
FIG. 6D depicts IgG1 and IgG2a antibody levels to recombinant LcrV in sera of mice orally immunized with χ10057 (pYA5199). The sera from 12 mice were individually analyzed and the experiments were performed twice with consistent results. *, P<0.05.
Figure 6B:
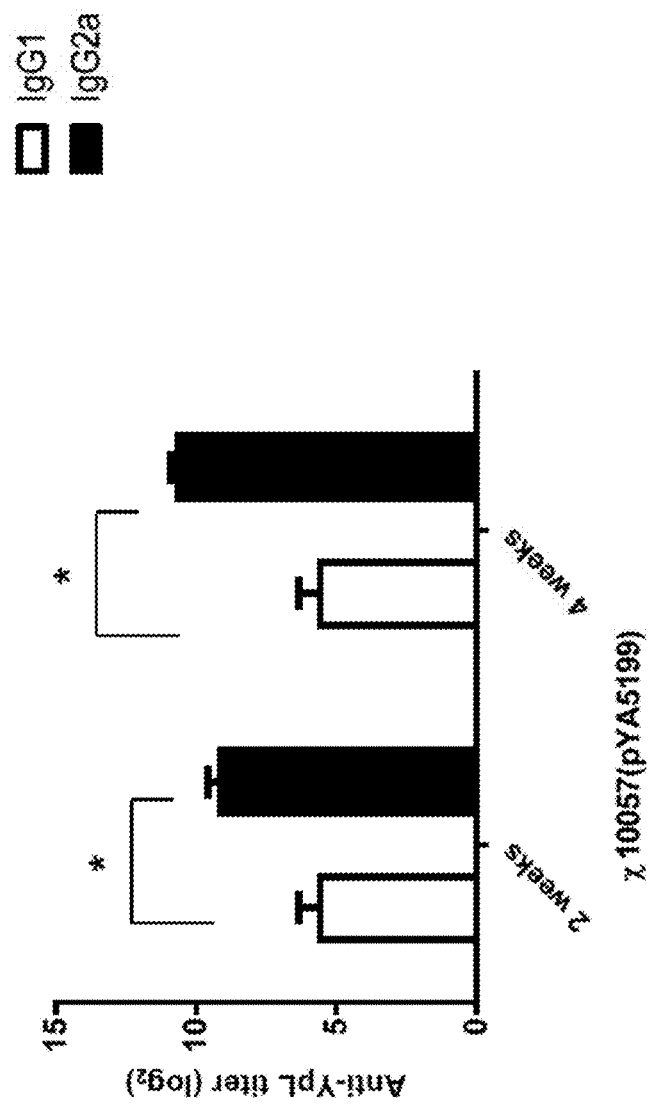
Figure 6C:
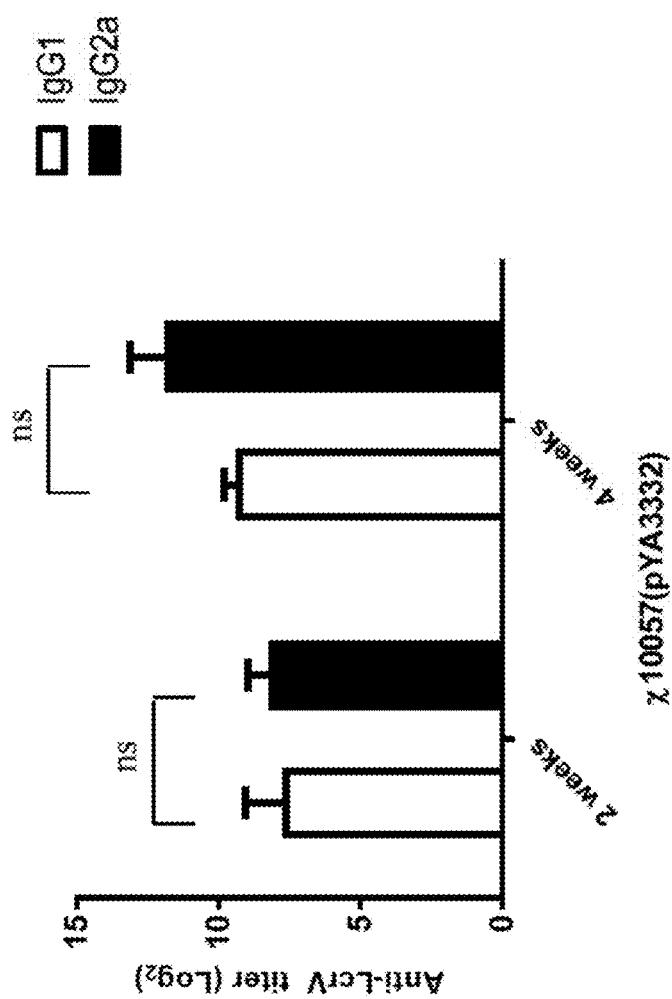
Figure 6D:
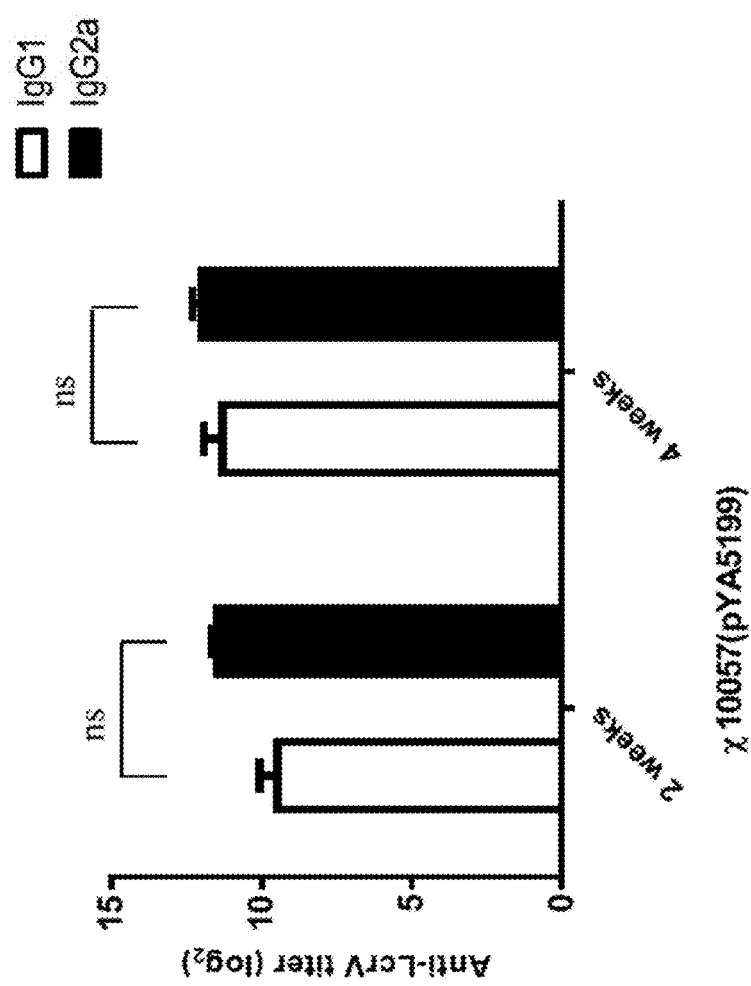

We also measured titers of IgG subtypes (IgG1 and IgG2a) in sera from mice immunized with χ10057 (pYA3332) and χ10057 (pYA5199). The levels of anti-YpL IgG1 and IgG2a isotype antibodies rapidly increased after vaccination at 2 weeks and gradually increased at 4 weeks. At 2 and 4 weeks post-immunization with χ10057 (pYA3332), the ratio of IgG1 to IgG2a to YpL was 0.65:1 and 0.7:1, respectively. Similarly, the ratio of IgG1 to IgG2a to YpL was 0.6:1 and 0.65:1 in mice at 2 and 4 weeks post-immunization with χ10057 (pYA5199), respectively (FIGS. 6A and B). The results indicated that Th1 biased response to YpL was primed by both χ10057 (pYA3332) and χ10057 (pYA5199). The level of anti-LcrV IgG1 and IgG2a antibodies also rapidly increased after vaccination at 2 weeks and increased slightly at 4 weeks post-immunization. But the ratio of IgG1 to IgG2a was very close to 1 in mice immunized with χ10057 (pYA3332) and χ10057 (pYA5199), respectively (FIGS. 6C and D).

Example 7

Cellular Immune Response in Mice Orally Immunized with χ10057 (pYA5199)

Several reports have demonstrated that protection against pneumonic plague is known to require cell mediated immunity and also the type 1 cytokines IFN-γ and TNF-α (Parent et al., 2005, Parent et al., 2006). IL-17 also contributes to cell-mediated defense against pulmonary *Y. pestis* infection (Lin et al., 2011). So, we looked at these three important cytokines. To evaluate cellular immune responses induced by the recombinant vaccine strains by examining production of IFN-γ, TNF-α and IL-17 after immunization, we orally vaccinated Swiss Webster mice (4/group) with $10^9$ CFU of χ10057 (pYA3332) or χ10057 (pYA5199), and with BSG as a negative control. At 21 days after the initial vaccination, splenocytes isolated from the BSG, χ10057 (pYA3332) or χ10057 (pYA5199)-immunized mice were stimulated for 72 hours with 4 μg/ml of LcrV, 4 μg/ml of YpL, 1 μg/ml of concanavalin A (Con A) as the positive control or media (RPMI1640) as the negative control. The supernatants of the cultures were collected and analyzed by a mouse multiplex assay with BioPlex (Bio-Rad). Results showed that splenic cells from mice vaccinated with χ10057 (pYA5199) produced significantly higher levels of IFN-γ, TNF-α and IL-17 in response to restimulation with the LcrV antigen than those observed for χ10057 (pYA3332), while cells from the BSG-immunized mice did not produce these cytokines (FIGS. 7A, B & C).

These results suggested that immunization with a *Y. pseudotuberculosis* strain delivering LcrV via T3SS could elicit an LcrV-specific cellular immune response. Splenic cells from mice vaccinated with χ10057 (pYA5199), χ10057 (pYA3332) or BSG also produced similar cytokine profiles to YpL restimulation, but the levels of IFN-γ, TNF-α and IL-17 produced from YpL stimulation was significantly lower than that of LcrV stimulation (FIGS. 7A, B & C). In addition, production of IL-4 in supernatant of cell cultures was measured, but the levels of IL-4 were very low in all samples (FIG. 8A). We compared the levels of IFN-γ with IL-4 in the supernatant of splenic cells stimulated with LcrV in vitro. The ratio of IFN-γ to IL-4 from the group of mice receiving χ10057 (pYA5199) immunization was significantly higher than in groups of mice receiving BSG and χ10057 (pYA3332) (FIG. 8B). The results suggested that the immune response elicited by immunization with χ10057 (pYA5199) had a Th1 bias.

Materials and Methods for Examples 1-7

Media and Reagents. Tryptone, yeast extract, tryptose blood agar (TBA) and heart infusion broth (HIB) were from Difco. Diaminopimelic acid (DAP) and L-arabinose were from Sigma (St. Louis, Mo.). Oligonucleotides were from IDT (Coralville, Iowa). Restriction endonucleases were from New England Biolabs (Ipswich, Mass.). Taq DNA polymerase (New England Biolabs) was used in all PCR tests. Vent DNA polymerase (New England Biolabs) was used to amplify fragments for cloning. T4 ligase was from Promega (San Luis Obispo, Calif., USA). Qiagen products (Hilden, Germany) were used to isolate plasmid DNA, gel-purify fragments or purify PCR products.

Bacterial Strains, Plasmids, and Culture Conditions. All bacterial strains and plasmids used in this study are listed in Table 1. All strains were stored at −70° C. in peptone-glycerol. *Escherichia coli* χ6212 was used as an intermediate host for cloning procedures and grown routinely at 37° C. in LB broth (Bertani, 1951) or on LB solidified with 1.2% Bacto Agar (Difco). The *Y. pseudotuberculosis* PB1+ strain provided by Robert Perry (University of Kentucky) and used in this study was grown in LB medium at 27° C. When required, chloramphenicol (50 μg/ml, Cm), arabinose (0.1%) or 2,6-diaminopimelic acid (DAP, 15 μg/ml) was added. TBA containing 5% sucrose was used for sacB gene-based counterselection in allelic exchange experiments. *Y. pestis* KIM6+ (pCD1Ap) was used for challenge studies as previously reported (Sun, 2011). *Y. pestis* cells were grown routinely on Congo red agar from peptone-glycerol stocks and in HIB at 28° C. (Straley & Bowmer, 1986). HIB Congo red agar plates were used to confirm the pigmentation (Pgm) phenotype of *Y. pestis* strains (Gong et al., 2001).

Construction of plasmids. All primers used in this study are listed in Table 3. The sycE-yopE (1-138aa) (designated as sycE-yopE$_{Nt138}$) gene fragment was amplified from *Y. pestis* using primers 1 and 2. The full-length lcrV gene was amplified from *Y. pestis* using primers 3 and 4. Then the sycE-yopE$_{Nt138}$ gene fragment was fused with the full-length lcrV through overlapping PCR using primers 1 and 4. The fused fragment, sycE-yopE$_{Nt138}$-lcrV, was cloned into the BspEI and HindIII sites of pYA3332 (p15A ori) to form plasmid pYA5199 (yopE$_{Nt138}$-lcrV) (Table 1), which specifies synthesis of YopE$_{Nt138}$-LcrV.

TABLE 3

| Oligonucleotides used in this work | | |
|---|---|---|
| Name | Sequence | Seq. ID No. |
| Primer1 | 5' cggtccggagacattactaagtgagcgt tgta 3' (BspEI) | 1 |
| Primer2 | 5' gttttgttcgtaggctctaatcatcgta gcgaactgatcatgattttctg 3' | 2 |

TABLE 3 -continued

Oligonucleotides used in this work

| Name | Sequence | Seq. ID No. |
|---|---|---|
| Primer3 | 5' gaaaaatcatgatcagttcgctacgatg attagagcctacgaacaaaaccca 3' | 3 |
| Primer4 | 5' cggaagctttcatttaccagacgtgtca tcta 3' (HindIII) | 4 |
| MsbB1 | 5' cggggtacccgtattgcgccgcataaag g 3' (KpnI) | 5 |
| MsbB2 | 5' ctgagctcggcagcctgcagagccatct acgatgggctgacagactg 3' | 6 |
| MsbB3 | 5' ctctgcaggctgccgagctcagacgccg taaatacatccatgtagg 3' | 7 |
| MsbB4 | 5' cggggtacctgcggcaaaccacctcaaa g 3' (KpnI) | 8 |
| MsbB-K-12-F | 5' cgggagctcttgaacttatcatcaggcg aaggcct 3' (SacI) | 9 |
| MsbB-K-12-R | 5' cggctgcaggctttccggtaataccgga c 3' (PstI) | 10 |
| Pcrp-F | 5' cggcccgggctgatagatcaactgcgcg ctcca 3' (XmaI) | 11 |
| Pcrp-R | 5' cggggtacccttaacgggtgccgtaaac gacga 3' (KpnI) | 12 |
| Asd-1 | 5' cggggtaccagcaacacagttgccgcaa tcatctc 3' (KpnI) | 13 |
| Asd-2 | 5' acgctatgcgccgctaaaaaatagtgtt tactgccctgccttggaagg 3' | 14 |
| Asd-3 | 5' cagggcagtaaacactattttttagcgg cgcatagcgtgtcatatcgt 3' | 15 |
| Asd-4 | 5' cggcccgggctatagtatgcccgtccgg tttcatcc 3' (XmaI) | 16 |

The restriction endonuclease sites are underlined.

For construction of suicide vectors, primers MsbB1/MsbB2 and MsbB3/MsbB4 (Table 3) were used for amplifying flanking regions of the msbB gene from *Y. pseudotuberculosis* PB1/+, respectively. Then the DNA fragment containing the ΔmsbB was amplified using primers MsbB1/MsbB4 through overlapping PCR. The fused DNA segment (ΔmsbB) was ligated into the KpnI site of pRE112 to form plasmid pYA5151. In order to replace the msbB gene of *Y. pseudotuberculosis* PB1/+ by the msbB gene of *E. coli* K-12, the msbB gene with its native promoter of *E. coli* K-12 ($P_{msbB}$ (EC) msbB(EC)) was amplified using primers MsbB-K-12-F/MsbB-K-12-R (Table 3). The segment of $P_{msbB}$ (EC) msbB(EC) was cloned into the PstI and SacI sites between the flanking regions of ΔmsbB in pYA5151 to form plasmid pYA5152. The segment of $\Delta P_{crp}$::TT araC $P_{BAD}$ crp was amplified from plasmid pYA4581 (52) using primers Pcrp-F/Pcrp-R (Table 3) and cloned into the KpnI and XmaI sites of pRE112 to form plasmid pYA5153. To delete the asd gene from *Y. pseudotuberculosis* PB1/+, primers Asd1/Asd2 and Asd3/Asd4 (Table 3) were used for amplifying flanking regions of the Δasd gene, respectively. Then the DNA fragment containing the Δasd was amplified using primers Asd1/Asd4 through overlapping PCR. The fused flanking region (Δasd) was ligated into the KpnI and XmaI sites of pRE112 to form plasmid pYA5154. All the plasmid constructions were verified through sequencing.

Construction of *Y. pseutuberculosis* Mutants. To replace the $msbB_{(Ypt)}$ by the $msbB_{(EC)}$, the ΔmsbB868 mutation in *Y. pseudotuberculosis* encompasses a 1295 base pair deletion from the 162 base pairs before the ATG start codon to 170 base pairs behind of the TAG stop codon of msbB. The suicide plasmid pYA5151 (ΔmsbB) was conjugationally transferred from *E. coli* χ7213 (Kang et al., 2002) to the *Y. pseudotuberculosis* PB1/+ wild-type strain. Single-cross-over insertion strains were isolated on TBA agar plates containing Cm. Loss of the suicide vector after the second recombination between homologous regions (i.e., allelic exchange) was selected by using the sacB-based sucrose sensitivity counter-selection system (Sun et al., 2008). The colonies were screened for $Cm^s$ and verified by PCR using primers MsbB1/MsbB4. The mutant strain was designated χ10052 (ΔmsbB868). Then, χ10052 was conjugated with χ7213 harboring the suicide plasmid pYA5152 (Δmsbb::$P_{msbB\ (EC)}$ $msbB_{(EC)}$) to transfer ΔmsbB868::$P_{msbB\ (EC)}$ $msbB_{(EC)}$ into χ10052. Through the same screening procedure, mutant strain χ10053 (ΔmsbB868::$P_{msbB\ (EC)}$ $msbB_{(EC)}$) was confirmed. Following, the $\Delta P_{crp21}$::TT araC $P_{BAD}$ crp was introduced into χ10053 through the same procedure to construct mutant strain χ10055 ($\Delta P_{crp21}$::TT araC $P_{BAD}$ crp ΔmsbB868::$P_{msbB\ (EC)}$ $msbB_{(EC)}$). Finally, the ΔasdA206 defined deletion was introduced into χ10055 through conjugation of χ7213 (pYA5154) (ΔasdA206) with χ10055 to form χ10057. The colonies were confirmed for $Cm^s$, growth only in presence of DAP and by PCR using primer set Asd1/4. All the mutant strains were confirmed by DNA sequence analysis.

Analysis of Synthesis and Secretion of the Recombinant Proteins. To analyze the production and secretion of the chimeric proteins through T3SS, secreted proteins were prepared by using a modification of previously described methods (Kim et al., 2007). Cultures of *Y. pseudotuberculosis* χ10057 harboring pYA5199 ($yopE_{Nt138}$-lcrV) or pYA3332 (empty plasmid) were grown overnight in LB broth supplemented with 0.05% arabinose at 26° C. and subcultured into calcium-chelated medium (1% tryptone, 0.5% yeast extract, 50 mM MOPS [pH 7.0], 16 mM sodium oxalate, 160 mM magnesium chloride). Cultures were incubated for 6 h at 37° C. on a roller drum to provide mild aeration. The $OD_{600}$ of cultures was measured, and bacterial cell pellets were collected by centrifugation. The pellets were suspended in SDS loading buffer. The volume of sample buffer was adjusted based on the $OD_{600}$ to normalize the amount loaded on SDS-PAGE gel. Whole bacterial cells were lysed by heating at 95° C. for 5 min. Culture supernatants were concentrated by precipitation with 10% (w/v) trichloroacetic acid overnight at 4° C. and collected by centrifugation. Pellets were washed with ice-cold acetone and dissolved in 0.05 M Tris-HCl buffer (pH 9.5). Samples were heated at 95° C. for 5 min and separated by SDS-PAGE and blotted onto nitrocellulose membranes. The membranes were probed with rabbit anti-LcrV antibodies as described (Branger et al., 2007).

Translocation of Fusion Protein $YopE_{Nt138}$-LcrV. The translocation assays were conducted according to the procedures described previously (Collazo & Galan, 1997) with minor modifications. Briefly, HeLa cells ($5\times10^5$) were seeded into 100 mm tissue culture dishes in Dulbecco modified Eagle medium (DMEM) supplemented with 10% fetal bovine serum and grown to 80-90% confluence. Prior to infection, the cells were washed twice with 5 ml of Dulbecco's Phosphate Buffered Saline (DPBS). Antibiotic-free medium containing 0.5 μg/ml cytochalasin D was added. Overnight bacterial cultures were diluted 1:20 in HIB and incubated for 30 min at 26° C. followed by 1 h at 37° C. HeLa cells were infected with the bacteria at a multiplicity of infection (MOI) of 50 for 4 h at 37° C. Subsequently, the culture medium was removed, and the cells were washed three times with 10 ml DPBS. The HeLa cells were treated with 10 µg/ml proteinase K in DPBS for 15 min at 37° C. to digest secreted but not translocated bacterial protein. Afterwards, 3 ml of chilled HBSS containing 2 mM phenylmethylsulfonyl fluoride (Sigma) was added. Cells detached during the proteinase K treatment and were subsequently collected by low-speed centrifugation (600×g for 10 min) and lysed in 1 ml of DPBS containing 0.1% Triton X-100, 10 µg/ml DNase, 10 µg/ml RNase, 1 mM PMSF, 0.1% (v/v) protease inhibitor (P-8340) and 0.01% (v/v) phosphatase inhibitor (P-2850) cocktails (Sigma-Aldrich), and then incubated for 15 min at 4° C. Then the cell lysates were centrifuged at 12,500×g for 30 min at 4° C., and the pellet obtained (P), containing the unbroken cells, membranes, and bacteria that had adhered and had been internalized were resuspended in 200 µl of LDS sample buffer (Pierce ECL, Rockford, Ill.). The supernatant of the cytoplasmic fraction (C) containing the eukaryotic cytoplasm and the translocated recombinant proteins was filtered through a 0.22 µm-pore-size syringe filter (Millipore) and proteins precipitated with 10% trichloroacetic acid and resuspended in 200 µl of LDS sample buffer. Samples were heated at 95° C. for 5 min and separated by SDS-PAGE and blotted onto nitrocellulose membranes. The chimeric proteins were identified using rabbit anti-LcrV antibody and followed by peroxidase-conjugated goat anti-rabbit antibody (Sigma, St. Louis, USA). Bound antibodies were detected by enhanced chemiluminescent detection system (Pierce ECL, Rockford, Ill.).

Animal Experiments Six-week-old, female Swiss Webster mice were purchased from Charles River Laboratories (Wilmington, Mass.). All animal procedures were approved by the Arizona State University Animal Care and Use Committee. Mice were acclimated for one week after arrival and deprived of food and water for 6 h before starting experiments. The median lethal dose ($LD_{50}$) of the $Y.$ $pseudotuberculosis$ strains in mice was determined according to previous procedures with certain modifications (Kong et al., 2011, Wang et al., 2011c, Zhang & Bliska). Overnight cultures of bacteria were grown at 26° C. in LB supplemented with 0.05% arabinose when needed. The next day, 1 ml of this culture was inoculated into 50 ml of the appropriate media and grown with aeration at 26° C. to an optical density at 600 nm ($OD_{600}$) of 1.0. Bacteria were harvested by centrifugation at 24° C. and resuspended in 0.5 ml buffered saline with gelatin (BSG). Five mice per group were orally inoculated with approximately $10^7$, $10^8$ or $10^9$ CFU of bacteria in 20 µl of BSG by placing pipette tip behind the incisors of mice. Actual numbers of colony-forming units (CFU) inoculated were determined by plating serial dilutions onto LB agar. The experiment was repeated, and data were combined to calculate the $LD_{50}$.

To evaluate colonization, 3 mice per group were euthanized on days 3, 6 and 9 after inoculation. Spleen, liver and Peyer's patches (PPs) were collected and weighed, and BSG buffer (Wang et al., 2011c) was added to a final volume of 1 ml. Samples were homogenized and plated onto MacConkey agar supplemented with 1% lactose to determine the number of viable bacteria. The detection limit was 2 CFU. For representation in graphic and statistical analysis, $log_{10}$ was applied to the values, and recovery of 0 CFU was reported as 1 CFU/g. The experiment was done twice, and data were combined to calculate colonization titers.

To evaluate immunogenicity of vaccine strains, strain χ10057 harboring plasmid pYA5199 (yopE$_{Nt138}$-lcrV) or pYA3332 (empty plasmid) were prepared as described above. Food and water were restricted for 6 h, and then 10 mice per group were orally inoculated with 20 µl of BSG containing $1 \times 10^9$ CFU of each strain or BSG as negative control on day 0. Blood was obtained by mandibular vein puncture at biweekly intervals, and serum was collected individually after centrifugation. The vaginal tract of each mouse was washed with 100 µl BSG, and the secretory IgA in wash fluids was analyzed individually. The immunogenicity of vaccine strains was evaluated by determining the titers of antibodies in serum or vaginal wash against LcrV (Branger et al., 2010) and $Y.$ $pestis$ whole cell lysates (YpL) (Sun et al., 2009) by enzyme-linked immunosorbent assay (ELISA) as described previously (Kang et al., 2002).

Determination of Protective Efficacy. A single colony of $Y.$ $pestis$ KIM6+ (pCD1Ap) was inoculated into HIB medium supplemented with 25 µg/ml ampicillin and grown overnight at 26° C. Bacteria were diluted into 10 ml of fresh HIB enriched with 0.2% xylose and 2.5 mM $CaCl_2$ and supplemented with 25 µg/ml ampicillin to obtain an $OD_{620}$ of 0.1 and incubated at 26° C. for subcutaneous (s.c.) challenge (bubonic plague) or 37° C. for intranasal (i.n.) challenge (pneumonic plague). Cultures were grown to an $OD_{620}$ of 0.6. The cells were then harvested, and the pellet resuspended in 1 ml of isotonic PBS. Groups of Swiss Webster mice (10/group) were orally immunized with $10^9$ CFU of χ10057 containing different plasmids. One group of mice (5/group) was orally vaccinated with BSG as controls. On day 35 after initial immunization, animals were either challenged s.c. with $Y.$ $pestis$ KIM5+ at $1.1 \times 10^5$ CFU in 100 µl PBS or lightly anesthetized with a 1:5 xylazine/ketamine mixture were challenged intranasally with $1 \times 10^4$ CFU $Y.$ $pestis$ KIM6+ (pCD1Ap) in 20 µl PBS. All infected animals were observed over a 15-day period for the development of signs of plague infection.

Measurement of Antibody Responses. An enzyme-linked immunosorbent assay (ELISA) was used to assay antibodies in serum to LcrV of $Y.$ $pestis$ (Sun & Curtiss, 2012) or YpL ($Y.$ $pestis$ whole cell lysate) (Sun et al., 2009). Polystyrene 96-well flat-bottom microtiter plates (Dynatech Laboratories Inc., Chantilly, Va.) were coated with 100 ng/well of purified rLcrV of $Y.$ $pestis$ or YpL. Antigens suspended in sodium carbonate bicarbonate coating buffer (pH 9.6) were applied with 100 µl volumes in each well. The coated plates were incubated overnight at 4° C. The procedures for measuring antibody titer were described in our previous report (Branger et al., 2010). Absorbance readings that were 0.1 higher than PBS control values were considered positive.

Analysis of T Cell Activation by Measuring Cytokine Production. Spleens taken aseptically from euthanized animals were dissociated using cell strainers (BD Biosciences). The spleen cell suspensions were depleted of red blood cells (RBC) using RBCs lysis buffer (Sigma) and splenocytes were extensively washed with cold PBS. Cells resuspended in RPMI 1640+Glutamax™ (Gibco) supplemented with 5% fetal bovine serum and 100 µg/ml penicillin/streptomycin were seeded in 96 well plates ($1 \times 10^6$/well) and stimulated with either YpL antigen (4 µg/ml), the LcrV antigen (4 µg/ml) or Concanavalin A (Con A) (1 µg/ml; Sigma) as a control. After three days, the supernatant was collected and was measured for cytokine content using a multiplex assay with BioPlex (Bio-Rad).

Statistical Analysis. The log-rank test was used for analysis of the survival curves. Data are expressed as means±SE. Two-tailed t-test was used for statistical analyses of spleen weight. Two-way ANOVA was used for cytokine analysis. A P-value of <0.05 was considered significant.

Examples 8-13

Example 8

Construction of *Y. pseudotuberculosis* Mutants that Synthesize F1 by Temperature Regulation Since the F1 antigen encoded by the caf1 locus has been identified as one of major antigens that induce protection against *Y. pestis*, we tried to express recombinant F1 in Yptb to improve the immunogenicity of *Y. pseudotuberculosis* constructs. However, we have observed that high levels of F1 were synthesized at both 28° C. and 37° C. in Yptb harboring a pSC101 or p15A plasmid containing the caf1 operon, which greatly reduced bacterial growth at both temperatures (FIGS. 9A and B).

Thus, we have tried to construct an attenuated *Y. pseudotuberculosis* mutant with a chromosomal insertion of the caf1 operon: χ10068 [ΔlacZ caf1R-caf1M-caf1A-caf1 pYV-ω2 (ΔyopJ ΔyopK)] (Table 1), which synthesizes F1 regulated by temperature as in *Y. pestis*. FIGS. 10 A & B demonstrates that the F1 antigen in χ10068 was synthesized only at 37° C., which means F1 will only be synthesized in mammals immunized with χ10068. In addition, FIG. 10C shows that insertion of the caf1 operon did not change the growth rate of χ10068 compared to wild-type *Y. pseudotuberculosis*.

Example 9

Construction of New *Y. pseudotuberculosis* Mutant as a Vector Delivering LcrV of *Y. pestis* Through TTSS YopJ (YopP in *Y. enterocolitica*), a cysteine protease, is an enzyme with acetyltransferase and deubiquitinase activities that counteracts the proinflammatory response in host cells by inhibiting the mitogen-activated protein kinase and NF-κB signaling pathways (Bliska, 2006, Orth, 2002, Orth et al., 2000, Zhou et al., 2005). Such inhibitory actions result in suppression of cytokine production and induction of macrophage apoptotic death (Aepfelbacher, 2004, Orth, 2002, Ruckdeschel, 2002, Zhang & Bliska, 2005). In addition, serine/threonine acetylation of TGFβ-activated kinase (TAK1) by *Y. pestis* YopJ inhibits innate immune signaling (Paquette et al., 2012). The $LD_{50}$ of a *Y. pestis* yopJ mutant was only 1.5-fold higher than the parental strain (Perry & Fetherston, 1997). The virulence of a *Y. pseudotuberculosis* yopJ mutant was reduced 64-fold in mice (Monack et al., 1998). A *Y. enterocolitica* yopJ mutant was also attenuated in an oral mouse infection assay (Trulzsch et al., 2004). Studies indicate that *Y. enterocolitica* YopP induces apoptosis in dendritic cells (Erfurth et al., 2004) and inhibits CD8 T cell priming in the mouse (Trulzsch et al., 2005). YopK was considered to control translocation of Yops effector, its activity has been shown to modulate the size of the translocation pore in red blood cells and epithelial cells (Holmstrom et al., 1997, Dewoody et al., 2011). YopK was proposed to remain associated with the translocation pore where it could suppress inflammasome activation (Brodsky et al.).

Thus, χ10069 [Δasd pYV-ω2 (ΔyopJ ΔyopK)] (Table 1) was constructed to enable use of a balanced-lethal Asd⁺ plasmid to facilitate stable antigen synthesis and enhance cellular immune responses. We also introduced pYA5199 into one of the vaccine strains, χ10069, to test synthesis, secretion, and translocation of $YopE_{Nt138}$-LcrV. Our results showed that $YopE_{Nt138}$-LcrV was synthesized in the bacteria and secreted into supernatant (FIG. 11A) without affecting their growth rate compared with *Y. pseudotuberculosis* and χ10069 (pYA3332) (data not shown). We also confirmed that the $YopE_{Nt138}$-LcrV could be injected into the cytosol of HeLa cells by T3SS (FIG. 11B). In addition, FIG. 11C shows that χ10069 harboring different plasmids had the same growth rates as wild-type *Y. pseudotuberculosis*.

Example 10

Virulence of Recombinant Strains in Mice

We infected Swiss Webster mice orally with $1.5 \times 10^9$ CFU of χ10068, $2.0 \times 10^9$ CFU χ10069 (pYA3332) (vector control) or $2.8 \times 10^9$ CFU of χ10069 (pYA5199) ($yopE_{Nt138}$-lcrV). All the mice infected with χ10068 and χ10069 harboring different plasmids showed a little weight loss but no any symptoms of disease. Thus, the $LD_{50s}$ of χ10068, χ10069 (pYA3332) and χ10069 (pYA5199) were more than $1.5 \times 10^9$ CFU (Table 4)

TABLE 4

Virulence of different *Y. pseudotubculosis* strain constructions

| Strains | Dose (CFU) | Route | Survivors/death |
|---|---|---|---|
| χ10068 | $1.5 \times 10^9$ CFU | Oral | 10/10 |
| χ10069 (pYA3332) | $2.0 \times 10^9$ | Oral | 10/10 |
| χ10069 (pYA5199) | $2.8 \times 10^9$ | Oral | 10/10 |
| BSG | — | Oral | 5/5 |

Example 11

Protection Against Plague Challenge in Mice Immunized with Recombinant Attenuated *Y. pseudotuberculosis* Strains Groups of mice (16 mice per group) were orally immunized with a single dose $1.5 \times 10^9$ CFU of χ10068, $2.4 \times 10^9$ CFU of χ10069 (pYA3332) or $2.9 \times 10^9$ CFU of χ10069 (pYA5199), and given BSG as the negative control. Mice were subcutaneously immunized with $2.5 \times 10^7$ CFU of *Y. pestis* KIM5 (Pgm⁻) as a standard attenuated *Y. pestis* vaccine and challenged intranasally with ~500 $LD_{50}$ ($5.0 \times 10^4$ CFU) of *Y. pestis* KIM6+ (pCD1Ap) at 35 days after initial immunization. Results showed that oral immunization with a single dose of χ10068 or χ10069 (pYA5199) both provided 93% protection against pneumonic plague, respectively (FIG. 12A). While the immunization of *Y. pestis* KIM5 (Pgm–) provided partial protection with 42%. Immunization with χ10069 (pYA3332) barely provided protection and none of the mice immunized with buffered saline with gelatin (BSG) were protected (FIG. 12A).

For evaluation of bubonic plague protection, groups of mice (10 mice per group) were orally immunized with a single dose $1.69 \times 10^9$ CFU of χ10068, $1.48 \times 10^9$ CFU of χ10069 (pYA3332) or $1.21 \times 10^9$ CFU of χ10069 (pYA5199), and given BSG as the negative control. Mice were subcutaneously immunized with $2.5 \times 10^7$ CFU of *Y. pestis* KIM5 (Pgm⁻) as a standard attenuated *Y. pestis* vaccine and challenged subcutaneously with $2.6 \times 10^5$ $LD_{50}$ ($2.5 \times 10^6$ CFU) of KIM6+ (pCD1Ap) at 35 days after initial immunization.

Immunization with χ10068, χ10069 (pYA3332) or χ10069 (pYA5199) provided 70%, 80%, or 70% protection, the immunization of *Y. pestis* KIM5 (Pgm−) as a positive control provided 90% protection against s.c. challenge of *Y. pestis*. None of the mice immunized with BSG were protected (FIG. 12B).

Example 12

Protection Against Yersiniosis in Mice Immunized with Recombinant Attenuated *Y. pseudotuberculosis* Strains Yersiniosis, a diarrheal illness, is typically a self-limiting disease in humans, mainly caused by *Y. enterocolitica* and *Y. pseudotuberculosis* which are transmitted via fecal-oral route from soil, water and a variety of animal food sources (Brubaker, 1991, Bottone, 1997). *Y. enterocolitica* has evolved into a more heterogeneous group, classified into 6 biogroups (Parkhill et al., 2001, Thomson et al., 2006) including biotype 1B, associated with human infection. Biotype 1B includes the most virulent serotype O8, primarily isolated in North America (Wauters et al., 1987, Bottone, 1997). Our long-term goal is to develop a *Y. pseudotuberculosis* strain as a vaccine or a recombinant vaccine specifying synthesis of one or more *Yersinia* antigens to protect against all pathogenic *Yersinia* species.

Figure 13B:
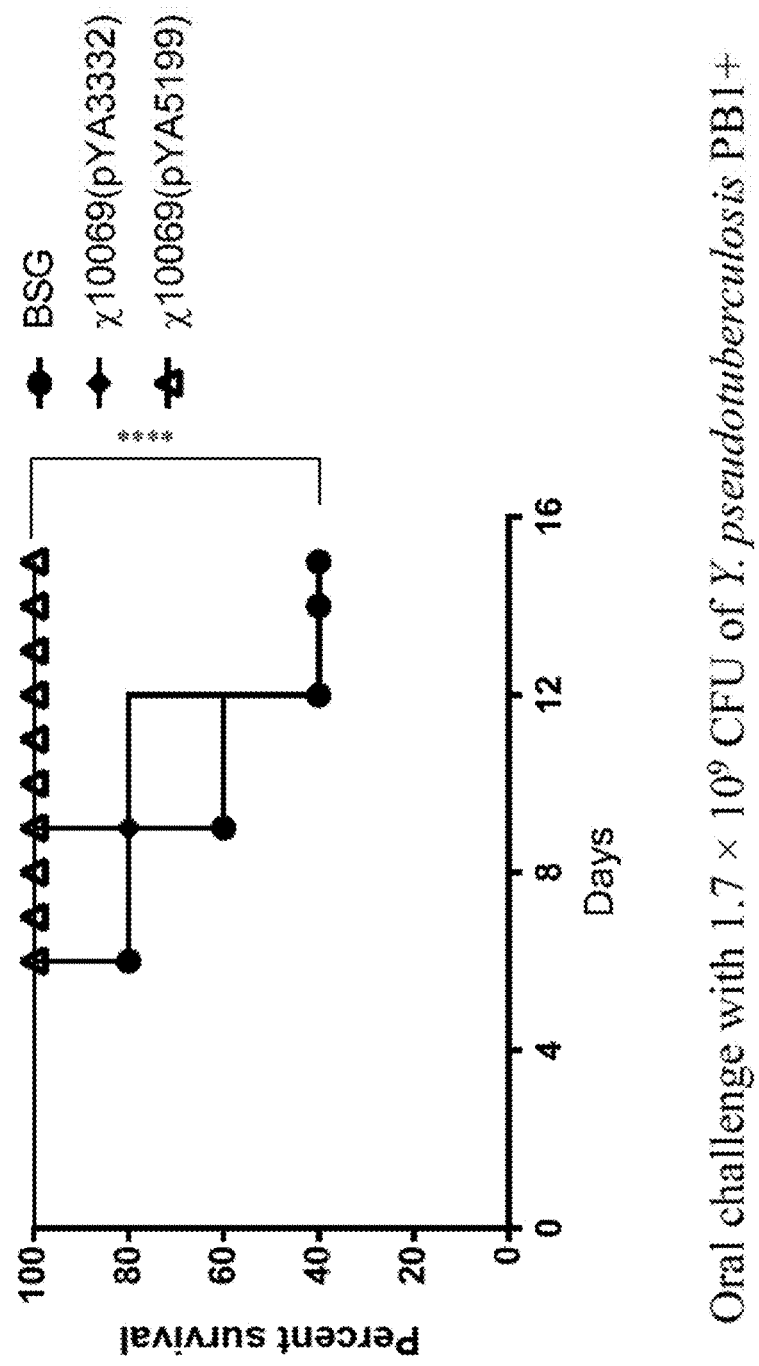

Therefore, we evaluated whether mice orally immunized with the χ10069 (pYA3332) or χ10069 (pYA5199) strain developed protection against challenge with *Y. enterocolitica* WA or *Y pseudotuberculosis* PB1+ (Table 1). Our results demonstrated that Swiss Webster mice orally immunized with one dose of $1.54 \times 10^9$ CFU of χ10069 (pYA5199) developed complete protection against oral challenge with $2.4 \times 10^9$ CFU of *Y. enterocolitica* WA or $1.7 \times 10^9$ CFU of *Y. pseudotuberculosis* PB1+ (FIGS. 13 A and B).

Example 13

Humoral and Cellular Responses in Immunized Mice

Figure 14A:
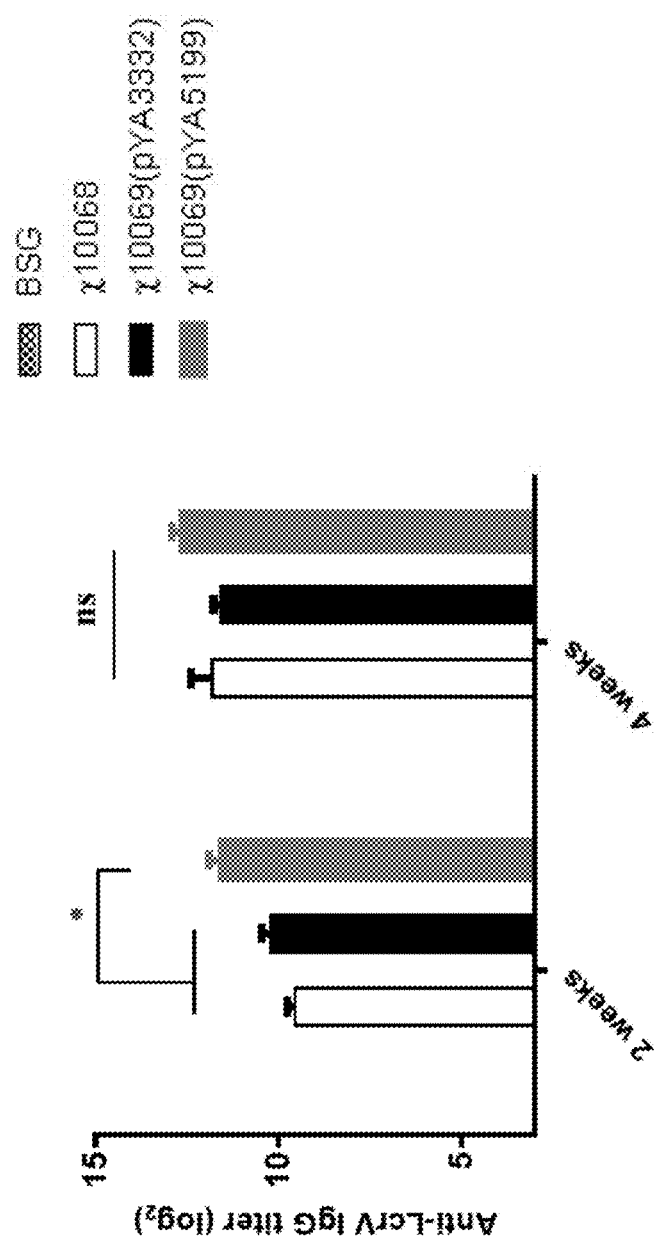
Figure 14B:
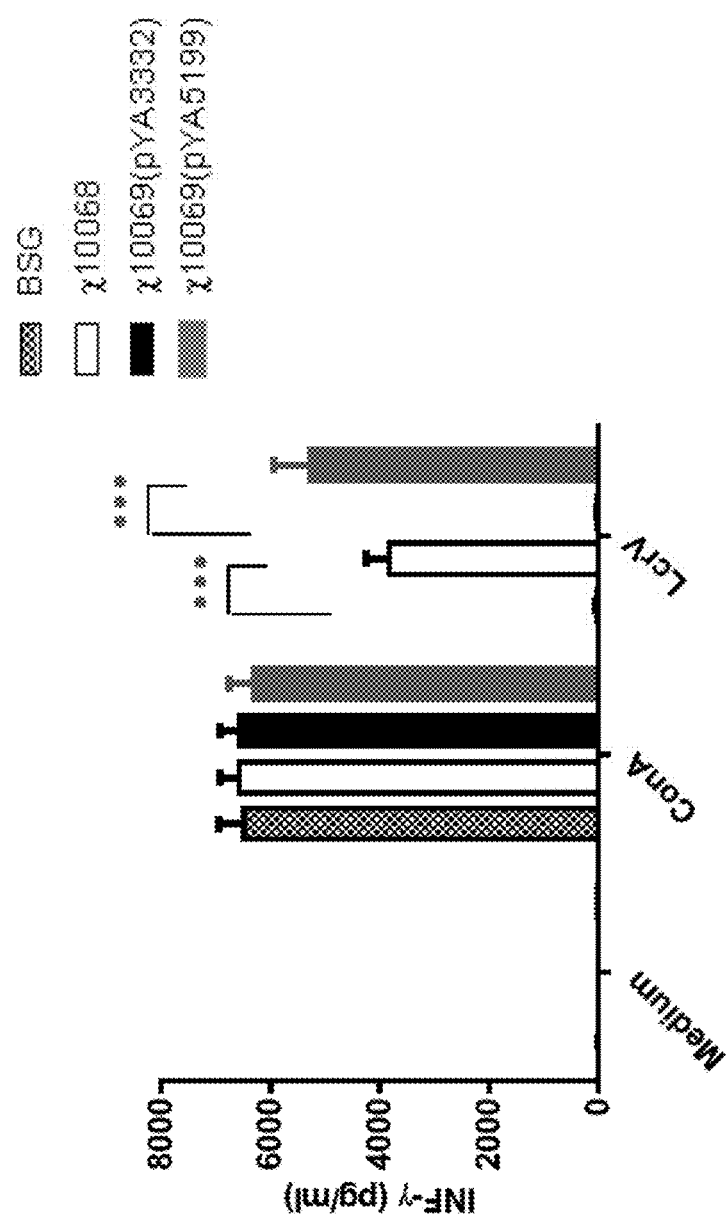
Figure 15A:
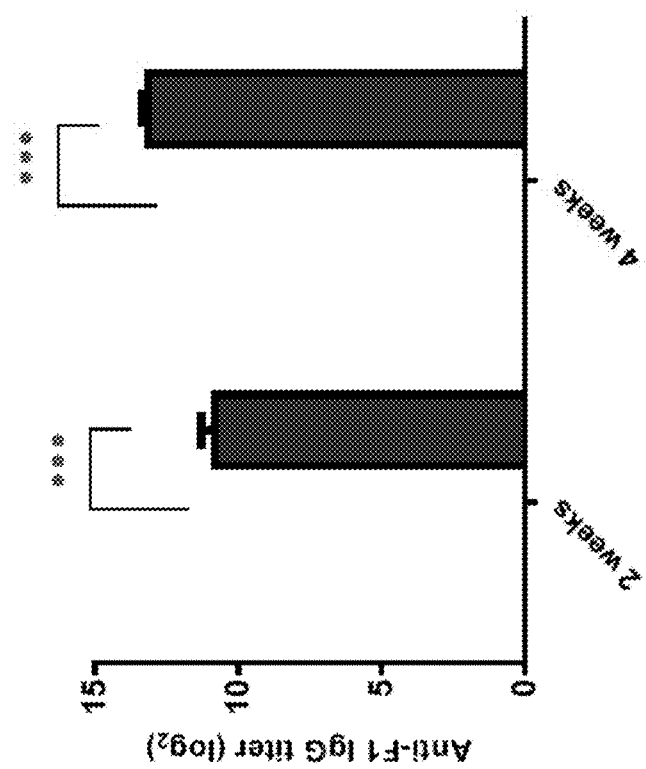
Figure 15B:
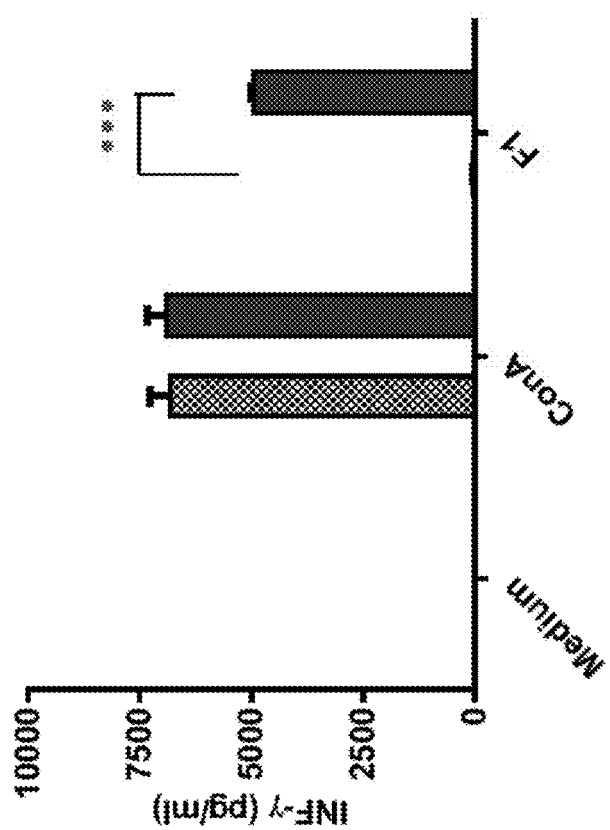
Figure 15C:
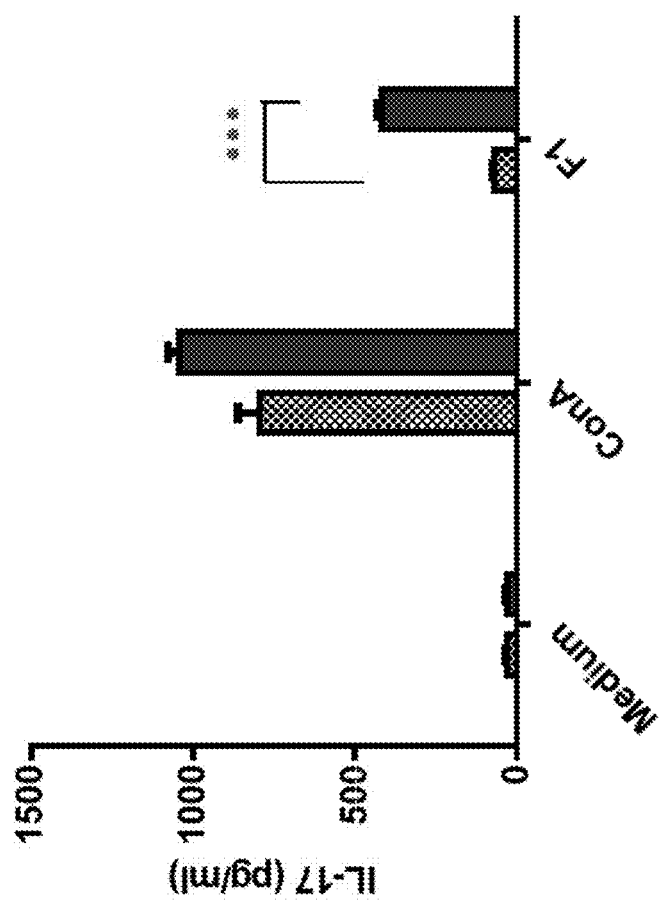
Figure 16A:
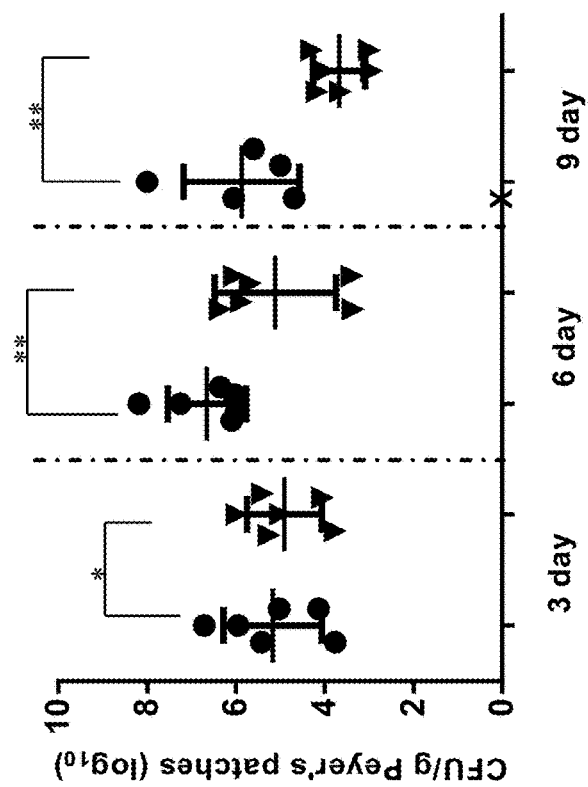
Figure 16B:
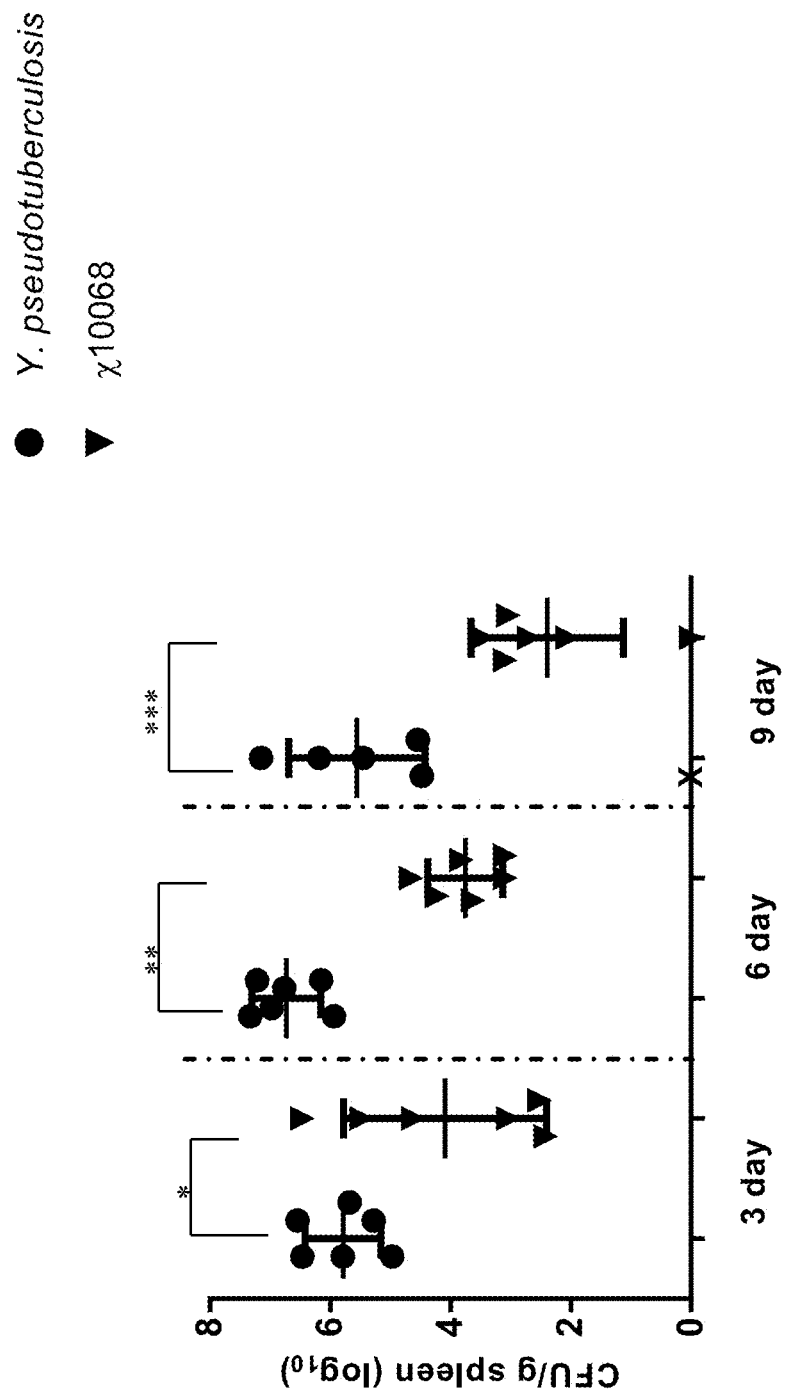
Figure 16C:
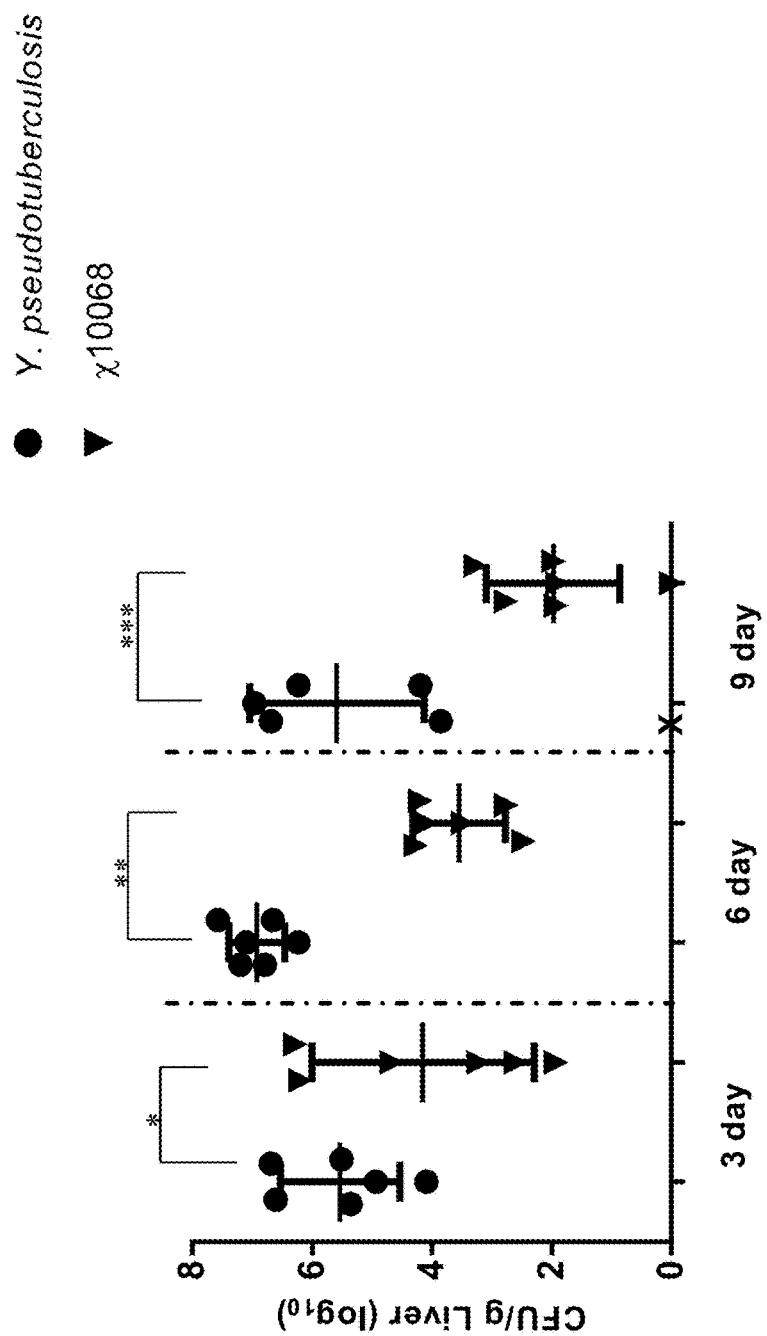

We measured serum IgG responses to the recombinant protein LcrV and F1 by ELISA. Results indicated that, by 2 weeks post-immunization, mice orally immunized with χ10069 (pYA5199) synthesizing YopE$_{Nt138}$-LcrV developed higher IgG titers to LcrV than that induced by immunization with χ10068 or χ10069 (pYA3332) and similar but higher IgG titers to LcrV by 4 weeks post-immunization (FIG. 14A). Mice orally immunized with χ10068 developed a high-level IgG response to F1 by 2 and 4 weeks post-immunization (FIG. 15A). Splenic lymphocytes isolated from mice immunized with χ10068, χ10069 (pYA3332) as a vector control, χ10069 (pYA5199), or BSG as a negative control were cultured with LcrV or F1 antigens for stimulation. The amounts of IFN-γ and IL-17 in the supernatants of cell cultures were assayed by ELISA. Results indicated that mice immunized with strains χ10068 or χ10069 (pYA5199) produced a significant level of IFN-γ and IL-17 compared to mice immunized with χ10069 (pYA3332) and BSG (FIGS. 14 B & C, and FIGS. 15 B & C).

Discussion

Our results demonstrated that oral immunization with recombinant attenuated *Y. pseudotuberculosis* mutants as vaccines afforded great protection against bubonic and pneumonic plague caused by *Y. pestis*, and Yersinosis caused by *Y. enterocolitica* and *Y. pseudotuberculosis* in mice. Bubonic plague is primarily a disease of rodents (with often enlarged lymph nodes and sometimes with typical bubos) that is spread by fleas in nature, humans are occasionally infected either by flea bite or by inhalational exposure, usually through a secondary host, such as, wild animals including guinea pigs (Gabastou et al., 2000), prairie dogs (CLARK, 1977, Rayor, 1985), squirrels (http://www.foxnews.com/health/2012/09/05/colorado-girl-recovering-from-bubonic-plague/, 2012), coyotes (Smego et al., 1999) and lion (Wong et al., 2009) or domestic cats (Doll et al., 1994) and dogs (Gould et al., 2008, Orloski & Eidson, 1995, Chomel et al., 1994, Pashine et al., 1999, Giambartolomei et al., 1999, Wang et al., 2011a) or, rarely, through another infected person. Lowering the incidence of *Y. pestis* infections in wild animals would likely reduce zoonotic transmission of the disease to humans. Therefore, palatable baits containing live vaccines for oral immunization to reduce infection of wild animals may be acceptable methods to control plague epidemics.

Yersiniosis caused by *Y. enterocolitica*, *Y. pseudotuberculosis* is prevalent in many mammalian hosts (such as dogs, cats, swine, horses, cattle, rabbits, deer and rodents). Thus, live attenuated *Y. pseudotuberculosis*-based vaccines probably can be used to prevent Yersinosis in farm animals such as swine, cattle and sheep.

Materials and Methods for Examples 8-13 (for the Most Part, Only Listed Different M&M that were Needed for Studies Reported in Examples 1-7)

Bacterial strains, plasmids, and culture conditions. All bacterial strains and plasmids used in this study are listed in Table 1. All strains were stored at −70° C. in peptone-glycerol. *Escherichia coli* χ6212 and χ7213 were used as an intermediate hosts for cloning procedures and grown routinely at 37° C. in LB broth (Bertani, 1951) or on LB solidified with 1.2% Bacto Agar (Difco). The *Y. enterocolitica* WA and *Y. pseudotuberculosis* PB1+ strain provided by Robert Perry (University of Kentucky) and used in this study was grown in LB medium at 27° C. When required, chloramphenicol (50 µg/ml, Cm), arabinose (0.1%) or 2, 6-diaminopimelic acid (DAP, 15 µg/ml) was added. TBA containing 5% sucrose was used for sacB gene-based counterselection in allelic exchange experiments. *Y. pestis* KIM6+ (pCD1Ap) was used for challenge studies as previously reported (Sun, 2011). *Y. pestis* cells were grown routinely on Congo red agar from peptone-glycerol stocks and in HIB at 28° C. (Straley & Bowmer, 1986). HIB Congo red agar plates were used to confirm the pigmentation (Pgm) phenotype of *Y. pestis* strains (Gong et al., 2001).

Construction of plasmids. All primers used in this study are listed in Table 5.

TABLE 5

Oligonucleotides used in Examples 8-13

| Name | Sequence | Seq. ID No. |
|---|---|---|
| lacZ-1 | 5' cggggtaccacggacctttagcaccgttctcga tagaga 3' (KpnI) | 17 |
| lacZ-2 | 5' cgagctcggcagcctgcaggccaaaaaccgcag ggcgcactacgaaga 3' | 18 |
| lacZ-3 | 5' cctgcaggctgccgagctcggcatcggtggggg ggcagaggcaagga 3' | 19 |
| lacZ-4 | 5' cggcccgggcggcaacttctaatccgggaatat ctga 3' (XmaI) | 20 |

TABLE 5 -continued

Oligonucleotides used in Examples 8-13

| Name | Sequence | Seq. ID No. |
|---|---|---|
| lacZ-UV | 5' gccaaaggccaattagattgcagtta 3' (KpnI) | 21 |
| lacZ-DV | 5' cgcgtgacatccgcggcaatggcga 3' | 22 |
| Caf-1 | 5' cggctgcaggcctattatattgcttcgcgctct ctattcttag 3' (PstI) | 23 |
| Caf-2 | 5' cgggagctccttttaatcatacaggtgattcc a 3' (SacI) | 24 |
| yopK-1 | 5' cggcccggggatagagcctacaataaattataa ccaatag 3' (XmaI) | 25 |
| yopK-2 | 5' ctccaactcagatttcatagttactactcccaa atttactttataaac 3' | 26 |
| yopK-3 | 5' gtaaatttgggagtagtaactatgaaatctgag ttggaggaattgagt 3' | 27 |
| yopK-4 | 5' gttccggtaccgccagcggtgatgggttac a 3' (KpnI) | 28 |
| yopK-DV | 5' gacacccaccgctcagtgcattgtgca 3' | 29 |
| yopJ-1 | 5' cggggtaccagccttgagttgatatatccgaga atag 3' (KpnI) | 30 |
| yopJ-2 | 5' tacattatacatccgatatatcagtttccaact gtgtta 3' | 31 |
| yopJ-3 | 5' gatatatcggatgtataatgtattttggaaatc ttgctcca 3' | 32 |
| yopJ-4 | 5' cggcccggggatattcagcgattgatcagatcg ctta 3' (XmaI) | 33 |

The restriction endonuclease sites are underlined

For construction of suicide vectors, primers lacZ-1/lacZ-2 and lacZ-3/lacZ-4 (Table 5) were used for amplifying the flanking regions of the lacZ gene from *Y. pseudotuberculosis* PB1/+, respectively. Then the DNA fragment containing the ΔlacZ was amplified using primers lacZ-1/lacZ-4 through overlapping PCR. The fused DNA segment (ΔlacZ) was ligated into the KpnI and XmaI sites of pRE112 to form plasmid pYA5243. In order to insert the caf1R-caf1M-caf1A-caf1 operon of *Y. pestis* into *Y. pseudotuberculosis* PB1/+, the cafR-cafA-cafM-caf1 operon of *Y. pestis* was amplified by Caf-1/Caf-2 primers and cloned into the PstI and SacI sites between the flanking regions of ΔlacZ in pYA5243 to form plasmid pYA5148. To delete the yopK gene from *Y. pseudotuberculosis* PB1/+, primers YopK-1/YopK-2 and YopK-3/YopK-4 (Table 5) were used for amplifying flanking regions of the ΔyopK gene, respectively. Then the DNA fragment containing the ΔyopK was amplified using primers YopK-1/YopK-4 through overlapping PCR. The fused flanking region (ΔyopK) was ligated into the KpnI and XmaI sites of pRE112 to form plasmid pYA5323. To delete the yopJ gene from *Y. pseudotuberculosis* PB1/+, primers YopJ-1/YopJ-2 and YopJ-3/YopJ-4 (Table 5) were used for amplifying flanking regions of the ΔyopJ gene, respectively. Then the DNA fragment containing the ΔyopJ was amplified using primers YopJ-1/YopJ-4 through overlapping PCR. The fused flanking region (ΔyopJ) was ligated into the KpnI and XmaI sites of pRE112 to form plasmid pYA5324. All the plasmid constructions were verified through sequencing.

Construction of *Y. pseutuberculosis* Mutants. The procedures were the same as the description in [0073] for Examples 1-12. All the mutant strains were confirmed by DNA sequence analysis.

Example 14

Generation of Recombinant Attenuated Derivatives of *Y. entercolitica* to Use as Vaccines to Prevent Infections Caused by *Yersinia* Species Causing Disease in Animals and Humans The means of attenuation and enhanced synthesis and display of protective *Yersinia* antigens as taught in Examples 1 to 13 can be used to render strains of *Y. entercolitica* attenuated and immunogenic so as to induce protective immunity against infections in animals and humans caused by pathogenic species of *Yersinia*.

Example 15

Generation of Recombinant Attenuated Derivatives of *Y. pestis* to Use as Vaccines to Prevent Infections Caused by *Yersinia* Species Causing Disease in Humans The means of attenuation and enhanced synthesis and display of protective *Yersinia* antigens as taught in Examples 1 to 13 can be used to render strains of *Y. pestis* attenuated and immunogenic so as to induce protective immunity against infections in humans caused by pathogenic species of *Yersinia*, including *Y. pestis* causing bubonic and pneumonic plague.

What is claimed is:

1. A recombinant attenuated *Yersinia pseudotuberculosis* bacterium, wherein the bacterium comprises Δasd, wherein the bacterium delivers a YopE$_{Nt138}$-LcrV fusion protein (N-terminal portion of YopE fused with LcrV of *Y. pestis*) by a Type 3 secretion system; and wherein the bacterium is capable of eliciting protective immune responses against plague caused by *Y. pestis* and Yersinosis caused by *Y. enterocolitica* or *Y. pseudotuberculosis* in a host.

2. A vaccine comprising a recombinant bacterium of claim 1.

3. The vaccine of claim 2, wherein the vaccine elicits a protective immune response against plague caused by *Y. pestis* and Yersinosis caused by either *Y. enterocolitica* or *Y. pseudotuberculosis*.

4. A method of inducing an immune response in a host, the method comprising administering a bacterium of claim 1 though bait to the host.

5. The method of claim 4, wherein the immune response is a protective immune response.

* * * * *